US012116699B2

(12) United States Patent
Hoyt et al.

(10) Patent No.: US 12,116,699 B2
(45) Date of Patent: Oct. 15, 2024

(54) MATERIALS AND METHODS FOR PROTEIN PRODUCTION

(71) Applicant: Impossible Foods Inc., Redwood City, CA (US)

(72) Inventors: Martin Andrew Hoyt, San Francisco, CA (US); Xiao Guo, Fremont, CA (US); Smita Shankar, Millbrae, CA (US)

(73) Assignee: Impossible Foods Inc., Redwood City, CA (US)

( * ) Notice: Subject to any disclaimer, the term of this patent is extended or adjusted under 35 U.S.C. 154(b) by 55 days.

(21) Appl. No.: 17/812,650

(22) Filed: Jul. 14, 2022

(65) Prior Publication Data
US 2022/0389616 A1 Dec. 8, 2022

Related U.S. Application Data

(62) Division of application No. 16/852,232, filed on Apr. 17, 2020, now Pat. No. 11,427,932.

(60) Provisional application No. 62/835,338, filed on Apr. 17, 2019.

(51) Int. Cl.
C40B 40/06 (2006.01)
C12N 9/04 (2006.01)
C12N 15/10 (2006.01)
C12N 15/81 (2006.01)

(52) U.S. Cl.
CPC ............ C40B 40/06 (2013.01); C12N 9/0006 (2013.01); C12N 15/1037 (2013.01); C12N 15/1086 (2013.01); C12Y 101/03013 (2013.01); C12N 15/815 (2013.01)

(58) Field of Classification Search
None
See application file for complete search history.

(56) References Cited

U.S. PATENT DOCUMENTS

| 4,158,065 A | 6/1979 | Sugino |
| 4,683,195 A | 7/1987 | Mullis |
| 4,683,202 A | 7/1987 | Mullis |
| 4,800,159 A | 1/1989 | Mullis |
| 4,965,188 A | 10/1990 | Mullis |
| 5,824,511 A | 10/1998 | Mattoon et al. |
| 6,261,827 B1 | 7/2001 | Elrod |
| 7,498,304 B2 | 3/2009 | Kotkow et al. |

(Continued)

FOREIGN PATENT DOCUMENTS

| CN | 1749399 | 3/2006 |
| CN | 101935657 | 1/2011 |

(Continued)

OTHER PUBLICATIONS

Adhikari et al., "Development of a lexicon for beef flavor in intact muscle," Journal of Sensory studies, Dec. 2011, 26(6):413-420.

(Continued)

Primary Examiner — Christian C Boesen
(74) Attorney, Agent, or Firm — Fish & Richardson P.C.

(57) ABSTRACT

This document relates to materials and methods for the production of protein. In one aspect, this document provides a nucleic acid construct including a first alcohol oxidase promoter element, wherein the first alcohol oxidase promoter element includes a mutation at one or more nucleotide positions corresponding to any of nucleotide positions 668-734 relative to SEQ ID NO: 28.

20 Claims, 27 Drawing Sheets
Specification includes a Sequence Listing.

(56) References Cited

U.S. PATENT DOCUMENTS

| | | | |
|---|---|---|---|
| 8,114,974 | B2 | 2/2012 | Picataggio et al. |
| 8,143,023 | B2 | 3/2012 | Takagi et al. |
| 8,236,528 | B2 | 8/2012 | Tsutsumi |
| 9,371,534 | B2 | 6/2016 | Matsuyama et al. |
| 9,938,326 | B2 | 4/2018 | Akeda et al. |
| 9,938,327 | B2 | 4/2018 | Shankar |
| 9,943,096 | B2 | 4/2018 | Fraser et al. |
| 10,039,306 | B2 | 8/2018 | Vrljic et al. |
| 10,273,492 | B2 | 4/2019 | Shankar |
| 10,689,656 | B2 | 6/2020 | Shankar et al. |
| 10,863,761 | B2 | 12/2020 | Brown et al. |
| 11,013,250 | B2 | 5/2021 | Vrljic et al. |
| 11,224,241 | B2 | 1/2022 | Fraser et al. |
| 11,319,544 | B2 | 5/2022 | Shankar et al. |
| 11,427,932 | B2 | 8/2022 | Hoyt et al. |
| 2007/0031832 | A1 | 2/2007 | Watt |
| 2009/0311680 | A1 | 12/2009 | Nakao et al. |
| 2010/0074998 | A1 | 3/2010 | Vega et al. |
| 2011/0129874 | A1 | 6/2011 | Tsutsumi et al. |
| 2011/0165661 | A1 | 7/2011 | Picataggio et al. |
| 2011/0287467 | A1 | 11/2011 | Crane |
| 2012/0156761 | A1 | 6/2012 | Picataggio et al. |
| 2013/0065814 | A1 | 3/2013 | Xu et al. |
| 2014/0030795 | A1 | 1/2014 | Donaldson et al. |
| 2014/0128287 | A1 | 5/2014 | Silverman et al. |
| 2015/0299716 | A1 | 10/2015 | Zhou |
| 2017/0188612 | A1 | 7/2017 | Varadan |
| 2017/0349637 | A1 | 12/2017 | Shanker et al. |
| 2018/0127764 | A1 | 5/2018 | Shankar |
| 2018/0371469 | A1 | 12/2018 | Shankar |
| 2020/0325484 | A1 | 10/2020 | Liang |
| 2020/0332267 | A1 | 10/2020 | Hoyt et al. |
| 2020/0340000 | A1 | 10/2020 | Roy-Chaudhuri et al. |
| 2021/0062206 | A1 | 3/2021 | Shih et al. |
| 2022/0290166 | A1 | 9/2022 | Shankar et al. |
| 2023/0193338 | A1 | 6/2023 | Roy-Chaudhuri et al. |

FOREIGN PATENT DOCUMENTS

| | | |
|---|---|---|
| EP | 1734121 | 12/2006 |
| EP | 2058398 | 5/2009 |
| EP | 2669375 | 12/2013 |
| EP | 3128006 | 2/2017 |
| JP | A-10-42873 | 2/1998 |
| JP | 2008017774 | 1/2008 |
| JP | A-2008-17733 | 1/2008 |
| JP | A-2009-505657 | 2/2009 |
| JP | A-2010-516268 | 5/2010 |
| JP | 2014-525255 | 9/2014 |
| JP | A-2018-515098 | 6/2018 |
| RU | 2658758 | 6/2018 |
| WO | WO 1997028273 | 8/1997 |
| WO | WO 2004099405 | 11/2004 |
| WO | WO 2006089329 | 8/2006 |
| WO | WO 2007025008 | 3/2007 |
| WO | WO 2012083424 | 6/2012 |
| WO | WO 2013010042 | 1/2013 |
| WO | WO 2013158749 | 10/2013 |
| WO | WO 2014008729 | 1/2014 |
| WO | WO 2014110532 | 7/2014 |
| WO | WO 2014110539 | 7/2014 |
| WO | WO 2015020537 | 2/2015 |
| WO | WO 2015153666 | 10/2015 |
| WO | WO 2016089516 | 6/2016 |
| WO | WO 2016183163 | 11/2016 |
| WO | WO 2019067558 | 4/2019 |

OTHER PUBLICATIONS

Berg et al., "Combinatorial Mutagenesis and Selection to Understand and Improve Yeast Promoters," BioMed Research International, Jun. 6, 2013, 2013:926985, 9 pages.

Berger, "Flavours and fragrances: chemistry, bioprocessing and sustainability," Springer Science & Business Media, Mar. 2007, 31 pages.

Berry et al., "Substitution of cysteine for selenocysteine in type I iodothyronine deiodinase reduces the catalytic efficiency of the protein but enhances its translation," Endocrinology, 1992, 131(4):1848-1852.

Burns et al., "A high molecular weight melanoma-associated antigen—specific chimeric antigen receptor redirects lymphocytes to target human melanomas," Cancer Research, 2010, 70(8):3027-3033.

CDC.gov [online], "Alpha-gal Syndrome Factsheet," Apr. 18, 2022, retrieved from URL<https://www.cdc.gov/ticks/alpha-gal/resources/alpha-gal-syndrome-factsheet.html>, 2 pages.

Dolferus et al., "Differential interactions of promoter elements in stress responses of the Arabidopsis adh gene," Plant Physiology, 1994, 105(4):1075-1087.

Dwivedi et al., "Meat flavor" Critical Reviews in Food Science & Nutrition, vol. 5, 487-535, 1975.

FDA "Labeling of Plant-Based Milk Alternatives and Voluntary Nutrient Statements: Guidance for Industry," Feb. 2023, 29 pages.

FDA.gov [online], "Standards of Identity for Food," Jun. 28, 2023, retrieved on Jul. 7, 2023, retrieved from URL<https://www.fda.gov/food/food-labeling-nutrition/standards-identity-food>, 5 pages.

Foodnavigator-usa.com [Online], "A gamechanger for flavor in meat alternatives . . . 'MotifFoodWorks to launch heme-binding protein delivering 'flavor and aroma of real meat," Sep. 17, 2021, retrieved on Oct. 23, 2022, retrieved from URL<https://www.foodnavigator-usa.com/Article/2021/09/17/Motif-FoodWorks-to-launch-myoglobin-a-yeast-derived-heme-binding-protein-delivering-the-flavor-and-aroma-of-real-meat>, 5 pages.

Gasser et al., "Antibody production with yeasts and filamentous fungi: on the road to large scale?," Biotechnology Letters, 2007, 29(2):201-212.

Impossible Foods Inc. v. Motif Foodworks, Inc., United States District Court, District of Delaware, Civil Action No. 1:22-cv-00311-WCB, Answer and Defenses by Ginkgo Bioworks, Inc. to Impossible, Inc.'s Third Amended Complaint, Dated Jul. 24, 2023, 75 pages.

Impossible Foods Inc. v. Motif Foodworks, Inc., United States District Court, District of Delaware, Civil Action No. 1:22-cv-00311-WCB, Answer to Complaint for Damages and Injunctive Relief and Counterclaims, dated Apr. 29, 2022, 20 pages.

Impossible Foods Inc. v. Motif Foodworks, Inc., United States District Court, District of Delaware, Civil Action No. 1:22-cv-00311-WCB, Answer to Counterclaims, dated May 20, 2022, 7 pages.

Impossible Foods Inc. v. Motif Foodworks, Inc., United States District Court, District of Delaware, Civil Action No. 1:22-cv-00311-WCB, Claim Construction Order, dated Mar. 22, 2024, 28 pages.

Impossible Foods Inc. v. Motif Foodworks, Inc., United States District Court, District of Delaware, Civil Action No. 1:22-cv-00311-WCB, Claim Construction Status Report, dated Feb. 23, 2024, 13 pages.

Impossible Foods Inc. v. Motif Foodworks, Inc., United States District Court, District of Delaware, Civil Action No. 1:22-cv-00311-WCB, Complaint for Damages and Injunctive Relief, dated Mar. 9, 2022, 100 pages.

Impossible Foods Inc. v. Motif Foodworks, Inc., United States District Court, District of Delaware, Civil Action No. 1:22-cv-00311-WCB, Declaration of Dr. Carl Batt in Support of Ginkgo Bioworks, Inc.'s Opening Claim Construction Brief, dated Jan. 12, 2024, 288 pages.

Impossible Foods Inc. v. Motif Foodworks, Inc., United States District Court, District of Delaware, Civil Action No. 1:22-cv-00311-WCB, Declaration of Dr. Carl Batt in Support of Ginkgo Bioworks, Inc.'s Reply Claim Construction Brief, dated Feb. 2, 2024, 24 pages.

Impossible Foods Inc. v. Motif Foodworks, Inc., United States District Court, District of Delaware, Civil Action No. 1:22-cv-00311-WCB, Declaration of Dr. Carl Batt , Dated Jun. 28, 2023, 565 pages.

Impossible Foods Inc. v. Motif Foodworks, Inc., United States District Court, District of Delaware, Civil Action No. 1:22-cv-

(56) References Cited

OTHER PUBLICATIONS

00311-WCB, Declaration of Dr. Geoffrey Lin-Cereghino in Support of Motif's Answering Claim Construction Brief (Public Version), dated Feb. 2, 2024, 314 pages.
Impossible Foods Inc. v. Motif Foodworks, Inc., United States District Court, District of Delaware, Civil Action No. 1:22-cv-00311-WCB, Declaration of Dr. Geoffrey Lin-Cereghino in Support of Motif's Sur-Reply Claim Construction Brief, dated Feb. 9, 2024, 40 pages.
Impossible Foods Inc. v. Motif Foodworks, Inc., United States District Court, District of Delaware, Civil Action No. 1:22-cv-00311-WCB, Declaration of Dr. Jerrad Legako, Dated Jun. 28, 2023, 1341 pages.
Impossible Foods Inc. v. Motif Foodworks, Inc., United States District Court, District of Delaware, Civil Action No. 1:22-cv-00311-WCB, Declaration of Dr. Jerrad Legako, Dated Jul. 14, 2023, 15 pages.
Impossible Foods Inc. v. Motif Foodworks, Inc., United States District Court, District of Delaware, Civil Action No. 1:22-cv-00311-WCB, Declaration of Hal Alper, Ph.D., dated Jan. 26, 2024, 612 pages.
Impossible Foods Inc. v. Motif Foodworks, Inc., United States District Court, District of Delaware, Civil Action No. 1:22-cv-00311-WCB, Declaration of Hal Alper, Ph.D., dated Jul. 7, 2023, 32 pages.
Impossible Foods Inc. v. Motif Foodworks, Inc., United States District Court, District of Delaware, Civil Action No. 1:22-cv-00311-WCB, Declaration of Hal Alper, Ph.D., in Support of Impossible Foods Inc.'s Sur-Reply Claim Construction Brief, dated Feb. 9, 2024, 106 pages.
Impossible Foods Inc. v. Motif Foodworks, Inc., United States District Court, District of Delaware, Civil Action No. 1:22-cv-00311-WCB, Declaration of Hal Alpert, Ph.D., dated Jun. 14, 2023, 504 pages.
Impossible Foods Inc. v. Motif Foodworks, Inc., United States District Court, District of Delaware, Civil Action No. 1:22-cv-00311-WCB, Declaration of Jennifer A. Ward in Support of Plaintiff's Opposition to Defendant's Partial Motion to Dismiss Plaintiff's Second Amended Complaint, dated Oct. 27, 2022, 75 pages.
Impossible Foods Inc. v. Motif Foodworks, Inc., United States District Court, District of Delaware, Civil Action No. 1:22-cv-00311-WCB, Declaration of Paul Sarnoski, Ph.D., dated Jul. 14, 2023, 188 pages.
Impossible Foods Inc. v. Motif Foodworks, Inc., United States District Court, District of Delaware, Civil Action No. 1:22-cv-00311-WCB, Declaration of Dr. Robert McGorrin, dated Jun. 28, 2023, 748 pages.
Impossible Foods Inc. v. Motif Foodworks, Inc., United States District Court, District of Delaware, Civil Action No. 1:22-cv-00311-WCB, Defendant Ginkgo Bioworks, Inc.'s Opening Claim Construction Brief (Redacted Public Version), dated Jan. 18, 2024, 342 pages.
Impossible Foods Inc. v. Motif Foodworks, Inc., United States District Court, District of Delaware, Civil Action No. 1:22-cv-00311-WCB, Defendant Ginkgo Bioworks, Inc.'s Reply Claim Construction Brief, dated Feb. 2, 2024, 90 pages.
Impossible Foods Inc. v. Motif Foodworks, Inc., United States District Court, District of Delaware, Civil Action No. 1:22-cv-00311-WCB, Defendant Motif Foodworks, Inc.'s Answer to Second Amended Complaint for Damages and Injunctive Relieve and Counterclaims, dated Nov. 28, 2022, 32 pages.
Impossible Foods Inc. v. Motif Foodworks, Inc., United States District Court, District of Delaware, Civil Action No. 1:22-cv-00311-WCB, Defendant Motif Foodworks, Inc.'s Answer to Third Amended Complaint for Damages and Injunctive Relief and Counterclaims, dated Jul. 17, 2023, 655 pages.
Impossible Foods Inc. v. Motif Foodworks, Inc., United States District Court, District of Delaware, Civil Action No. 1:22-cv-00311-WCB, Defendant Motif Foodworks, Inc.'s Answering Claim Construction Brief, dated Jul. 7, 2023, 528 pages.
Impossible Foods Inc. v. Motif Foodworks, Inc., United States District Court, District of Delaware, Civil Action No. 1:22-cv-00311-WCB, Defendant Motif Foodworks, Inc.'s Opening Brief in Support of Partial Motion to Dismiss Plaintiff's Second Amended Complaint, dated Oct. 13, 2022, 20 pages.
Impossible Foods Inc. v. Motif Foodworks, Inc., United States District Court, District of Delaware, Civil Action No. 1:22-cv-00311-WCB, Defendant Motif Foodworks, Inc.'s Reply Brief in Support of its Motion to Dismiss Plaintiff's Second Amended Complaint, dated Nov. 3, 2022, 16 pages.
Impossible Foods Inc. v. Motif Foodworks, Inc., United States District Court, District of Delaware, Civil Action No. 1:22-cv-00311-WCB, Defendant Motif Foodworks, Inc.'s Sur-Reply Claim Construction Brief, dated Jul. 19, 2023, 28 pages.
Impossible Foods Inc. v. Motif Foodworks, Inc., United States District Court, District of Delaware, Civil Action No. 1:22-cv-00311-WCB, Defendant Motif Foodworks, Inc.'s Unopposed Motion for Leave to File Amended Answer to Second Amended Complaint, dated Jun. 30, 2023, 705 pages.
Impossible Foods Inc. v. Motif Foodworks, Inc., United States District Court, District of Delaware, Civil Action No. 1:22-cv-00311-WCB, Defendant Motif Foodworks, Inc.'s Answering Claim Construction Brief (Public Version), dated Feb. 2, 2024, 283 pages.
Impossible Foods Inc. v. Motif Foodworks, Inc., United States District Court, District of Delaware, Civil Action No. 1:22-cv-00311-WCB, Defendant Motif Foodworks, Inc.'s Sur-Reply Claim Construction Brief, dated Feb. 9, 2024, 17 pages.
Impossible Foods Inc. v. Motif Foodworks, Inc., United States District Court, District of Delaware, Civil Action No. 1:22-cv-00311-WCB, Defendant's Initial Invalidity Contentions, dated May 5, 2023, 14 pages.
Impossible Foods Inc. v. Motif Foodworks, Inc., United States District Court, District of Delaware, Civil Action No. 1:22-cv-00311-WCB, First Amended Complaint for Damages and Injunctive Relief, dated Jul. 25, 2022, 395 pages.
Impossible Foods Inc. v. Motif Foodworks, Inc., United States District Court, District of Delaware, Civil Action No. 1:22-cv-00311-WCB, Joint Letter to The Honorable William C. Bryson on Behalf of the Parties Submitting Joint Claim Construction Chart, dated Dec. 15, 2023, 30 pages.
Impossible Foods Inc. v. Motif Foodworks, Inc., United States District Court, District of Delaware, Civil Action No. 1:22-cv-00311-WCB, Memorandum Opinion and Order, dated Nov. 14, 2022, 5 pages.
Impossible Foods Inc. v. Motif Foodworks, Inc., United States District Court, District of Delaware, Civil Action No. 1:22-cv-00311-WCB, Plaintiff Impossible Foods Inc.'s Answer to Defendant's Counterclaims, dated Dec. 19, 2022, 17 pages.
Impossible Foods Inc. v. Motif Foodworks, Inc., United States District Court, District of Delaware, Civil Action No. 1:22-cv-00311-WCB, Plaintiff Impossible Foods Inc.'s Answering Brief in Opposition to Defendant's Partial Motion to Dismiss Plaintiff's Second Amended Complaint, dated Oct. 27, 2022, 29 pages.
Impossible Foods Inc. v. Motif Foodworks, Inc., United States District Court, District of Delaware, Civil Action No. 1:22-cv-00311-WCB, Plaintiff Impossible Foods Inc.'s Claim Construction Reply Brief, dated Jul. 14, 2023, 508 pages.
Impossible Foods Inc. v. Motif Foodworks, Inc., United States District Court, District of Delaware, Civil Action No. 1:22-cv-00311-WCB, Plaintiff Impossible Foods Inc.'s Opening Brief in Support of Unopposed Motion for Leave to File Third Amended Complaint, dated Jul. 6, 2023, 34 pages.
Impossible Foods Inc. v. Motif Foodworks, Inc., United States District Court, District of Delaware, Civil Action No. 1:22-cv-00311-WCB, Plaintiff Impossible Foods Inc.'s Opening Claim Construction Brief (Redacted Version), dated Jun. 21, 2023, 129 pages.
Impossible Foods Inc. v. Motif Foodworks, Inc., United States District Court, District of Delaware, Civil Action No. 1:22-cv-00311-WCB, Plaintiff Impossible Foods Inc.'s Answering Claim Construction Brief, dated Jan. 26, 2024, 79 pages.
Impossible Foods Inc. v. Motif Foodworks, Inc., United States District Court, District of Delaware, Civil Action No. 1:22-cv-

(56) References Cited

OTHER PUBLICATIONS

00311-WCB, Plaintiff Impossible Foods Inc.'s Sur-Reply Claim Construction Brief, dated Feb. 9, 2024, 15 pages.
Impossible Foods Inc. v. Motif Foodworks, Inc., United States District Court, District of Delaware, Civil Action No. 1:22-cv-00311-WCB, Second Amended Complaint for Damages and Injunctive Relief, dated Sep. 7, 2022, 567 pages.
Impossible Foods Inc. v. Motif Foodworks, Inc., United States District Court, District of Delaware, Civil Action No. 1:22-cv-00311-WCB, Supplemental Declaration of Dr. Carl Batt, dated Jul. 14, 2023, 44 pages.
Impossible Foods Inc. v. Motif Foodworks, Inc., United States District Court, District of Delaware, Civil Action No. 1:22-cv-00311-WCB, Supplemental Declaration of Dr. Robert McGorrin, dated Jul. 14, 2023, 31 pages.
Impossible Foods Inc. v. Motif Foodworks, Inc., United States District Court, District of Delaware, Civil Action No. 1:22-cv-00311-WCB, Third Amended Complaint for Damages and Injunctive Relieve, dated Jul. 3, 2023, 602 pages.
Kim et al., "A 20 nucleotide upstream element is essential for the nopaline synthase (nos) promoter activity," Plant Molecular Biology, 1994, 24(1):105-117.
Ma, "Transcriptional activators and activation mechanisms," Protein & Cell, Nov. 2011, 2(11):879-888.
Macleod et al., "Natural and simulated meat flavors (with particular reference to beef)" Critical Reviews in Food Science & Nutrition, 1981, 14:309-437.
Manley, "Process Flavors," Source Book of Flavors, 1999, Chapter 5, 139-155.
Motif Foodworks, Inc., "GRAS Notice For Myoglobin Preparation," dated Apr. 14, 2021, 34 pages.
Nsf.org [online], "Plant-Based Certification," retrieved on Jul. 7, 2023, retrieved from URL<https://www.nsf.org/food-beverage/food-beverage-product-certification/plant-based-certification>, 16 pages.
Ordway et al., "Myoglobin: an essential hemoprotein in striated muscle," Journal of Experimental Biology, Sep. 15, 2004, 207(20):3441-3446.
Richman et al., "High-affinity GD2-specific CAR T cells induce fatal encephalitis in a preclinical neuroblastoma model," Cancer Immunology Research, 2018, 6(1):36-46.
Sensory-Directed Flavor Analysis, 1st ed., Marsili (ed.), 2006, Chapter 9, 45 pages.
Shahidi et al., "Flavor of Meat, Meat Products and Seafoods," 2nd edition, 1998, Chapter 3: 54 pages.
Song et al., "Contribution of beef base to aroma characteristics of beeflike process flavour assessed by descriptive sensory analysis and gas chromatography olfactometry and partial least squares regression," Journal of Chromatography A, Dec. 3, 2010, 1217(49):7788-7799.
Stevenson et al., "New Oxford American Dictionary Acid," Third Edition, 2010, 3 pages.
Stevenson et al., "New Oxford American Dictionary Animal," Third Edition, 2010, 3 pages.
Stevenson et al., "New Oxford American Dictionary M," Third Edition, 2010, 3 pages.
Wasserman, "Symposium on meat flavor chemical basis for meat flavor: a review," Journal of Food Science, Jan. 1979, 44(1):6-11.
Wilson et al., "Myoglobin," Encyclopedia of Respiratory Medicine, 2006, 7 pages.
Zellner et al., "Flavors and Odors," Chemical Analysis of Food: Techniques and Applications, 2012:599-663.
Zellner et al., "Gas chromatography—olfactometry in food flavour analysis," Journal of Chromatography A, Apr. 4, 2008, 1186(1-2):123-143.
Zhan et al., "Transcription factor Mxr1 promotes the expression of Aox1 by repressing glycerol transporter 1 in Pichia pastoris," FEMS Yeast Research, Jun. 2017, 17(4):fox015, 10 pages.
[No Author Listed] Impossible Foods Inc. "GRAS Notification for Soybean Leghemoglobin Protein Derived from Pichia Pastoris." GRAS notice 000540, Retrieved from internet <URL:https://www.fda.gov/Food/IngredientsPackagingLabeling/GRAS/NoticeInventory/default.htm.> dated Sep. 4, 2014, 109 pages, Redwood City, California.
[No Author Listed] Impossible Foods Inc. "GRAS Notification for Soybean Leghemoglobin Protein Derived from Pichia Pastoris." GRAS notice 000737, Retrieved from internet <URL:https://www.fda.gov/downloads/Food/IngredientsPackagingLabeling/GRAS/NoticeInventory/default.htm, 1063 pages, dated Oct. 2, 2017.
Ahmad et al., "Protein expression in Pichia pastoris: recent achievements and perspectives for heterologous protein production," Applied microbiology and biotechnology, Jun. 2014, 98:5301-5317.
Alberts et al., "Molecular Biology Of The Cell," 4th edition, 2002, 20 pages.
Bawa et al., "Functional recombinant protein is present in the pre-induction phases of Pichia pastoris cultures when grown in bioreactors, but not shake-flasks," Microbial cell factories, Dec. 2014, 13(1):1-13.
Benson et al., "GenBank," Nucleic Acids Research: Database Issue, 2014, 42:D32-D37.
Chenna et al., "Multiple sequence alignment with the Clustal series of programs," Nucleic acids research, Jul. 1, 2003, 31(13):3497-3500.
Chiruvolu, et al., "Recombinant protein production in an alcohol oxidase-defective strain of Pichia pastoris in fedbatch fermentations," Enzyme Microb. Technol., 1997, 21:277-83.
De Schutter et al., "Genome sequence of the recombinant protein production host Pichia pastoris," Nature biotechnology, Jun. 2009, 27(6):561-5666.
Declaration of Dr. Carl Batt, dated Jan. 27, 2023, 137pages.
Declaration of Dr. Carl Batt, dated Jan. 27, 2023, 174 pages.
Declaration of Dr. Geoffrey Lin-Cereghino, dated Jan. 27, 2023, 51 pages.
Declaration of Dr. Sylvia Hall-Ellis, dated Jan. 27, 2023, 196 pages.
Dey et al., "The nuclear transcription factor Rtg1p functions as a cytosolic, post-transcriptional regulator in the methylotrophic yeast Pichia pastoris," Journal of Biological Chemistry, Oct. 26, 2018, 293(43):16647-16660.
Engel et al., "Foods and food ingredients produced via recombinant DNA techniques: an overview," Genetically Modified Foods—Acs Symposium Series, 1995, Chapter 1:1-10.
Extended European Search Report in European Appln. No. 22151183.5, dated Jul. 13, 2022, 12 pages, Europe.
Ferreira, "Heme synthesis," Encyclopedia Of Biological Chemistry, 2013 539-542.
Fraser et al., "Safety evaluation of soy leghemoglobin protein preparation derived from pichia pastoris, intended for use as a flavor catalyst in plant-based meat," International Journal of Toxicology, 2018, 37(3):241-262.
Freeman, "Transcription and Translation," Biological Sciences, Chapter 16-18, 2d Edition, 2005, 338-400.
Garrocho-Villegas et al., "Plant hemoglobins: what we know six decades after their discovery," Gene, Aug. 15, 2007, 398(1-2):78-85.
GenBank Accession No. AAO72735.1, "ZnII/2cys6 transcription factor [Ogataea polymorpha]," Oct. 14, 2003, 1 page.
GenBank Accession No. AB909501.1, "Candida boidinii HAP2 gene for Hap complex component Hap2, complete cds, strain: S2," Aug. 20, 2015, 2 pages.
GenBank Accession No. AB909502.1, "Candida boidinii HAP3 gene for Hap complex component Hap3, complete cds, strain: S2," Aug. 20, 2015, 2 pages.
GenBank Accession No. AB909503.1, "Candida boidinii HAP5 gene for Hap complex component Hap5, complete cds, strain: S2," Aug. 20, 2015, 2 pages.
GenBank Accession No. BAA24685.1, "leghemoglobin [Pisum sativum]," date Mar. 27, 2009, 3 pages.
GenBank Accession No. BAQ21465.1, "Hap complex component Hap2 [[Candida] boidinii]," Aug. 20, 2015, 1 pages.
GenBank Accession No. BAQ21466.1, "Hap complex component Hap3 [[Candida] boidinii]," Aug. 20, 2015, 1 page.
GenBank Accession No. BAQ21467.1, "Hap complex component Hap5 [[Candida] boidinii], " Aug. 20, 2015, 1 pages.

(56) References Cited

OTHER PUBLICATIONS

GenBank Accession No. NF102272.2, "Protein Family Model PF00042 (heme-biding globins)," dated Jan. 27, 2021, 27 pages.
GenBank Accession No. NP_001235248.2, "leghemoglobin C2 [Glycine max]," Jul. 2, 2020, 2 pages.
GenBank Accession No. X79871.1, "P.pastoris AOX2 gene, promoter region," dated Jul. 26, 2016, 2 pages.
GenBank Accession No. XM_001181118.1, "Predicted: Strongylocentrotus purpuratus hypothetical LOC583846 (LOC583846), mRNA," Oct. 9, 2006, 2 pages.
GenBank Accession No. XM_001183322.1, "Predicted: Strongylocentrotus purpuratus similar to ubiquitin conjugating enzyme 12 (LOC759045), partial mRNA," Oct. 7, 2006, 1 page.
GenBank Accession No. XM_002489984.1, "Komagataella phaffii GS115 Transcription factor (bHLH) involved in interorganelle communication (PAS_chr1-1 0371), partial mRNA," Oct. 11, 2017, 2 pages.
GenBank Accession No. XM_002492633.1, "Komagataella phaffii GS115 Sensor of mitochondrial dysfunction (PAS_chr3_0452), partial mRNA," Oct. 11, 2023, 2 pages.
GenBank Accession No. XM_002493021.1, "Komagataella phaffii GS115 Hypothetical protein (PAS_chr3_0836), partial mRNA," Oct. 11, 2017, 2 pages.
GenBank Accession No. XM_002493563.1, "Komagataella phaffii GS115 Proposed transcriptional activator, member of the Gal4p family of zinc cluster proteins (PAS_chr4_0203), partial mRNA," Oct. 11, 2017, 3 pages.
GenBank Accession No. XP_002490029.1, "Transcription factor (bHLH) involved in interorganelle communication [Komagataella phaffii GS115]," Oct. 11, 2017, 2 pages.
GenBank Accession No. XP_002492481.1: Ferrochelatase [Komagataella phaffi GS115], dated Oct. 11, 2017, 3 pages.
GenBank Accession No. XP_002492678.1, "Sensor of mitochondrial dysfunction [Komagataella phaffii GS115]," Oct. 11, 2017, 2 pages.
GenBank Accession No. XP_002493066.1, "Hypothetical protein PAS_chr3_0836 [Komagataella phaffii GS115]," Oct. 11, 2017, 2 pages.
GenBank Accession No. XP_002493608.1, "Proposed transcriptional activator, member of the Gal4p family of zinc cluster proteins [Komagataella phaffii GS115]," Oct. 11, 2017, 2 pages.
GenBank Accession No. XP_002493846.1 Delta-aminolevulinate dehydratase, a homooctameric enzyme [Komagataella phaffi GS115], dated Oct. 11, 2017.
GenBank Accession No. XP_011262.1, "gamma-aminobutyric acid (GABA) A receptor, alpha 1 precursor [*Homo sapiens*]," Feb. 9, 2001, 1 page.
GenBank Accession No. XP_014574.1, "hypothetical protein FLJ22386 [*Homo sapiens*]," Apr. 16, 2001, 1 page.
Guarna et al., "On-line monitoring and control of methanol concentration in shake-flask cultures of Pichia pastoris," Biotechnology and bioengineering, Nov. 5, 1997, 56(3):279-286.
Haon et al., "Recombinant protein production facility for fungal biomass-degrading enzymes using the yeast Pichia pastoris," Frontiers in microbiology, Sep. 23, 2015, 6(1002): 12 pages.
Hargrove, et al., "Characterization of recombinant soybean leghemoglobin a and apolar distal histidine mutants, " J. Mol. Biol., 1997, 266:1032-1042.
Hartner et al., "Promoter library designed for fine-tuned gene expression in Pichia pastoris," Nucleic acids research, Jul. 1, 2008, 36(12): e76, 15 pages.
Hartner et al., "Regulation of methanol utilisation pathway genes in yeasts," Microbial cell factories, Dec. 2006, 5(39):1-21.
Hong et al., "Fermentation strategies for improved heterologous expression of laccase in Pichia pastoris," Biotechnology and Bioengineering, Aug. 20, 2002, 79(4):438- 449.
Inan & Meagher, "Non-repressing carbon sources for alcohol oxidase (AOX1) promoter of Pichia pastoris," J. Biosci. Bioeng., 2001, 92:585-589.
International Preliminary Report on Patentability in International Appln. No. PCT/US2016/031797, dated Nov. 14, 2017, 6 pages.
International Search Report and Written Opinion in International Appln. No. PCT/US2016/031797, dated Sep. 20, 2016, 9 pages.
International Search Report in International Appln. No. PCT/US2022/053003, mailed Mar. 14, 2023, 13 pages.
Katakura et al., "Effect of methanol concentration on the production of human β2-glycoprotein I domain V by a recombinant Pichia pastoris: a simple system for the control of methanol concentration using a semiconductor gas sensor," Journal of Fermentation and Bioengineering, Jan. 1, 1998, 86(5):482-487.
Kelly et al., "Cultivation of methylotrophs," In Hydrocarbon and Lipid Microbiology Protocols: Isolation and Cultivation, Dec. 6, 2014, 33 pages.
Kranthi et al., "Identification of key DNA elements involved in promoter recognition by Mxr1p, a master regulator of methanol utilization pathway in Pichia pastoris," Biochimica et Biophysica Acta (BBA)-Gene Regulatory Mechanisms, Jun. 1, 2009, 1789(6-8):460-468.
Kurtz et al., "Development of autonomously replicating plasmids for Candida albicans," Molecular and Cellular Biology, Jan. 1987, 7(1):209-217.
Lin-Cereghino et al., "Heterologous protein expression in the methylotrophic yeast Pichia pastoris," FEMS microbiology reviews, Jan. 1, 2000, 24(1):45-66.
Lin-Cereghino, et al., "Mxr1p, a key regulator of the methanol utilization pathway and peroxisomal genes in Pichia pastoris," Mol. and Cell. Biol., 2006, 26:883-897.
Liu, et al., "Balanced globin protein expression and heme biosynthesis improve production of human hemoglobin in *Saccharomyces cerevisiae*," Metabolic Engineering, 2014, 21:9-16.
Miele, et al., "A GATA-type transcription factor regulates expression of the high-affinity iron uptake system in the methylotrophic yeast Pichia pastoris," Arch. Biochem. Biophys., 2007, 465:172-179.
Mitrophanov, et al., "Positive autoregulation shapes response timing and intensity in twocomponent signal transduction systems," J. Mol. Biol., 2010, 401(4):671-680.
Mitrophanov, et al., "Positive feedback cellular control systems," Bioessays, 2008, 30(6):542-555.
NCBI Resource Coordinators, "Database resources of the national center for biotechnology information," Nucleic acids research, Nov. 28, 2015, 44:D6-D19.
Nicola et al., "Structural rearrangements due to ligand binding and haem replacement in myoglobin and leghaemoglobins," European Journal of Biochemistry, Aug. 1977, 78(1):133-140.
Parua et al., "Pichia pastoris 14-3-3 regulates transcriptional activity of the methanol inducible transcription factor Mxr1 by direct interaction," Molecular microbiology, Jul. 2012, 85(2):282-298.
Pereira et al., "Conserved regulation of the Hansenula polymorpha MOX promoter in *Saccharomyces cerevisiae* reveals insights in the transcriptional activation by Adr1p," European journal of biochemistry, May 1996, 238(1):181-191.
Proulx, et al., "Iron bioavailability of hemoglobin from soy root nodules using a caco-2 cell culture model," J. Agric. Food Chem., 2006, 54:1518-1522.
Rabert et al., "Recombinants proteins for industrial uses: utilization of Pichia pastoris expression system," Brazilian Journal of Microbiology, 2013, 44:351-356.
Roggenkamp et al., "Transformation of the methylotrophic yeast Hansenula polymorpha by autonomous replication and integration vectors," Molecular and General Genetics MGG, Feb. 1986, 202:302-308.
Rumyantsev et al., "Effects of deletions in pichia pastoris RTG genes on phenotype and AOX1 expression, " Advances in Microbiology, May 29, 2018, 8(5):439-450.
Sasano et al., "Trm1p, a Zn (II) 2Cys6-type transcription factor, is a master regulator of methanol-specific gene activation in the methylotrophic yeast Candida boidinii," Eukaryotic Cell, Mar. 2008, 7(3):527-536.
Sasano, et al., "Trm2p-dependent depression is essential for methanol-specific gene activation in the methylotrophic yeast Candid boidinii," FEMS Yeast Res., 2010, 10:535-544.

(56) References Cited

OTHER PUBLICATIONS

Sreekrishna, "Pichia, optimization of protein expression," Encyclopedia of industrial biotechnology: bioprocess, bioseparation, and cell technology, Flickinger MC. Hoboken, New Jersey: John Wiley and Sons, Inc., 2010:1-16.
Stryjewska et al., "Biotechnology and genetic engineering in the new drug development. Part I. DNA technology and recombinant proteins," Pharmacological reports, Sep. 2013, 65(5):1075-1085.
Supplementary European Search Report and Opinion in EP Appln. No. EP 16793420.7, dated Aug. 29, 2018,8 pages.
Trinh et al., "Effect of methanol feeding strategies on production and yield of recombinant mouse endostatin from Pichia pastoris," Biotechnology and Bioengineering, May 20, 2003, 82(4):438-444.
UniprotKB Accession No. P02236, "Leghemoglobin C2," dated Nov. 1, 1988, 9 pages.
Vedvick et al., "High-level secretion of biologically active aprotinin from the yeast Pichia pastoris," Journal of industrial microbiology and biotechnology, Apr. 1, 1991, 7(3):197-201.
Vogl et al., "A toolbox of diverse promoters related to methanol utilization: functionally verified parts for heterologous pathway expression in Pichia pastoris," ACS synthetic biology, Feb. 19, 2016, 5(2): 172-186.
Vogl et al., "Regulation of Pichia pastoris promoters and its consequences for protein production," New biotechnology, May 25, 2013, 30(4):385-404.
Wang et al., "Mit1 transcription factor mediates methanol signaling and regulates the alcohol oxidase 1 (AOX1) promoter in Pichia pastoris," Journal of Biological Chemistry, Mar. 18, 2016, 291(12):6245-6261.
Yurimoto et al., "Methanol-inducible gene expression and heterologous protein production in the methylotrophic yeast Candida boidinii," Biotechnology and applied biochemistry, Jun. 2009, 85-92, 53(2), Great Britain.
Zhang et al., "Heterologous protein expression in yeasts and filamentous fungi," Manual of Industrial Microbiology and Biotechnology, Mar. 25, 2010, 145-156.
Chenna, et al., "Multiple sequence alignment with the Clustal series of programs" Nucleic Acids Res., 2003, 31(13):3497-3500.
Dayhoff et al., "A Model of Evolutionary Change in Proteins," Atlas of Protein Sequence and Structure, 1978, 5(Suppl. 3):345-352.
GenBank Accession No. AB365355.1, "Candida boidinii TRM1 gene for Zn(II)2Cys6-type transcription factor Trm1, complete cds," dated Mar. 22, 2008, 3 pages.
GenBank Accession No. AB548760.1, "Candida boidinii TRM2 gene for C2H2-type transcription factor Trm2, complete cds," dated Jul. 17, 2010, 3 pages.
GenBank Accession No. ABD57365.1, "methanol expression regulator I [Komagataella pastoris]," dated Mar. 4, 2006, 2 pages.
GenBank Accession No. AEOI02000005.1, bases 858873 to 862352, "Ogataea parapolymorpha DL-1 chr3, whole genome shotgun sequence," dated Dec. 3, 2013, 186 pages.
GenBank Accession No. AF066054.1, "Pichia pastoris formaldehyde dehydrogenase (FLD1) gene, complete cds," dated Sep. 17, 1998, 2 pages.
GenBank Accession No. AY288296.1, "Pichia pastoris 3-phosphoglycerate kinase (PGK1) gene, complete cds," dated Jul. 22, 2005, 2 pages.
GenBank Accession No. BAF99700.1, "Zn(II)2Cys6-type transcription factor Trm1 [Candida boidinii]," dated Mar. 22, 2008, 2 pages.
GenBank Accession No. BAJ07608.1, "C2H2-type transcription factor Trm2 [Candida boidinii]," dated Jul. 17, 2010, 1 page.
GenBank Accession No. CAY70887.1, "Hypothetical protein PAS_chr3_0836 [Komagataella phaffii GS115]," dated Feb. 27, 2015, 2 pages.
GenBank Accession No. DQ395124.1, "Pichia pastoris methanol expression regulator I gene, complete cds," dated Mar. 4, 2006, 2 pages.
GenBank Accession No. ESX01253.1, "Regulatory protein ADR1 [Ogataea parapolymorpha DL-1]," dated Dec. 3, 2013, 2 pages.
GenBank Accession No. FJ752551.1, "Pichia pastoris dihydroxyacetone synthase 1 (DAS1) gene, complete cds" dated Mar. 21, 2009, 2 pages.
GenBank Accession No. U62648.1, "Pichia pastoris glyceraldehyde-3-phosphate dehydrogenase (GAP) gene, complete cds," dated Mar. 7, 1997, 2 pages.
GenBank Accession No. X02425.1, "Hansenula polymorpha MOX gene for methanol oxidase" dated Oct. 23, 2008, 3 pages.
GenBank Accession No. XM_002490678.1, "Komagataella phaffii GS115 Hypothetical protein (PAS_chr1-4_0586), partial Mrna," dated Jul. 22, 2009, 2 pages.
GenBank Accession No. YSAAODIA, "Candida boidinii methanol oxidase (AOD1) gene, complete cds," dated Apr. 27, 1993, 2 pages.
Hoffman, et al., "Identification of rate-limiting steps in yeast heme biosynthesis," Biochem. Biophys. Res. Commun., 2003, 310(4):1247-1253.
International Preliminary Report on Patentability in PCT Appln. No. PCT/US2020/028858, dated Oct. 28, 2021, 8 pages.
International Search Report and Written Opinion in PCT Appln. No. PCT/US2020/028858, dated Jun. 30, 2020, 13 pages.
Krainer, et al., "Optimizing cofactor availability for the production of recombinant heme peroxidase in Pichia pastoris," Microbial Cell Factories, 2015, 14(4):1-9.
Kranthi, et al., "Identification of Mxr1p-binding sites in the promoters of genes encoding dihydroxyacetone synthase and peroxin 8 of the methylotrophic yeast Pichia pastoris," Yeast, 2010, 27:705-711.
Liachko et al., "An autonomously replicating sequence for use in a wide range of budding yeasts," FEMS yeast research, Mar. 1, 2014, 4(2):364-367.
McCullum, et al., "Random Mutagenesis by Error-Prone PCR," Methods in Molecular Biology, 2010, 634:103-109.
Nakagawa, et al., "Alcohol oxidase hybrid oligomers formed in vivo and in vitro," Yeast, 1999, 15:1223-1230.
Ohi et al., "The positive and negative cis-acting elements for methanol regulation in the Pichia pastoris AOX2 gene," Molecular and General Genetics, 1994, 243(5):489-499.
Raymond, et al., "Development of the methylotrophic yeast Pichia methanolica for the expression of the 65 kilodalton isoform of human glutamate decarboxylase," Yeast, 1998, 14:11-23.
Impossible Foods Inc. v. Motif Foodworks, Inc. and Ginko Bioworks, Inc., United States District Court, District of Delaware, Civil Action No. 1:22-cv-00311-WCB, Claim Construction Order, dated Aug. 15, 2023, 22 pages.
Impossible Foods Inc. v. Motif Foodworks, Inc., United States District Court, District of Delaware, Civil Action No. 1:22-cv-00311-WCB, Plaintiff Impossible Foods Inc.'s Answer To Defendant Motif Foodworks, Inc.'s Counterclaims, Dated Aug. 7, 2023, 19 pages.
Li et al., "[Research progress on the promoter of Pichia pastoris alcohol oxidase gene AOX1 Progress in Promoter of Alcohol Oxidase Gene aox1 from Pichia pastoris]," Biotechnology, Aug. 15, 2013, 4:83-87 (English abstract only).
Motif Foodworks, Inc., Petitioner, v. Impossible Foods Inc., Patent Owner, Case No. IPR2023-00321, U.S. Pat. No. 10,689,656, dated Feb. 9, 2023, 7 pages.
Motif Foodworks, Inc., Petitioner, v. Impossible Foods Inc., Patent Owner, Case No. IPR2023-00321, U.S. Pat. No. 10,689,656, Decision dated Aug. 7, 2023, 27 pages.
Motif Foodworks, Inc., Petitioner, v. Impossible Foods Inc., Patent Owner, Case No. IPR2023-00322, U.S. Pat. No. 10,273,492, dated Feb. 9, 2023, 7 pages.
Motif Foodworks, Inc., Petitioner, v. Impossible Foods Inc., Patent Owner, Case No. IPR2023-00322, U.S. Pat. No. 10,273,492, Decision dated Aug. 7, 2023, 19 pages.
Portela et al., "Pichia pastoris Alcohol Oxidase 1 (AOX1) Core Promoter Engineering by High Resolution Systematic Mutagenesis," Biotechnology Journal, Nov. 22, 2017, 13(3):e1700340, 8 pages.

FIG 1

<110> Impossible Foods Inc.

<210> 1
<211> 161
<212> PRT
<213> Vigna radiata

<400> 1
Met Thr Thr Thr Leu Glu Arg Gly Phe Thr Glu Glu Gln Glu Ala Leu
1               5                   10                  15
Val Val Lys Ser Trp Asn Val Met Lys Lys Asn Ser Gly Glu Leu Gly
            20                  25                  30
Leu Lys Phe Phe Leu Lys Ile Phe Glu Ile Ala Pro Ser Ala Gln Lys
        35                  40                  45
Leu Phe Ser Phe Leu Arg Asp Ser Thr Val Pro Leu Glu Gln Asn Pro
    50                  55                  60
Lys Leu Lys Pro His Ala Val Ser Val Phe Val Met Thr Cys Asp Ser
65                  70                  75                  80
Ala Val Gln Leu Arg Lys Ala Gly Lys Val Thr Val Arg Glu Ser Asn
                85                  90                  95
Leu Lys Lys Leu Gly Ala Thr His Phe Arg Thr Gly Val Ala Asn Glu
            100                 105                 110
His Phe Glu Val Thr Lys Phe Ala Leu Leu Glu Thr Ile Lys Glu Ala
        115                 120                 125
Val Pro Glu Met Trp Ser Pro Ala Met Lys Asn Ala Trp Gly Glu Ala
    130                 135                 140
Tyr Asp Gln Leu Val Asp Ala Ile Lys Tyr Glu Met Lys Pro Pro Ser
145                 150                 155                 160
Ser

<210> 2
<211> 133
<212> PRT
<213> Methylacidiphilum infernorum

<400> 2
Met Ile Asp Gln Lys Glu Lys Glu Leu Ile Lys Glu Ser Trp Lys Arg
1               5                   10                  15
Ile Glu Pro Asn Lys Asn Glu Ile Gly Leu Leu Phe Tyr Ala Asn Leu
            20                  25                  30
Phe Lys Glu Glu Pro Thr Val Ser Val Leu Phe Gln Asn Pro Ile Ser
        35                  40                  45
Ser Gln Ser Arg Lys Leu Met Gln Val Leu Gly Ile Leu Val Gln Gly

FIG. 1 - CONTINUED

```
            50                      55                      60
Ile Asp Asn Leu Glu Gly Leu Ile Pro Thr Leu Gln Asp Leu Gly Arg
 65                      70                      75                      80
Arg His Lys Gln Tyr Gly Val Val Asp Ser His Tyr Pro Leu Val Gly
                    85                      90                      95
Asp Cys Leu Leu Lys Ser Ile Gln Glu Tyr Leu Gly Gln Gly Phe Thr
                    100                     105                     110
Glu Glu Ala Lys Ala Ala Trp Thr Lys Val Tyr Gly Ile Ala Ala Gln
                    115                     120                     125
Val Met Thr Ala Glu
                    130
```

<210> 3
<211> 139
<212> PRT
<213> Aquifex aeolicus

<400> 3
```
Met Leu Ser Glu Glu Thr Ile Arg Val Ile Lys Ser Thr Val Pro Leu
  1                       5                      10                      15
Leu Lys Glu His Gly Thr Glu Ile Thr Ala Arg Met Tyr Glu Leu Leu
                    20                      25                      30
Phe Ser Lys Tyr Pro Lys Thr Lys Glu Leu Phe Ala Gly Ala Ser Glu
                    35                      40                      45
Glu Gln Pro Lys Lys Leu Ala Asn Ala Ile Ile Ala Tyr Ala Thr Tyr
                    50                      55                      60
Ile Asp Arg Leu Glu Glu Leu Asp Asn Ala Ile Ser Thr Ile Ala Arg
 65                      70                      75                      80
Ser His Val Arg Arg Asn Val Lys Pro Glu His Tyr Pro Leu Val Lys
                    85                      90                      95
Glu Cys Leu Leu Gln Ala Ile Glu Glu Val Leu Asn Pro Gly Glu Glu
                    100                     105                     110
Val Leu Lys Ala Trp Glu Glu Ala Tyr Asp Phe Leu Ala Lys Thr Leu
                    115                     120                     125
Ile Thr Leu Glu Lys Lys Leu Tyr Ser Gln Pro
                    130                     135
```

<210> 4
<211> 145
<212> PRT
<213> Glycine max

<400> 4
```
Met Gly Ala Phe Thr Glu Lys Gln Glu Ala Leu Val Ser Ser Ser Phe
  1                       5                      10                      15
```

FIG. 1 - CONTINUED

```
Glu Ala Phe Lys Ala Asn Ile Pro Gln Tyr Ser Val Val Phe Tyr Thr
             20                  25                  30
Ser Ile Leu Glu Lys Ala Pro Ala Ala Lys Asp Leu Phe Ser Phe Leu
             35                  40                  45
Ser Asn Gly Val Asp Pro Ser Asn Pro Lys Leu Thr Gly His Ala Glu
             50                  55                  60
Lys Leu Phe Gly Leu Val Arg Asp Ser Ala Gly Gln Leu Lys Ala Asn
 65                  70                  75                  80
Gly Thr Val Val Ala Asp Ala Ala Leu Gly Ser Ile His Ala Gln Lys
             85                  90                  95
Ala Ile Thr Asp Pro Gln Phe Val Val Val Lys Glu Ala Leu Leu Lys
             100                 105                 110
Thr Ile Lys Glu Ala Val Gly Asp Lys Trp Ser Asp Glu Leu Ser Ser
             115                 120                 125
Ala Trp Glu Val Ala Tyr Asp Glu Leu Ala Ala Ala Ile Lys Lys Ala
             130                 135                 140
Phe
145
```

<210> 5
<211> 162
<212> PRT
<213> Hordeum vulgare

<400> 5
```
Met Ser Ala Ala Glu Gly Ala Val Val Phe Ser Glu Glu Lys Glu Ala
 1               5                  10                  15
Leu Val Leu Lys Ser Trp Ala Ile Met Lys Lys Asp Ser Ala Asn Leu
             20                  25                  30
Gly Leu Arg Phe Phe Leu Lys Ile Phe Glu Ile Ala Pro Ser Ala Arg
             35                  40                  45
Gln Met Phe Pro Phe Leu Arg Asp Ser Asp Val Pro Leu Glu Thr Asn
             50                  55                  60
Pro Lys Leu Lys Thr His Ala Val Ser Val Phe Val Met Thr Cys Glu
 65                  70                  75                  80
Ala Ala Ala Gln Leu Arg Lys Ala Gly Lys Ile Thr Val Arg Glu Thr
             85                  90                  95
Thr Leu Lys Arg Leu Gly Gly Thr His Leu Lys Tyr Gly Val Ala Asp
             100                 105                 110
Gly His Phe Glu Val Thr Arg Phe Ala Leu Leu Glu Thr Ile Lys Glu
             115                 120                 125
Ala Leu Pro Ala Asp Met Trp Gly Pro Glu Met Arg Asn Ala Trp Gly
             130                 135                 140
Glu Ala Tyr Asp Gln Leu Val Ala Ala Ile Lys Gln Glu Met Lys Pro
145                 150                 155                 160
Ala Glu
```

FIG. 1 - CONTINUED

<210> 6
<211> 1153
<212> PRT
<213> Magnaporthe oryzae

<400> 6
Met Asp Gly Ala Val Arg Leu Asp Trp Thr Gly Leu Asp Leu Thr Gly
1 5 10 15
His Glu Ile His Asp Gly Val Pro Ile Ala Ser Arg Val Gln Val Met
20 25 30
Val Ser Phe Pro Leu Phe Lys Asp Gln His Ile Ile Met Ser Ser Lys
35 40 45
Glu Ser Pro Ser Arg Lys Ser Ser Thr Ile Gly Gln Ser Thr Arg Asn
50 55 60
Gly Ser Cys Gln Ala Asp Thr Gln Lys Gly Gln Leu Pro Pro Val Gly
65 70 75 80
Glu Lys Pro Lys Pro Val Lys Glu Asn Pro Met Lys Lys Leu Lys Glu
85 90 95
Met Ser Gln Arg Pro Leu Pro Thr Gln His Gly Asp Gly Thr Tyr Pro
100 105 110
Thr Glu Lys Lys Leu Thr Gly Ile Gly Glu Asp Leu Lys His Ile Arg
115 120 125
Gly Tyr Asp Val Lys Thr Leu Leu Ala Met Val Lys Ser Lys Leu Lys
130 135 140
Gly Glu Lys Leu Lys Asp Asp Lys Thr Met Leu Met Glu Arg Val Met
145 150 155 160
Gln Leu Val Ala Arg Leu Pro Thr Glu Ser Lys Lys Arg Ala Glu Leu
165 170 175
Thr Asp Ser Leu Ile Asn Glu Leu Trp Glu Ser Leu Asp His Pro Pro
180 185 190
Leu Asn Tyr Leu Gly Pro Glu His Ser Tyr Arg Thr Pro Asp Gly Ser
195 200 205
Tyr Asn His Pro Phe Asn Pro Gln Leu Gly Ala Ala Gly Ser Arg Tyr
210 215 220
Ala Arg Ser Val Ile Pro Thr Val Thr Pro Pro Gly Ala Leu Pro Asp
225 230 235 240
Pro Gly Leu Ile Phe Asp Ser Ile Met Gly Arg Thr Pro Asn Ser Tyr
245 250 255
Arg Lys His Pro Asn Asn Val Ser Ser Ile Leu Trp Tyr Trp Ala Thr
260 265 270
Ile Ile Ile His Asp Ile Phe Trp Thr Asp Pro Arg Asp Ile Asn Thr
275 280 285
Asn Lys Ser Ser Ser Tyr Leu Asp Leu Ala Pro Leu Tyr Gly Asn Ser
290 295 300
Gln Glu Met Gln Asp Ser Ile Arg Thr Phe Lys Asp Gly Arg Met Lys
305 310 315 320

FIG. 1 - CONTINUED

```
Pro Asp Cys Tyr Ala Asp Lys Arg Leu Ala Gly Met Pro Pro Gly Val
                325                 330                 335
Ser Val Leu Leu Ile Met Phe Asn Arg Phe His Asn His Val Ala Glu
            340                 345                 350
Asn Leu Ala Leu Ile Asn Glu Gly Gly Arg Phe Asn Lys Pro Ser Asp
            355                 360                 365
Leu Leu Glu Gly Glu Ala Arg Glu Ala Ala Trp Lys Lys Tyr Asp Asn
            370                 375                 380
Asp Leu Phe Gln Val Ala Arg Leu Val Thr Ser Gly Leu Tyr Ile Asn
385                 390                 395                 400
Ile Thr Leu Val Asp Tyr Val Arg Asn Ile Val Asn Leu Asn Arg Val
                405                 410                 415
Asp Thr Thr Trp Thr Leu Asp Pro Arg Gln Asp Ala Gly Ala His Val
                420                 425                 430
Gly Thr Ala Asp Gly Ala Glu Arg Gly Thr Gly Asn Ala Val Ser Ala
                435                 440                 445
Glu Phe Asn Leu Cys Tyr Arg Trp His Ser Cys Ile Ser Glu Lys Asp
    450                 455                 460
Ser Lys Phe Val Glu Ala Gln Phe Gln Asn Ile Phe Gly Lys Pro Ala
465                 470                 475                 480
Ser Glu Val Arg Pro Asp Glu Met Trp Lys Gly Phe Ala Lys Met Glu
                485                 490                 495
Gln Asn Thr Pro Ala Asp Pro Gly Gln Arg Thr Phe Gly Gly Phe Lys
                500                 505                 510
Arg Gly Pro Asp Gly Lys Phe Asp Asp Asp Leu Val Arg Cys Ile
                515                 520                 525
Ser Glu Ala Val Glu Asp Val Ala Gly Ala Phe Gly Ala Arg Asn Val
    530                 535                 540
Pro Gln Ala Met Lys Val Val Glu Thr Met Gly Ile Ile Gln Gly Arg
545                 550                 555                 560
Lys Trp Asn Val Ala Gly Leu Asn Glu Phe Arg Lys His Phe His Leu
                565                 570                 575
Lys Pro Tyr Ser Thr Phe Glu Asp Ile Asn Ser Asp Pro Gly Val Ala
                580                 585                 590
Glu Ala Leu Arg Arg Leu Tyr Asp His Pro Asp Asn Val Glu Leu Tyr
                595                 600                 605
Pro Gly Leu Val Ala Glu Glu Asp Lys Gln Pro Met Val Pro Gly Val
                610                 615                 620
Gly Ile Ala Pro Thr Tyr Thr Ile Ser Arg Val Val Leu Ser Asp Ala
625                 630                 635                 640
Val Cys Leu Val Arg Gly Asp Arg Phe Tyr Thr Thr Asp Phe Thr Pro
                645                 650                 655
Arg Asn Leu Thr Asn Trp Gly Tyr Lys Glu Val Asp Tyr Asp Leu Ser
                660                 665                 670
Val Asn His Gly Cys Val Phe Tyr Lys Leu Phe Ile Arg Ala Phe Pro
                675                 680                 685
```

FIG. 1 - CONTINUED

```
Asn His Phe Lys Gln Asn Ser Val Tyr Ala His Tyr Pro Met Val Val
        690             695             700
Pro Ser Glu Asn Lys Arg Ile Leu Glu Ala Leu Gly Arg Ala Asp Leu
705             710             715                             720
Phe Asp Phe Glu Ala Pro Lys Tyr Ile Pro Pro Arg Val Asn Ile Thr
                725             730             735
Ser Tyr Gly Gly Ala Glu Tyr Ile Leu Glu Thr Gln Glu Lys Tyr Lys
            740             745             750
Val Thr Trp His Glu Gly Leu Gly Phe Leu Met Gly Glu Gly Gly Leu
            755             760             765
Lys Phe Met Leu Ser Gly Asp Asp Pro Leu His Ala Gln Gln Arg Lys
    770             775             780
Cys Met Ala Ala Gln Leu Tyr Lys Asp Gly Trp Thr Glu Ala Val Lys
785             790             795                             800
Ala Phe Tyr Ala Gly Met Met Glu Glu Leu Leu Val Ser Lys Ser Tyr
                805             810             815
Phe Leu Gly Asn Asn Lys His Arg His Val Asp Ile Ile Arg Asp Val
            820             825             830
Gly Asn Met Val His Val His Phe Ala Ser Gln Val Phe Gly Leu Pro
            835             840             845
Leu Lys Thr Ala Lys Asn Pro Thr Gly Val Phe Thr Glu Gln Glu Met
    850             855             860
Tyr Gly Ile Leu Ala Ala Ile Phe Thr Thr Ile Phe Phe Asp Leu Asp
865             870             875                             880
Pro Ser Lys Ser Phe Pro Leu Arg Thr Lys Thr Arg Glu Val Cys Gln
                885             890             895
Lys Leu Ala Lys Leu Val Glu Ala Asn Val Lys Leu Ile Asn Lys Ile
            900             905             910
Pro Trp Ser Arg Gly Met Phe Val Gly Lys Pro Ala Lys Asp Glu Pro
            915             920             925
Leu Ser Ile Tyr Gly Lys Thr Met Ile Lys Gly Leu Lys Ala His Gly
    930             935             940
Leu Ser Asp Tyr Asp Ile Ala Trp Ser His Val Val Pro Thr Ser Gly
945             950             955                             960
Ala Met Val Pro Asn Gln Ala Gln Val Phe Ala Gln Ala Val Asp Tyr
                965             970             975
Tyr Leu Ser Pro Ala Gly Met His Tyr Ile Pro Glu Ile His Met Val
            980             985             990
Ala Leu Gln Pro Ser Thr Pro Glu Thr Asp Ala Leu Leu Leu Gly Tyr
            995             1000            1005
Ala Met Glu Gly Ile Arg Leu Ala Gly Thr Phe Gly Ser Tyr Arg Glu
    1010            1015            1020
Ala Ala Val Asp Asp Val Val Lys Glu Asp Asn Gly Arg Gln Val Pro
1025            1030            1035            1040
Val Lys Ala Gly Asp Arg Val Phe Val Ser Phe Val Asp Ala Ala Arg
                1045            1050            1055
```

FIG. 1 - CONTINUED

```
Asp Pro Lys His Phe Pro Asp Pro Glu Val Val Asn Pro Arg Arg Pro
            1060                1065                1070
Ala Lys Lys Tyr Ile His Tyr Gly Val Gly Pro His Ala Cys Leu Gly
        1075                1080                1085
Arg Asp Ala Ser Gln Ile Ala Ile Thr Glu Met Phe Arg Cys Leu Phe
        1090                1095                1100
Arg Arg Arg Asn Val Arg Arg Val Pro Gly Pro Gln Gly Glu Leu Lys
1105                1110                1115                1120
Lys Val Pro Arg Pro Gly Gly Phe Tyr Val Tyr Met Arg Glu Asp Trp
                1125                1130                1135
Gly Gly Leu Phe Pro Phe Pro Val Thr Met Arg Val Met Trp Asp Asp
                1140                1145                1150
Glu
```

<210> 7
<211> 530
<212> PRT
<213> Fusarium oxysporum

<400> 7
```
Met Lys Gly Ser Ala Thr Leu Ala Phe Ala Leu Val Gln Phe Ser Ala
  1               5                  10                  15
Ala Ser Gln Leu Val Trp Pro Ser Lys Trp Asp Glu Val Glu Asp Leu
             20                  25                  30
Leu Tyr Met Gln Gly Gly Phe Asn Lys Arg Gly Phe Ala Asp Ala Leu
         35                  40                  45
Arg Thr Cys Glu Phe Gly Ser Asn Val Pro Gly Thr Gln Asn Thr Ala
     50                  55                  60
Glu Trp Leu Arg Thr Ala Phe His Asp Ala Ile Thr His Asp Ala Lys
 65                  70                  75                  80
Ala Gly Thr Gly Gly Leu Asp Ala Ser Ile Tyr Trp Glu Ser Ser Arg
                 85                  90                  95
Pro Glu Asn Pro Gly Lys Ala Phe Asn Asn Thr Phe Gly Phe Phe Ser
            100                 105                 110
Gly Phe His Asn Pro Arg Ala Thr Ala Ser Asp Leu Thr Ala Leu Gly
        115                 120                 125
Thr Val Leu Ala Val Gly Ala Cys Asn Gly Pro Arg Ile Pro Phe Arg
    130                 135                 140
Ala Gly Arg Ile Asp Ala Tyr Lys Ala Gly Pro Ala Gly Val Pro Glu
145                 150                 155                 160
Pro Ser Thr Asn Leu Lys Asp Thr Phe Ala Ala Phe Thr Lys Ala Gly
                165                 170                 175
Phe Thr Lys Glu Glu Met Thr Ala Met Val Ala Cys Gly His Ala Ile
            180                 185                 190
```

FIG. 1 - CONTINUED

```
Gly Gly Val His Ser Val Asp Phe Pro Glu Ile Val Gly Ile Lys Ala
            195                 200                 205
Asp Pro Asn Asn Asp Thr Asn Val Pro Phe Gln Lys Asp Val Ser Ser
        210                 215                 220
Phe His Asn Gly Ile Val Thr Glu Tyr Leu Ala Gly Thr Ser Lys Asn
225                 230                 235                 240
Pro Leu Val Ala Ser Lys Asn Ala Thr Phe His Ser Asp Lys Arg Ile
                245                 250                 255
Phe Asp Asn Asp Lys Ala Thr Met Lys Lys Leu Ser Thr Lys Ala Gly
                260                 265                 270
Phe Asn Ser Met Cys Ala Asp Ile Leu Thr Arg Met Ile Asp Thr Val
            275                 280                 285
Pro Lys Ser Val Gln Leu Thr Pro Val Leu Glu Ala Tyr Asp Val Arg
        290                 295                 300
Pro Tyr Ile Thr Glu Leu Ser Leu Asn Asn Lys Asn Lys Ile His Phe
305                 310                 315                 320
Thr Gly Ser Val Arg Val Arg Ile Thr Asn Asn Ile Arg Asp Asn Asn
                325                 330                 335
Asp Leu Ala Ile Asn Leu Ile Tyr Val Gly Arg Asp Gly Lys Lys Val
                340                 345                 350
Thr Val Pro Thr Gln Gln Val Thr Phe Gln Gly Gly Thr Ser Phe Gly
            355                 360                 365
Ala Gly Glu Val Phe Ala Asn Phe Glu Phe Asp Thr Thr Met Asp Ala
        370                 375                 380
Lys Asn Gly Ile Thr Lys Phe Phe Ile Gln Glu Val Lys Pro Ser Thr
385                 390                 395                 400
Lys Ala Thr Val Thr His Asp Asn Gln Lys Thr Gly Gly Tyr Lys Val
                405                 410                 415
Asp Asp Thr Val Leu Tyr Gln Leu Gln Gln Ser Cys Ala Val Leu Glu
            420                 425                 430
Lys Leu Pro Asn Ala Pro Leu Val Val Thr Ala Met Val Arg Asp Ala
        435                 440                 445
Arg Ala Lys Asp Ala Leu Thr Leu Arg Val Ala His Lys Lys Pro Val
    450                 455                 460
Lys Gly Ser Ile Val Pro Arg Phe Gln Thr Ala Ile Thr Asn Phe Lys
465                 470                 475                 480
Ala Thr Gly Lys Lys Ser Ser Gly Tyr Thr Gly Phe Gln Ala Lys Thr
                485                 490                 495
Met Phe Glu Glu Gln Ser Thr Tyr Phe Asp Ile Val Leu Gly Gly Ser
            500                 505                 510
Pro Ala Ser Gly Val Gln Phe Leu Thr Ser Gln Ala Met Pro Ser Gln
            515                 520                 525
Cys Ser
530
```

FIG. 1 - CONTINUED

```
<210> 8
<211> 358
<212> PRT
<213> Fusarium graminearum

<400> 8
Met Ala Ser Ala Thr Arg Gln Phe Ala Arg Ala Ala Thr Arg Ala Thr
 1               5                  10                  15
Arg Asn Gly Phe Ala Ile Ala Pro Arg Gln Val Ile Arg Gln Gln Gly
                20                  25                  30
Arg Arg Tyr Tyr Ser Ser Glu Pro Ala Gln Lys Ser Ser Ser Ala Trp
            35                  40                  45
Ile Trp Leu Thr Gly Ala Ala Val Ala Gly Gly Ala Gly Tyr Tyr Phe
        50                  55                  60
Tyr Gly Asn Ser Ala Ser Ser Ala Thr Ala Lys Val Phe Asn Pro Ser
65                  70                  75                  80
Lys Glu Asp Tyr Gln Lys Val Tyr Asn Glu Ile Ala Ala Arg Leu Glu
                85                  90                  95
Glu Lys Asp Asp Tyr Asp Asp Gly Ser Tyr Gly Pro Val Leu Val Arg
            100                 105                 110
Leu Ala Trp His Ala Ser Gly Thr Tyr Asp Lys Glu Thr Gly Thr Gly
        115                 120                 125
Gly Ser Asn Gly Ala Thr Met Arg Phe Ala Pro Glu Ser Asp His Gly
    130                 135                 140
Ala Asn Ala Gly Leu Ala Ala Arg Asp Phe Leu Gln Pro Val Lys
145                 150                 155                 160
Glu Lys Phe Pro Trp Ile Thr Tyr Ser Asp Leu Trp Ile Leu Ala Gly
                165                 170                 175
Val Cys Ala Ile Gln Glu Met Leu Gly Pro Ala Ile Pro Tyr Arg Pro
            180                 185                 190
Gly Arg Ser Asp Arg Asp Val Ser Gly Cys Thr Pro Asp Gly Arg Leu
        195                 200                 205
Pro Asp Ala Ser Lys Arg Gln Asp His Leu Arg Gly Ile Phe Gly Arg
    210                 215                 220
Met Gly Phe Asn Asp Gln Glu Ile Val Ala Leu Ser Gly Ala His Ala
225                 230                 235                 240
Leu Gly Arg Cys His Thr Asp Arg Ser Gly Tyr Ser Gly Pro Trp Thr
                245                 250                 255
Phe Ser Pro Thr Val Leu Thr Asn Asp Tyr Phe Arg Leu Leu Val Glu
            260                 265                 270
Glu Lys Trp Gln Trp Lys Lys Trp Asn Gly Pro Ala Gln Tyr Glu Asp
        275                 280                 285
Lys Ser Thr Lys Ser Leu Met Met Leu Pro Ser Asp Ile Ala Leu Ile
    290                 295                 300
Glu Asp Lys Lys Phe Lys Pro Trp Val Glu Lys Tyr Ala Lys Asp Asn
305                 310                 315                 320
```

FIG. 1 - CONTINUED

```
Asp Ala Phe Phe Lys Asp Phe Ser Asn Val Val Leu Arg Leu Phe Glu
                325             330                 335
Leu Gly Val Pro Phe Ala Gln Gly Thr Glu Asn Gln Arg Trp Thr Phe
            340             345                 350
Lys Pro Thr His Gln Glu
            355

<210> 9
<211> 122
<212> PRT
<213> Chlamydomonas eugametos

<400> 9
Met Ser Leu Phe Ala Lys Leu Gly Gly Arg Glu Ala Val Glu Ala Ala
1               5                   10                  15
Val Asp Lys Phe Tyr Asn Lys Ile Val Ala Asp Pro Thr Val Ser Thr
                20                  25                  30
Tyr Phe Ser Asn Thr Asp Met Lys Val Gln Arg Ser Lys Gln Phe Ala
            35                  40                  45
Phe Leu Ala Tyr Ala Leu Gly Gly Ala Ser Glu Trp Lys Gly Lys Asp
    50                  55                  60
Met Arg Thr Ala His Lys Asp Leu Val Pro His Leu Ser Asp Val His
65                  70                  75                  80
Phe Gln Ala Val Ala Arg His Leu Ser Asp Thr Leu Thr Glu Leu Gly
                85                  90                  95
Val Pro Pro Glu Asp Ile Thr Asp Ala Met Ala Val Val Ala Ser Thr
            100                 105                 110
Arg Thr Glu Val Leu Asn Met Pro Gln Gln
            115                 120

<210> 10
<211> 121
<212> PRT
<213> Tetrahymena pyriformis

<400> 10
Met Asn Lys Pro Gln Thr Ile Tyr Glu Lys Leu Gly Gly Glu Asn Ala
1               5                   10                  15
Met Lys Ala Ala Val Pro Leu Phe Tyr Lys Lys Val Leu Ala Asp Glu
                20                  25                  30
Arg Val Lys His Phe Phe Lys Asn Thr Asp Met Asp His Gln Thr Lys
            35                  40                  45
Gln Gln Thr Asp Phe Leu Thr Met Leu Leu Gly Gly Pro Asn His Tyr
    50                  55                  60
```

FIG. 1 - CONTINUED

```
Lys Gly Lys Asn Met Thr Glu Ala His Lys Gly Met Asn Leu Gln Asn
65                  70                  75                  80
Leu His Phe Asp Ala Ile Ile Glu Asn Leu Ala Ala Thr Leu Lys Glu
                85                  90                  95
Leu Gly Val Thr Asp Ala Val Ile Asn Glu Ala Ala Lys Val Ile Glu
                100                 105                 110
His Thr Arg Lys Asp Met Leu Gly Lys
            115                 120
```

<210> 11
<211> 117
<212> PRT
<213> Paramecium caudatum

<400> 11
```
Met Ser Leu Phe Glu Gln Leu Gly Gly Gln Ala Ala Val Gln Ala Val
1               5                   10                  15
Thr Ala Gln Phe Tyr Ala Asn Ile Gln Ala Asp Ala Thr Val Ala Thr
                20                  25                  30
Phe Phe Asn Gly Ile Asp Met Pro Asn Gln Thr Asn Lys Thr Ala Ala
                35                  40                  45
Phe Leu Cys Ala Ala Leu Gly Gly Pro Asn Ala Trp Thr Gly Arg Asn
            50                  55                  60
Leu Lys Glu Val His Ala Asn Met Gly Val Ser Asn Ala Gln Phe Thr
65                  70                  75                  80
Thr Val Ile Gly His Leu Arg Ser Ala Leu Thr Gly Ala Gly Val Ala
                85                  90                  95
Ala Ala Leu Val Glu Gln Thr Val Ala Val Ala Glu Thr Val Arg Gly
                100                 105                 110
Asp Val Val Thr Val
            115
```

<210> 12
<211> 147
<212> PRT
<213> Aspergillus niger

<400> 12
```
Met Pro Leu Thr Pro Glu Gln Ile Lys Ile Lys Ala Thr Val Pro
1               5                   10                  15
Val Leu Gln Glu Tyr Gly Thr Lys Ile Thr Thr Ala Phe Tyr Met Asn
                20                  25                  30
Met Ser Thr Val His Pro Glu Leu Asn Ala Val Phe Asn Thr Ala Asn
                35                  40                  45
```

FIG. 1 - CONTINUED

```
Gln Val Lys Gly His Gln Ala Arg Ala Leu Ala Gly Ala Leu Phe Ala
    50              55                  60
Tyr Ala Ser His Ile Asp Asp Leu Gly Ala Leu Gly Pro Ala Val Glu
65              70                  75                      80
Leu Ile Cys Asn Lys His Ala Ser Leu Tyr Ile Gln Ala Asp Glu Tyr
                85                  90                  95
Lys Ile Val Gly Lys Tyr Leu Leu Glu Ala Met Lys Glu Val Leu Gly
            100                 105                 110
Asp Ala Cys Thr Asp Asp Ile Leu Asp Ala Trp Gly Ala Ala Tyr Trp
            115                 120                 125
Ala Leu Ala Asp Ile Met Ile Asn Arg Glu Ala Ala Leu Tyr Lys Gln
    130                 135                 140
Ser Gln Gly
145
```

```
<210> 13
<211> 165
<212> PRT
<213> Zea mays

<400> 13
Met Ala Leu Ala Glu Ala Asp Asp Gly Ala Val Val Phe Gly Glu Glu
 1               5                  10                  15
Gln Glu Ala Leu Val Leu Lys Ser Trp Ala Val Met Lys Lys Asp Ala
            20                  25                  30
Ala Asn Leu Gly Leu Arg Phe Phe Leu Lys Val Phe Glu Ile Ala Pro
            35                  40                  45
Ser Ala Glu Gln Met Phe Ser Phe Leu Arg Asp Ser Asp Val Pro Leu
    50                  55                  60
Glu Lys Asn Pro Lys Leu Lys Thr His Ala Met Ser Val Phe Val Met
65                  70                  75                      80
Thr Cys Glu Ala Ala Ala Gln Leu Arg Lys Ala Gly Lys Val Thr Val
                85                  90                  95
Arg Glu Thr Thr Leu Lys Arg Leu Gly Ala Thr His Leu Arg Tyr Gly
            100                 105                 110
Val Ala Asp Gly His Phe Glu Val Thr Gly Phe Ala Leu Leu Glu Thr
            115                 120                 125
Ile Lys Glu Ala Leu Pro Ala Asp Met Trp Ser Leu Glu Met Lys Lys
    130                 135                 140
Ala Trp Ala Glu Ala Tyr Ser Gln Leu Val Ala Ala Ile Lys Arg Glu
145                 150                 155                 160
Met Lys Pro Asp Ala
                165
```

FIG. 1 - CONTINUED

```
<210> 14
<211> 169
<212> PRT
<213> Oryza sativa subsp. japonica

<400> 14
Met Ala Leu Val Glu Gly Asn Asn Gly Val Ser Gly Gly Ala Val Ser
 1               5                  10                  15
Phe Ser Glu Glu Gln Glu Ala Leu Val Leu Lys Ser Trp Ala Ile Met
                20                  25                  30
Lys Lys Asp Ser Ala Asn Ile Gly Leu Arg Phe Phe Leu Lys Ile Phe
                35                  40                  45
Glu Val Ala Pro Ser Ala Ser Gln Met Phe Ser Phe Leu Arg Asn Ser
            50                  55                  60
Asp Val Pro Leu Glu Lys Asn Pro Lys Leu Lys Thr His Ala Met Ser
65                  70                  75                  80
Val Phe Val Met Thr Cys Glu Ala Ala Gln Leu Arg Lys Ala Gly
                85                  90                  95
Lys Val Thr Val Arg Asp Thr Thr Leu Lys Arg Leu Gly Ala Thr His
                100                 105                 110
Phe Lys Tyr Gly Val Gly Asp Ala His Phe Glu Val Thr Arg Phe Ala
                115                 120                 125
Leu Leu Glu Thr Ile Lys Glu Ala Val Pro Val Asp Met Trp Ser Pro
            130                 135                 140
Ala Met Lys Ser Ala Trp Ser Glu Ala Tyr Asn Gln Leu Val Ala Ala
145                 150                 155                 160
Ile Lys Gln Glu Met Lys Pro Ala Glu
                    165

<210> 15
<211> 160
<212> PRT
<213> Arabidopsis thaliana

<400> 15
Met Glu Ser Glu Gly Lys Ile Val Phe Thr Glu Glu Gln Glu Ala Leu
 1               5                  10                  15
Val Val Lys Ser Trp Ser Val Met Lys Lys Asn Ser Ala Glu Leu Gly
                20                  25                  30
Leu Lys Leu Phe Ile Lys Ile Phe Glu Ile Ala Pro Thr Thr Lys Lys
                35                  40                  45
Met Phe Ser Phe Leu Arg Asp Ser Pro Ile Pro Ala Glu Gln Asn Pro
            50                  55                  60
Lys Leu Lys Pro His Ala Met Ser Val Phe Val Met Cys Cys Glu Ser
65                  70                  75                  80
```

FIG. 1 - CONTINUED

```
Ala Val Gln Leu Arg Lys Thr Gly Lys Val Thr Val Arg Glu Thr Thr
                85                  90                  95
Leu Lys Arg Leu Gly Ala Ser His Ser Lys Tyr Gly Val Val Asp Glu
            100                 105                 110
His Phe Glu Val Ala Lys Tyr Ala Leu Leu Glu Thr Ile Lys Glu Ala
            115                 120                 125
Val Pro Glu Met Trp Ser Pro Glu Met Lys Val Ala Trp Gly Gln Ala
            130                 135                 140
Tyr Asp His Leu Val Ala Ala Ile Lys Ala Glu Met Asn Leu Ser Asn
145                 150                 155                 160
```

<210> 16
<211> 147
<212> PRT
<213> Pisum sativum

<400> 16
```
Met Gly Phe Thr Asp Lys Gln Glu Ala Leu Val Asn Ser Ser Trp Glu
 1               5                  10                  15
Ser Phe Lys Gln Asn Leu Ser Gly Asn Ser Ile Leu Phe Tyr Thr Ile
            20                  25                  30
Ile Leu Glu Lys Ala Pro Ala Ala Lys Gly Leu Phe Ser Phe Leu Lys
            35                  40                  45
Asp Thr Ala Gly Val Glu Asp Ser Pro Lys Leu Gln Ala His Ala Glu
            50                  55                  60
Gln Val Phe Gly Leu Val Arg Asp Ser Ala Ala Gln Leu Arg Thr Lys
65                  70                  75                  80
Gly Glu Val Val Leu Gly Asn Ala Thr Leu Gly Ala Ile His Val Gln
                85                  90                  95
Arg Gly Val Thr Asp Pro His Phe Val Val Lys Glu Ala Leu Leu
            100                 105                 110
Gln Thr Ile Lys Lys Ala Ser Gly Asn Asn Trp Ser Glu Glu Leu Asn
            115                 120                 125
Thr Ala Trp Glu Val Ala Tyr Asp Gly Leu Ala Thr Ala Ile Lys Lys
            130                 135                 140
Ala Met Thr
145
```

<210> 17
<211> 145
<212> PRT
<213> Vigna unguiculata

FIG. 1 - CONTINUED

```
<400> 17
Met Val Ala Phe Ser Asp Lys Gln Glu Ala Leu Val Asn Gly Ala Tyr
1               5                   10                  15
Glu Ala Phe Lys Ala Asn Ile Pro Lys Tyr Ser Val Val Phe Tyr Thr
                20                  25                  30
Thr Ile Leu Glu Lys Ala Pro Ala Ala Lys Asn Leu Phe Ser Phe Leu
            35                  40                  45
Ala Asn Gly Val Asp Ala Thr Asn Pro Lys Leu Thr Gly His Ala Glu
        50                  55                  60
Lys Leu Phe Gly Leu Val Arg Asp Ser Ala Ala Gln Leu Arg Ala Ser
65                  70                  75                  80
Gly Gly Val Val Ala Asp Ala Ala Leu Gly Ala Val His Ser Gln Lys
                85                  90                  95
Ala Val Asn Asp Ala Gln Phe Val Val Val Lys Glu Ala Leu Val Lys
                100                 105                 110
Thr Leu Lys Glu Ala Val Gly Asp Lys Trp Ser Asp Glu Leu Gly Thr
            115                 120                 125
Ala Val Glu Leu Ala Tyr Asp Glu Leu Ala Ala Ala Ile Lys Lys Ala
        130                 135                 140
Tyr
145

<210> 18
<211> 154
<212> PRT
<213> Bos taurus

<400> 18
Met Gly Leu Ser Asp Gly Glu Trp Gln Leu Val Leu Asn Ala Trp Gly
1               5                   10                  15
Lys Val Glu Ala Asp Val Ala Gly His Gly Gln Glu Val Leu Ile Arg
                20                  25                  30
Leu Phe Thr Gly His Pro Glu Thr Leu Glu Lys Phe Asp Lys Phe Lys
            35                  40                  45
His Leu Lys Thr Glu Ala Glu Met Lys Ala Ser Glu Asp Leu Lys Lys
        50                  55                  60
His Gly Asn Thr Val Leu Thr Ala Leu Gly Gly Ile Leu Lys Lys Lys
65                  70                  75                  80
Gly His His Glu Ala Glu Val Lys His Leu Ala Glu Ser His Ala Asn
                85                  90                  95
Lys His Lys Ile Pro Val Lys Tyr Leu Glu Phe Ile Ser Asp Ala Ile
                100                 105                 110
Ile His Val Leu His Ala Lys His Pro Ser Asp Phe Gly Ala Asp Ala
            115                 120                 125
Gln Ala Ala Met Ser Lys Ala Leu Glu Leu Phe Arg Asn Asp Met Ala
        130                 135                 140
```

FIG. 1 - CONTINUED

```
Ala Gln Tyr Lys Val Leu Gly Phe His Gly
145                 150
```

```
<210> 19
<211> 154
<212> PRT
<213> Sus scrofa

<400> 19
Met Gly Leu Ser Asp Gly Glu Trp Gln Leu Val Leu Asn Val Trp Gly
  1               5                  10                  15
Lys Val Glu Ala Asp Val Ala Gly His Gly Gln Glu Val Leu Ile Arg
                 20                  25                  30
Leu Phe Lys Gly His Pro Glu Thr Leu Glu Lys Phe Asp Lys Phe Lys
                 35                  40                  45
His Leu Lys Ser Glu Asp Glu Met Lys Ala Ser Glu Asp Leu Lys Lys
         50                  55                  60
His Gly Asn Thr Val Leu Thr Ala Leu Gly Gly Ile Leu Lys Lys Lys
 65                  70                  75                  80
Gly His His Glu Ala Glu Leu Thr Pro Leu Ala Gln Ser His Ala Thr
                     85                  90                  95
Lys His Lys Ile Pro Val Lys Tyr Leu Glu Phe Ile Ser Glu Ala Ile
                100                 105                 110
Ile Gln Val Leu Gln Ser Lys His Pro Gly Asp Phe Gly Ala Asp Ala
                115                 120                 125
Gln Gly Ala Met Ser Lys Ala Leu Glu Leu Phe Arg Asn Asp Met Ala
            130                 135                 140
Ala Lys Tyr Lys Glu Leu Gly Phe Gln Gly
145                 150
```

```
<210> 20
<211> 154
<212> PRT
<213> Equus caballus

<400> 20
Met Gly Leu Ser Asp Gly Glu Trp Gln Gln Val Leu Asn Val Trp Gly
  1               5                  10                  15
Lys Val Glu Ala Asp Ile Ala Gly His Gly Gln Glu Val Leu Ile Arg
                 20                  25                  30
Leu Phe Thr Gly His Pro Glu Thr Leu Glu Lys Phe Asp Lys Phe Lys
                 35                  40                  45
His Leu Lys Thr Glu Ala Glu Met Lys Ala Ser Glu Asp Leu Lys Lys
         50                  55                  60
```

FIG. 1 - CONTINUED

```
His Gly Thr Val Val Leu Thr Ala Leu Gly Gly Ile Leu Lys Lys Lys
 65                  70                  75                  80
Gly His His Glu Ala Glu Leu Lys Pro Leu Ala Gln Ser His Ala Thr
                 85                  90                  95
Lys His Lys Ile Pro Ile Lys Tyr Leu Glu Phe Ile Ser Asp Ala Ile
                100                 105                 110
Ile His Val Leu His Ser Lys His Pro Gly Asp Phe Gly Ala Asp Ala
            115                 120                 125
Gln Gly Ala Met Thr Lys Ala Leu Glu Leu Phe Arg Asn Asp Ile Ala
        130                 135                 140
Ala Lys Tyr Lys Glu Leu Gly Phe Gln Gly
145                 150

<210> 21
<211> 152
<212> PRT
<213> Nicotiana benthamiana

<400> 21
Met Ser Ser Phe Thr Glu Glu Gln Glu Ala Leu Val Val Lys Ser Trp
  1               5                  10                  15
Asp Ser Met Lys Lys Asn Ala Gly Glu Trp Gly Leu Lys Leu Phe Leu
                 20                  25                  30
Lys Ile Phe Glu Ile Ala Pro Ser Ala Lys Lys Leu Phe Ser Phe Leu
                 35                  40                  45
Lys Asp Ser Asn Val Pro Leu Glu Gln Asn Ala Lys Leu Lys Pro His
             50                  55                  60
Ser Lys Ser Val Phe Val Met Thr Cys Glu Ala Ala Val Gln Leu Arg
 65                  70                  75                  80
Lys Ala Gly Lys Val Val Val Arg Asp Ser Thr Leu Lys Lys Leu Gly
                 85                  90                  95
Ala Thr His Phe Lys Tyr Gly Val Ala Asp Glu His Phe Glu Val Thr
                100                 105                 110
Lys Phe Ala Leu Leu Glu Thr Ile Lys Glu Ala Val Pro Glu Met Trp
            115                 120                 125
Ser Val Asp Met Lys Asn Ala Trp Gly Glu Ala Phe Asp Gln Leu Val
        130                 135                 140
Asn Ala Ile Lys Thr Glu Met Lys
145                 150

<210> 22
<211> 132
<212> PRT
<213> Bacillus subtilis
```

FIG. 1 - CONTINUED

```
<400> 22
Met Gly Gln Ser Phe Asn Ala Pro Tyr Glu Ala Ile Gly Glu Glu Leu
1               5                   10                  15
Leu Ser Gln Leu Val Asp Thr Phe Tyr Glu Arg Val Ala Ser His Pro
                20                  25                  30
Leu Leu Lys Pro Ile Phe Pro Ser Asp Leu Thr Glu Thr Ala Arg Lys
            35                  40                  45
Gln Lys Gln Phe Leu Thr Gln Tyr Leu Gly Gly Pro Pro Leu Tyr Thr
        50                  55                  60
Glu Glu His Gly His Pro Met Leu Arg Ala Arg His Leu Pro Phe Pro
65                  70                  75                  80
Ile Thr Asn Glu Arg Ala Asp Ala Trp Leu Ser Cys Met Lys Asp Ala
                85                  90                  95
Met Asp His Val Gly Leu Glu Gly Glu Ile Arg Glu Phe Leu Phe Gly
                100                 105                 110
Arg Leu Glu Leu Thr Ala Arg His Met Val Asn Gln Thr Glu Ala Glu
            115                 120                 125
Asp Arg Ser Ser
        130

<210> 23
<211> 131
<212> PRT
<213> Corynebacterium glutamicum

<400> 23
Met Thr Thr Ser Glu Asn Phe Tyr Asp Ser Val Gly Gly Glu Glu Thr
1               5                   10                  15
Phe Ser Leu Ile Val His Arg Phe Tyr Glu Gln Val Pro Asn Asp Asp
                20                  25                  30
Ile Leu Gly Pro Met Tyr Pro Pro Asp Asp Phe Glu Gly Ala Glu Gln
            35                  40                  45
Arg Leu Lys Met Phe Leu Ser Gln Tyr Trp Gly Gly Pro Lys Asp Tyr
        50                  55                  60
Gln Glu Gln Arg Gly His Pro Arg Leu Arg Met Arg His Val Asn Tyr
65                  70                  75                  80
Pro Ile Gly Val Thr Ala Ala Glu Arg Trp Leu Gln Leu Met Ser Asn
                85                  90                  95
Ala Leu Asp Gly Val Asp Leu Thr Ala Glu Gln Arg Glu Ala Ile Trp
                100                 105                 110
Glu His Met Val Arg Ala Ala Asp Met Leu Ile Asn Ser Asn Pro Asp
            115                 120                 125
Pro His Ala
        130
```

FIG. 1 - CONTINUED

<210> 24
<211> 124
<212> PRT
<213> Synechocystis sp.

<400> 24
Met Ser Thr Leu Tyr Glu Lys Leu Gly Gly Thr Thr Ala Val Asp Leu
1               5                   10                  15
Ala Val Asp Lys Phe Tyr Glu Arg Val Leu Gln Asp Asp Arg Ile Lys
            20                  25                  30
His Phe Phe Ala Asp Val Asp Met Ala Lys Gln Arg Ala His Gln Lys
        35                  40                  45
Ala Phe Leu Thr Tyr Ala Phe Gly Gly Thr Asp Lys Tyr Asp Gly Arg
    50                  55                  60
Tyr Met Arg Glu Ala His Lys Glu Leu Val Glu Asn His Gly Leu Asn
65                  70                  75                  80
Gly Glu His Phe Asp Ala Val Ala Glu Asp Leu Leu Ala Thr Leu Lys
                85                  90                  95
Glu Met Gly Val Pro Glu Asp Leu Ile Ala Glu Val Ala Ala Val Ala
            100                 105                 110
Gly Ala Pro Ala His Lys Arg Asp Val Leu Asn Gln
        115                 120

<210> 25
<211> 183
<212> PRT
<213> Synechococcus sp.

<400> 25
Met Asp Val Ala Leu Leu Glu Lys Ser Phe Glu Gln Ile Ser Pro Arg
1               5                   10                  15
Ala Ile Glu Phe Ser Ala Ser Phe Tyr Gln Asn Leu Phe His His His
            20                  25                  30
Pro Glu Leu Lys Pro Leu Phe Ala Glu Thr Ser Gln Thr Ile Gln Glu
        35                  40                  45
Lys Lys Leu Ile Phe Ser Leu Ala Ala Ile Ile Glu Asn Leu Arg Asn
    50                  55                  60
Pro Asp Ile Leu Gln Pro Ala Leu Lys Ser Leu Gly Ala Arg His Ala
65                  70                  75                  80
Glu Val Gly Thr Ile Lys Ser His Tyr Pro Leu Val Gly Gln Ala Leu
                85                  90                  95
Ile Glu Thr Phe Ala Glu Tyr Leu Ala Ala Asp Trp Thr Glu Gln Leu
            100                 105                 110
Ala Thr Ala Trp Val Glu Ala Tyr Asp Val Ile Ala Ser Thr Met Ile
        115                 120                 125

FIG. 1 - CONTINUED

```
Glu Gly Ala Asp Asn Pro Ala Ala Tyr Leu Glu Pro Glu Leu Thr Phe
        130                 135                 140
Tyr Glu Trp Leu Asp Leu Tyr Gly Glu Glu Ser Pro Lys Val Arg Asn
145                 150                 155                 160
Ala Ile Ala Thr Leu Thr His Phe His Tyr Gly Glu Asp Pro Gln Asp
                165                 170                 175
Val Gln Arg Asp Ser Arg Gly
            180
```

<210> 26
<211> 118
<212> PRT
<213> Nostoc commune

<400> 26
```
Met Ser Thr Leu Tyr Asp Asn Ile Gly Gly Gln Pro Ala Ile Glu Gln
 1               5                  10                  15
Val Val Asp Glu Leu His Lys Arg Ile Ala Thr Asp Ser Leu Leu Ala
                20                  25                  30
Pro Val Phe Ala Gly Thr Asp Met Val Lys Gln Arg Asn His Leu Val
                35                  40                  45
Ala Phe Leu Ala Gln Ile Phe Glu Gly Pro Lys Gln Tyr Gly Gly Arg
            50                  55                  60
Pro Met Asp Lys Thr His Ala Gly Leu Asn Leu Gln Gln Pro His Phe
65                  70                  75                  80
Asp Ala Ile Ala Lys His Leu Gly Glu Arg Met Ala Val Arg Gly Val
                85                  90                  95
Ser Ala Glu Asn Thr Lys Ala Ala Leu Asp Arg Val Thr Asn Met Lys
                100                 105                 110
Gly Ala Ile Leu Asn Lys
            115
```

<210> 27
<211> 136
<212> PRT
<213> Bacillus megaterium

<400> 27
```
Met Arg Glu Lys Ile His Ser Pro Tyr Glu Leu Leu Gly Gly Glu His
 1               5                  10                  15
Thr Ile Ser Lys Leu Val Asp Ala Phe Tyr Thr Arg Val Gly Gln His
                20                  25                  30
Pro Glu Leu Ala Pro Ile Phe Pro Asp Asn Leu Thr Glu Thr Ala Arg
            35                  40                  45
```

FIG. 1 - CONTINUED

```
Lys Gln Lys Gln Phe Leu Thr Gln Tyr Leu Gly Gly Pro Ser Leu Tyr
    50                  55                  60
Thr Glu Glu His Gly His Pro Met Leu Arg Ala Arg His Leu Pro Phe
65                  70                  75                  80
Glu Ile Thr Pro Ser Arg Ala Lys Ala Trp Leu Thr Cys Met His Glu
                85                  90                  95
Ala Met Asp Glu Ile Asn Leu Glu Gly Pro Glu Arg Asp Glu Leu Tyr
            100                 105                 110
His Arg Leu Ile Leu Thr Ala Gln His Met Ile Asn Ser Pro Glu Gln
            115                 120                 125
Thr Asp Glu Lys Gly Phe Ser His
        130                 135
```

FIG. 2

SEQ ID NO. 28: Wild-type pAOX1

```
  1 AACATCCAAA GACGAAAGGT TGAATGAAAC CTTTTTGCCA TCCGACATCC ACAGGTCCAT
 61 TCTCACACAT AAGTGCCAAA CGCAACAGGA GGGGATACAC TAGCAGCAGA CCGTTGCAAA
121 CGCAGGACCT CCACTCCTCT TCTCCTCAAC ACCCACTTTT GCCATCGAAA AACCAGCCCA
181 GTTATTGGGC TTGATTGGAG CTCGCTCATT CCAATTCCTT CTATTAGGCT ACTAACACCA
241 TGACTTTATT AGCCTGTCTA TCCTGGCCCC CCTGGCGAGG TTCATGTTTG TTTATTTCCG
301 AATGCAACAA GCTCCGCATT ACACCCGAAC ATCACTCCAG ATGAGGGCTT TCTGAGTGTG
361 GGGTCAAATA GTTTCATGTT CCCCAAATGG CCCAAAACTG ACAGTTTAAA CGCTGTCTTG
421 GAACCTAATA TGACAAAAGC GTGATCTCAT CCAAGATGAA CTAAGTTTGG TTCGTTGAAA
481 TGCTAACGGC CAGTTGGTCA AAAAGAAACT TCCAAAAGTC GGCATACCGT TTGTCTTGTT
541 TGGTATTGAT TGACGAATGC TCAAAAATAA TCTCATTAAT GCTTAGCGCA GTCTCTCTAT
601 CGCTTCTGAA CCCCGGTGCA CCTGTGCCGA AACGCAAATG GGGAAACACC CGCTTTTTGG
661 ATGATTATGC ATTGTCTCCA CATTGTATGC TTCCAAGATT CTGGTGGGAA TACTGCTGAT
721 AGCCTAACGT TCATGATCAA AATTTAACTG TTCTAACCCC TACTTGACAG CAATATATAA
781 ACAGAAGGAA GCTGCCCTGT CTTAAACCTT TTTTTTTATC ATCATTATTA GCTTACTTTC
841 ATAATTGCGA CTGGTTCCAA TTGACAAGCT TTTGATTTTA ACGACTTTTA ACGACAACTT
901 GAGAAGATCA AAAACAACT AATTATTCGA AAC
```

SEQ ID NO. 29: Mutant pAOX1

```
  1 AACATCCAAA GACGAAAGGT TGAATGAAAC CTTTTTGCCA TCCGACATCC ACAGGTCCAT
 61 TCTCACACAT AAGTGCCAAA CGCAACAGGA GGGGATACAC TAGCAGCAGA CCGTTGCAAA
121 CGCAGGACCT CCACTCCTCT TCTCCCCAAC ACCTACTTTT GCCATCGAAA AACCAGCCCA
181 GTTATTGGGC TTGATTGGAG CTCGCTCATT CCAATTCCTT CTATTAGGCT ACTAACACCA
241 TGACTTTATT AGCCTGTCTA TCCTGGCCCC CCTGGCGAGG TTCATGTTTG TTTATTTCCG
301 AACGCAACAA GCTCCGCATT ACACCCGAAC ATCACTCCAG ATGAGGGCTT TCTGAGTGTG
361 GGGTCAAATA GTTTCATGTT CCCCAAATGG CCCAAAACTG ACAGTTTAAA CGCTGTCTTG
421 GAACCAAATA TGTCGAAAGC GTGATCTCAT CCAAGATGAA CTAAGTTTGG TTCGTTGAAA
481 TGCTAACGGC CAGTTGGTCA AAAAGAAACT TCCAAAAGTC GGCATACCGA TTGTCTTGTT
541 TGGTATTGAT TGACGAATGC TCAAAAATAA TTTCATTAAT GCTTAGCGCA GTCTCCCTAT
601 CGCTTCTGAA CCCCGGCGCA CCTGTGCCGA AACGCAAATG GGGAAACACC CGCTTTTTGG
661 ATGATTATGC ATTGTCTCCA CATTGTACGC TTCCATGATT CCGGTGGGGA TGCGGCTGAT
721 AGCCTAACGT TCATGATCAA AATTTAACTG TTCTAACCCC TACTTGACAG CAATATATAA
781 ACAGAAGGAG GCTGCCCTGT CTTAAACCTT TTTTTTTATC ATCATTATTA GCTTACTTTC
841 TTAATTGCGA CTGGTTCCAA TAGACAAGCT TTTGATTTTA ACGACTTTTA ACGACAACTT
901 GAGAAGATCA AAAACAACT AATTATTCGA AAC
```

| Original Sequence | TCCACATTGTATGCTTCCAAGATTCTGGTGGGAATACTGCTGA |
|---|---|
| pAOX1 MxG0038 | TCCACATTGTACCGCTTCCATGGATTCCCGGTGGGATGCCGCTGA |
| MxG0220 (t688c_a696t...) | TCCACATTGTACCGCTTCCATGGATTCCCGGTGGGATGCCGCTGA |

SEQ ID NO: 30
GAGGGTCTCGGATGACAGCTTTAACTGAAGGGGCC

SEQ ID NO: 31
GAGGGTCTCGATTATTGGTAAGTGTCGAGATCAACTGCC

SEQ ID NO: 32
GTGCTAGGATCCAACATCCAAAGACG

SEQ ID NO: 33
TTTTTCTAGAACCTTATCAAGATAGCTAGAAATAGAAATGGTTGC

SEQ ID NO: 34
TCCTGCAGCCCGGGGGATCCAACATCCAAAGA

SEQ ID NO: 35
CTTCAGTTAAAGCTGTCATCGTTTCGAATAATTAGT

SEQ ID NO: 36
AACAACTAATTATTCGAAACGATGACAGCTTTAACT

SEQ ID NO: 37
ACCTTTCGTCTTTGGATGTTGGATCCCCCGGG

MATERIALS AND METHODS FOR PROTEIN PRODUCTION

CROSS-REFERENCE TO RELATED APPLICATIONS

This application is a divisional of U.S. application Ser. No. 16/852,232, filed on Apr. 17, 2020, which claims priority to U.S. Provisional Application Ser. No. 62/835,338, filed on Apr. 17, 2019, both of which are incorporated by reference herein in their entirety.

DESCRIPTION OF THE TEXT FILE SUBMITTED ELECTRONICALLY

This application contains a Sequence Listing that has been submitted electronically as an XML file named "38767-0193002SL.XML". The XML file, created on Jul. 13, 2022, is 43,792 bytes in size. The material in the XML file is hereby incorporated by reference in its entirety.

TECHNICAL FIELD

This disclosure generally relates to DNA constructs and methods of using such DNA constructs to genetically engineer cells, such as yeast cells or methylotrophic yeast cells.

BACKGROUND

Recombinant expression of products is a common method to produce said products. In some cases, proteins can be produced by recombinant production. Constructs that can be used to efficiently express one or more products (e.g., proteins) in a cell, such as a yeast cell or a methylotrophic yeast cell, are provided herein.

SUMMARY

This document is based, at least in part, on the identification of point mutations in the AOX1 promoter that can confer increased expression of linked coding sequences. The mutated AOX1 promoters described herein can be used for efficient expression of operably linked coding sequences in *Pichia*, for example.

In one aspect, provided herein is a nucleic acid construct comprising a first alcohol oxidase promoter element, wherein the first alcohol oxidase promoter element includes a mutation at one or more nucleotide positions corresponding to any of nucleotide positions 668-734 relative to SEQ ID NO: 28.

Implementations can have one or more of the following features. The first alcohol oxidase promoter element can include a mutation at one or more nucleotide positions corresponding to any of nucleotide positions 673-729 relative to SEQ ID NO: 28. The first alcohol oxidase promoter element can include a mutation at one or more nucleotide positions corresponding to any of nucleotide positions 678-724 relative to SEQ ID NO: 28. The first alcohol oxidase promoter element can include a mutation at one or more nucleotide positions corresponding to any of nucleotide positions 683-719 relative to SEQ ID NO: 28. The first alcohol oxidase promoter element can include a mutation at one or more nucleotide positions corresponding to any of nucleotide positions 688-714 relative to SEQ ID NO: 28. The first alcohol oxidase promoter element can include two or more mutations at nucleotide positions corresponding to any of nucleotide positions 668-734 relative to SEQ ID NO: 28. The first alcohol oxidase promoter element can include three or more mutations at nucleotide positions corresponding to any of nucleotide positions 668-734 relative to SEQ ID NO: 28. The first alcohol oxidase promoter element can include four or more mutations at nucleotide positions corresponding to any of nucleotide positions 668-734 relative to SEQ ID NO: 28. The first alcohol oxidase promoter element can include five or more mutations at nucleotide positions corresponding to any of nucleotide positions 668-734 relative to SEQ ID NO: 28.

In another aspect, provided herein is a nucleic acid construct comprising a first alcohol oxidase promoter element, wherein the first alcohol oxidase promoter element can include one or more mutations at a nucleotide position selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Implementations can include one or more of the following features. The first alcohol oxidase promoter element can include two or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28. The first alcohol oxidase promoter element can include three or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28. The first alcohol oxidase promoter element can include four or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28. The first alcohol oxidase promoter element can include five or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28. The first alcohol oxidase promoter element can include one or more mutations at a nucleotide position selected from the group consisting of nucleotide positions corresponding to T688, A696, T702, A712, and T714 relative to SEQ ID NO: 28. The first alcohol oxidase promoter element can include two or more mutations at nucleotide positions selected from the group consisting of nucleotide positions corresponding to T688, A696, T702, A712, and T714 relative to SEQ ID NO: 28. The first alcohol oxidase promoter element can include three or more mutations at nucleotide positions selected from the group consisting of nucleotide positions corresponding to T688, A696, T702, A712, and T714 relative to SEQ ID NO: 28. The first alcohol oxidase promoter element can include four or more mutations at nucleotide positions selected from the group consisting of nucleotide positions corresponding to T688, A696, T702, A712, and T714 relative to SEQ ID NO: 28. The first alcohol oxidase promoter element can include mutations at nucleotide positions corresponding to T688, A696, T702, A712, and T714 relative to SEQ ID NO: 28.

In another aspect, provided herein is a nucleic acid construct comprising a first alcohol oxidase promoter element, wherein the first alcohol oxidase promoter element can include one or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Implementations can include one or more of the following features. The first alcohol oxidase promoter element can include two or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. The first alcohol oxidase promoter element can include three or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. The first alcohol oxidase promoter element can include four or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. The first alcohol oxidase promoter element can include five or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. The first alcohol oxidase promoter element can include one or more mutations selected from the group consisting of T688C, A696T, T702C, A712G, and T714G relative to SEQ ID NO: 28. The first alcohol oxidase promoter element can include two or more mutations selected from the group consisting of T688C, A696T, T702C, A712G, and T714G relative to SEQ ID NO: 28. The first alcohol oxidase promoter element can include three or more mutations selected from the group consisting of T688C, A696T, T702C, A712G, and T714G relative to SEQ ID NO: 28. The first alcohol oxidase promoter element can include four or more mutations selected from the group consisting of T688C, A696T, T702C, A712G, and T714G relative to SEQ ID NO: 28. The first alcohol oxidase promoter element can include the mutations T688C, A696T, T702C, A712G, and T714G relative to SEQ ID NO: 28.

Implementations of any of the nucleic acid constructs described herein can have one or more of the following features. The first alcohol oxidase promoter element can be an alcohol oxidase 1 promoter element. The first alcohol oxidase promoter element can have at least 90% sequence identity to SEQ ID NO: 28. The first alcohol oxidase promoter element can have at least 95% sequence identity to SEQ ID NO: 28. The nucleic acid construct can further include a nucleotide sequence encoding a first protein, wherein the nucleotide sequence encoding the first protein is operably linked to the first alcohol oxidase promoter element. The first protein can be exogenous to a methylotrophic yeast cell. The first protein can be heterologous to a methylotrophic yeast cell. The first protein can be selected from the group consisting of an antibody or fragment thereof, an enzyme, a regulatory protein, a peptide hormone, a blood clotting protein, a cytokine, a cytokine inhibitor, and a heme-binding protein. The first protein can be a heme-binding protein. The heme-binding protein can be selected from the group consisting of a globin, a cytochrome, a cytochrome c oxidase, a ligninase, a catalase, and a peroxidase. The heme-binding protein can be selected from the group consisting of an androglobin, a chlorocruorin, a cytoglobin, an erythrocruorin, a flavohemoglobin, a globin E, a globin X, a globin Y, a hemoglobin, a histoglobin, a leghemoglobin, a myoglobin, a neuroglobin, a non-symbiotic hemoglobin, a protoglobin, and a truncated hemoglobin. The heme-binding protein can be a non-symbiotic hemoglobin. The heme-binding protein can be a leghemoglobin. The heme-binding protein can include an amino acid sequence having at least 90% sequence identity to the amino acid sequence of any of SEQ ID NOs: 1-27. The first alcohol oxidase promoter element can include a recognition sequence for a transcription factor.

In another aspect, also provided herein is a methylotrophic yeast cell comprising a first nucleic acid construct, wherein the first nucleic acid construct is any nucleic acid construct described herein.

Implementations can have one or more of the following features. The methylotrophic yeast cell can be a *Pichia* cell, a *Candida* cell, a *Hansenula* cell, or a *Torulopsis* cell. The methylotrophic yeast cell can be a *Pichia methanolica* cell, a *Pichia pastoris* cell, a *Candida boidinii* cell, or a *Hansenula polymorpha* cell. The methylotrophic yeast cell can be a *Pichia pastoris* cell. The methylotrophic yeast cell can further include a second nucleic acid construct including a nucleotide sequence encoding a second protein, wherein the nucleotide sequence encoding the second protein is operably linked to the first alcohol oxidase promoter element or to a second promoter element. The nucleotide sequence encoding the second protein can be operably linked to a second promoter element that has the same sequence as the first alcohol oxidase promoter element. The second protein can be a transcription factor. The nucleotide sequence encoding the second protein can be operably linked to a second promoter element that can include a recognition sequence for the transcription factor. The first alcohol oxidase promoter element can include a recognition sequence for the transcription factor. The second protein can be a protein involved in heme biosynthesis. The protein involved in heme biosynthesis can be selected from the group consisting of aminolevulinic acid synthase (ALAS), δ-aminolevulinic acid dehydratase (ALAD), porphogilinogen deaminase (PBGD), uroporphyrinogen III synthase (UPG3S), uroporphyrinogen III decarboxylase (UPG3D), coprotoporphyrinogen oxidase (COPROX), protoporphyrinogen IX oxidase (PROTOX), and ferrochelatase (FC).

In another aspect, provided herein is a method of producing a protein in a methylotrophic yeast cell including expressing a nucleic acid construct including a nucleotide sequence encoding a first protein operably linked to a first alcohol oxidase promoter element, wherein the first alcohol oxidase promoter element includes a mutation at one or more nucleotide positions corresponding to any of nucleotide positions 668-734 relative to SEQ ID NO: 28.

Implementations can include one or more of the following features. The first alcohol oxidase promoter element can include a mutation at one or more nucleotide positions corresponding to any of nucleotide positions 673-729 relative to SEQ ID NO: 28. The first alcohol oxidase promoter element can include a mutation at one or more nucleotide positions corresponding to any of nucleotide positions 678-724 relative to SEQ ID NO: 28. The first alcohol oxidase promoter element can include a mutation at one or more nucleotide positions corresponding to any of nucleotide positions 683-719 relative to SEQ ID NO: 28. The first alcohol oxidase promoter element can include a mutation at one or more nucleotide positions corresponding to any of nucleotide positions 688-714 relative to SEQ ID NO: 28. The first alcohol oxidase promoter element can include two or more mutations at nucleotide positions corresponding to any of nucleotide positions 668-734 relative to SEQ ID NO: 28. The first alcohol oxidase promoter element can include three or more mutations at nucleotide positions corresponding to any of nucleotide positions 668-734 relative to SEQ ID NO: 28. The first alcohol oxidase promoter element can include four or more mutations at nucleotide positions corresponding to any of nucleotide positions 668-734 relative to SEQ ID NO: 28. The first alcohol oxidase promoter element can include five or more mutations at nucleotide positions corresponding to any of nucleotide positions 668-734 relative to SEQ ID NO: 28.

In another aspect, also provided herein is a method of producing a protein in a methylotrophic yeast cell including expressing a nucleic acid construct including a nucleotide sequence encoding a first protein operably linked to a first alcohol oxidase promoter element, wherein the first alcohol oxidase promoter element includes one or more mutations at a nucleotide position selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Implementations can include one or more of the following features. The first alcohol oxidase promoter element can include two or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28. The first alcohol oxidase promoter element can include three or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28. The first alcohol oxidase promoter element can include four or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28. The first alcohol oxidase promoter element can include five or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28. The first alcohol oxidase promoter element can include one or more mutations at a nucleotide position selected from the group consisting of nucleotide positions corresponding to of T688, A696, T702, A712, and T714 relative to SEQ ID NO: 28. The first alcohol oxidase promoter element can include two or more mutations at nucleotide positions selected from the group consisting of nucleotide positions corresponding to of T688, A696, T702, A712, and T714 relative to SEQ ID NO: 28. The first alcohol oxidase promoter element can include three or more mutations at nucleotide positions selected from the group consisting of nucleotide positions corresponding to of T688, A696, T702, A712, and T714 relative to SEQ ID NO: 28. The first alcohol oxidase promoter element can include four or more mutations at nucleotide positions selected from the group consisting of nucleotide positions corresponding to of T688, A696, T702, A712, and T714 as compared to SEQ ID NO: 28. The first alcohol oxidase promoter element can include mutations at nucleotide positions corresponding to T688, A696, T702, A712, and T714 as compared to SEQ ID NO: 28.

In another aspect, provided herein is a method of producing a protein in a methylotrophic yeast cell including expressing a nucleic acid construct including a nucleotide sequence encoding a first protein operably linked to a first alcohol oxidase promoter element, wherein the first alcohol oxidase promoter element includes one or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Implementations can include one or more of the following features. The first alcohol oxidase promoter element can include two or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. The first alcohol oxidase promoter element can include three or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. The first alcohol oxidase promoter element can include four or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. The first alcohol oxidase promoter element can include five or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. The first alcohol oxidase promoter element can include two or more mutations selected from the group consisting of T688C, A696T, T702C, A712G, and T714G relative to SEQ ID NO: 28. The first alcohol oxidase promoter element can include three or more mutations selected from the group consisting of T688C, A696T, T702C, A712G, and T714G relative to SEQ ID NO: 28. The first alcohol oxidase promoter element can include four or more mutations selected from the group consisting of T688C, A696T, T702C, A712G, and T714G relative to SEQ ID NO: 28. The first alcohol oxidase promoter element can include the mutations T688C, A696T, T702C, A712G, and T714G relative to SEQ ID NO: 28.

Implementations of any of the methods described herein can have one or more of the following features. The first alcohol oxidase promoter element can be an alcohol oxidase 1 promoter element. The first alcohol oxidase promoter element can have at least 90% sequence identity to SEQ ID NO: 28. The first alcohol oxidase promoter element can have at least 95% sequence identity to SEQ ID NO: 28. The first protein can be exogenous to the methylotrophic yeast cell. The first protein can be heterologous to the methylotrophic yeast cell. The first protein can be selected from the group consisting of an antibody or fragment thereof, an enzyme, a regulatory protein, a peptide hormone, a blood clotting protein, a cytokine, and a heme-binding protein. The first protein can be a heme-binding protein. The heme-binding protein can be selected from the group consisting of a globin, a cytochrome, a cytochrome c oxidase, a ligninase, a catalase, and a peroxidase. The heme-binding protein an be selected from the group consisting of an androglobin, a chlorocruorin, a cytoglobin, an erythrocruorin, a flavohemoglobin, a globin E, a globin X, a globin Y, a hemoglobin, a histoglobin, a leghemoglobin, a myoglobin, a neuroglobin, a non-symbiotic hemoglobin, a protoglobin, and a truncated hemoglobin. The heme-binding protein can be a non-symbiotic hemoglobin. The heme-binding protein can be a leghemoglobin. The heme-binding protein can include an amino acid sequence having at least 90% sequence identity to an amino acid sequence in any one of SEQ ID NOs: 1-27. The first alcohol oxidase promoter element can contain one or more recognition sequences for a transcription factor. The method can further include expressing a second nucleic acid construct including a nucleotide sequence encoding a second protein, wherein the nucleotide sequence encoding the second protein is operably linked to the first alcohol oxidase promoter element or to a second promoter element. The nucleotide sequence encoding the second protein can be operably linked to a second promoter element that has the same sequence as the first alcohol oxidase promoter element. The second protein can be a transcription factor. The nucleotide sequence encoding the second protein can be operably linked to a second promoter element that can include a recognition sequence for the transcription factor. The first alcohol oxidase promoter element can include a recognition sequence for the transcription factor. The second protein can be a protein involved in heme biosynthesis. The protein involved in heme biosynthesis can be selected from the group consisting of ALAS, ALAD, PBGD, UPG3S, UPG3D, COPROX, PROTOX, and FC. The method can be carried out in the absence of added methanol.

In another aspect, provided herein is a *Pichia pastoris* cell including a nucleic acid construct comprising a nucleotide sequence encoding a first alcohol oxidase promoter element, wherein the first alcohol oxidase promoter element includes one or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. In some embodiments, the one or more mutations can be selected from the group consisting of mutations corresponding to T688C, A696T, T702C, A712G, and T714G relative to SEQ ID NO: 28.

In another aspect, also provided herein is a method of producing leghemoglobin, the method including expressing a nucleic acid construct including a nucleotide sequence encoding leghemoglobin operably linked to a first alcohol oxidase promoter element, wherein the first alcohol oxidase promoter element includes one or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. In some embodiments, the method can be carried out in the absence of added methanol. In some embodiments, the one or more mutations can be selected from the group consisting of mutations corresponding to T688C, A696T, T702C, A712G, and T714G relative to SEQ ID NO: 28.

In another aspect, provided herein is a *Pichia pastoris* cell including a first nucleic acid construct including a nucleotide sequence with at least 90% sequence identity to SEQ ID NO: 28, wherein the first nucleic acid construct includes one or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. In some embodiments, the one or more mutations can be selected from the group consisting of mutations corresponding to T688C, A696T, T702C, A712G, and T714G relative to SEQ ID NO: 28.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF THE DRAWINGS

FIG. 1 provides the sequences of exemplary heme-binding proteins (SEQ ID NOs: 1-27).

FIG. 2 provides the sequences of pAOX1 wild-type and mutant sequences (SEQ ID NOs: 28-29).

FIG. 5 is a comparison of portions of the sequence of MxG0038 and MxG0220.

FIG. 7 provides the sequences of SEQ ID NOs: 30-37.

DETAILED DESCRIPTION

Figure 3:
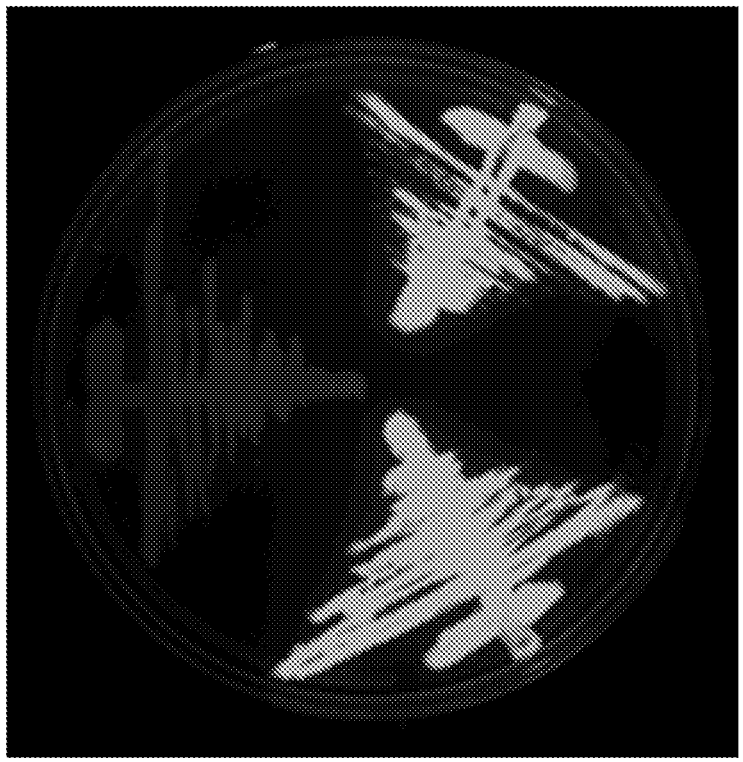
FIG. 3 is an image showing growth of pMx0414 transformants on YPD medium.

This document is related to materials and methods for protein production. For example, in one aspect, this document is related to materials and method for the production of products (e.g., proteins (e.g., plant proteins)) in cells (e.g., yeast (e.g., methylotrophic yeast) using an engineered promoter.

Methylotrophic yeast, such as *Pichia pastoris*, are commonly used to produce recombinant products (e.g., proteins). *Pichia* strains are typically able to grow on methanol as the sole carbon source. It will be understood that *Pichia pastoris* has been reclassified as *Komagataella* species, such as *Komagataella phaffii*, *Komagataella pastoris*, or *Komagataella pseudopastoris*, though the term '*Pichia pastoris*' is still in use and may refer to any appropriate *Komagataella* species. Commonly, laboratory strains of *P. pastoris* are *Komagataella phaffii*.

Methanol utilization can be initiated by the conversion of methanol to formaldehyde by the action of alcohol oxidase. *P. pastoris* contains two genes for alcohol oxidases, AOX1 and AOX2. Strains with reduced alcohol oxidase activity ("methanol utilization slow" or MutS strains) can usually produce more of a recombinant product (e.g., protein) expressed from the AOX1 promoter than strains that do not have reduced alcohol oxidase activity. The *Pichia pastoris* promoter for the alcohol oxidase 1 (AOX1) gene, referred to as pAOX1, can be used for production of heterologous products (e.g., proteins (e.g., proteins of industrial relevance)). Expression from this promoter can be induced in the presence of methanol, a flammable and toxic compound. In some embodiments, the materials and methods described herein can allow for expression of recombinant products (e.g., proteins) at high level from this promoter, or a promoter element therefrom, in the absence of methanol. In some embodiments, the materials and methods described herein can allow for expression of recombinant products (e.g., proteins) at high level from this promoter, or a promoter element therefrom, in the absence of added methanol.

Expression from pAOX1 is typically absent or very poor in the presence of non-inducing carbon sources, such as glucose or glycerol. Herein are described mutations in pAOX1 that allow significant expression from pAOX1 in the absence of methanol. Herein are described mutations in pAOX1 that allow significant expression from pAOX1 in the absence of added methanol. A reference pAOX1 sequence is provided in SEQ ID NO: 28 (FIG. 2). Exemplary mutations in pAOX1, as described herein, are provided in SEQ ID NO: 29 (FIG. 2). These mutations can be present individually or in any combination. These mutations can also provide an additional increase in expression from pAOX1 when methanol is present.

Thus, provided herein are nucleic acid constructs (sometimes also called nucleic acid molecules) that include a promoter element having a sequence that includes one or more mutations as compared to a reference promoter sequence. In some embodiments, a promoter element can be an alcohol oxidase promoter element. In some embodiments, a promoter element can have at least 70% (e.g., at least 75%, 80%, 85%, 90%, 95%, 97%, 98%, or 99%) sequence identity to an alcohol oxidase promoter element (e.g., SEQ ID NO: 28 or SEQ ID NO: 29). In some embodiments, a promoter element can have the sequence of SEQ ID NO: 29. In some embodiments, a single mutation can be present in a promoter element. For example, in some embodiments, a single mutation corresponding to a mutation in one of nucleotide positions 668-734 (e.g., nucleotide positions 673-729, nucleotide positions 678-724, nucleotide positions 683-719, or nucleotide positions 688-714) relative to SEQ ID NO: 28 can be present in a promoter element. For example, in some embodiments, a single mutation corresponding to one of the following mutations relative to SEQ ID NO: 28 can be present in a promoter element: T146C; C154T; T303C; T426A; A433T; A435G; T530A; C572T; T596C; T617C; T688C; A696T; T702C; A709G; A712G; T714G; A790G; A841T; or T862A. For example, in some embodiments, a single mutation corresponding to one of the following mutations relative to SEQ ID NO: 28 can be present in a promoter element: 146C; 154T; 303C; 426A; 433T; 435G; 530A; 572T; 596C; 617C; 688C; 696T; 702C; 709G; 712G; 714G; 790G; 841T; or 862A, as long as the indicated nucleobase is not the same as the corresponding naturally-occurring nucleobase. For example, in some embodiments, a single mutation at a position corresponding to one of the following positions relative to SEQ ID NO: 28 can be present in a promoter element: T146; C154; T303; T426; A433; A435; T530; C572; T596; T617; T688; A696; T702; A709; A712; T714; A790; A841; or T862. For example, in some embodiments, a single mutation at a position corresponding to one of the following positions relative to SEQ ID NO: 28 can be present in a promoter element: 146; 154; 303; 426; 433; 435; 530; 572; 596; 617; 688; 696; 702; 709; 712; 714; 790; 841; or 862. For example, in some embodiments, a single mutation corresponding to one of the following mutations relative to SEQ ID NO: 28 can be present in a promoter element: T688C; A696T; T702C; A712G; or T714G. For example, in some embodiments, a single mutation corresponding to one of the following mutations relative to SEQ ID NO: 28 can be present in a promoter element: 688C; 696T; 702C; 712G; or 714G, as long as the indicated nucleobase is not the same as the corresponding naturally-occurring nucleobase. For example, in some embodiments, a single mutation at a position corresponding to one of the following positions relative to SEQ ID NO: 28 can be present in a promoter element: T688; A696; T702; A712; or T714. For example, in some embodiments, a single mutation at a position corresponding to one of the following positions relative to SEQ ID NO: 28 can be present in a promoter element: 688; 696; 702; 712; or 714.

Also provided herein are nucleic acid constructs that include a promoter element having a sequence that includes multiple (e.g., 2, 3, 4, 5, 6, 7, 8, 9, 10, 11, 12, 13, 14, 15, 16, 17, 18, 19, 20, or more) mutations as compared to a reference promoter sequence. For example, in some embodiments, at least 2 (e.g., at least 3, at least 4, at least 5, at least 10, at least 15, 2 to 5, 2 to 10, 2 to 15, 2 to 20, 5 to 10, 5 to 15, 5 to 20, 10 to 15, 10 to 20, or 15 to 20) mutations corresponding to a mutation in nucleotide positions 668-734 (e.g., nucleotide positions 673-729, nucleotide positions 678-724, nucleotide positions 683-719, or nucleotide positions 688-714) relative to SEQ ID NO: 28 can be present in a promoter element. For example, in some embodiments, at least 2 (e.g., at least 3, at least 4, at least 5, at least 6, at least 7, at least 8, at least 9, at least 10, at least 12, at least 14, at least 16, at least 18, 2, 3, 4, 5, 6, 7, 8, 9, 10, 11, 12, 13, 14, 15, 16, 17, 18, or 19) mutations corresponding to the following mutations relative to SEQ ID NO: 28 can be present in a promoter element: T146C; C154T; T303C; T426A; A433T; A435G; T530A; C572T; T596C; T617C; T688C; A696T; T702C; A709G; A712G; T714G; A790G; A841T; or T862A. For example, in some embodiments, at least 2 (e.g., at least 3, at least 4, at least 5, at least 6, at least 7, at least 8, at least 9, at least 10, at least 12, at least 14, at least 16, at least 18, 2, 3, 4, 5, 6, 7, 8, 9, 10, 11, 12, 13, 14, 15, 16, 17, 18, or 19) mutations corresponding to the following mutations relative to SEQ ID NO: 28 can be present in a promoter element: 146C; 154T; 303C; 426A; 433T; 435G; 530A; 572T; 596C; 617C; 688C; 696T; 702C; 709G; 712G; 714G; 790G; 841T; or 862A, as long as the indicated nucleobase is not the same as the corresponding naturally-occurring nucleobase. For example, in some embodiments, at least 2 (e.g., at least 3, at least 4, at least 5, at least 6, at least 7, at least 8, at least 9, at least 10, at least 12, at least 14, at least 16, at least 18, 2, 3, 4, 5, 6, 7, 8, 9, 10, 11, 12, 13, 14, 15, 16, 17, 18, or 19) mutations at positions corresponding to the following positions relative to SEQ ID NO: 28 can be present in a promoter element: T146; C154; T303; T426; A433; A435; T530; C572; T596; T617; T688; A696; T702; A709; A712; T714; A790; A841; or T862. For example, in some embodiments, at least 2 (e.g., at least 3, at least 4, at least 5, at least 6, at least 7, at least 8, at least 9, at least 10, at least 12, at least 14, at least 16, at least 18, 2, 3, 4, 5, 6, 7, 8, 9, 10, 11, 12, 13, 14, 15, 16, 17, 18, or 19) mutations at positions corresponding to the following positions relative to SEQ ID NO: 28 can be present in a promoter element: 146; 154; 303; 426; 433; 435; 530; 572; 596; 617; 688; 696; 702; 709; 712; 714; 790; 841; or 862. For example, in some embodiments, at least 2 (e.g., at least 3, at least 4, 2, 3, 4, or 5) mutations corresponding to the following mutations relative to SEQ ID NO: 28 can be present in a promoter element: T688C; A696T; T702C; A712G; or T714G. For example, in some embodiments, at least 2 (e.g., at least 3, at least 4, 2, 3, 4, or 5) mutations corresponding to the following mutations relative to SEQ ID NO: 28 can be present in a promoter element: 688C; 696T; 702C; 712G; or 714G, as long as the indicated nucleobase is not the same as the corresponding naturally-occurring nucleobase. For example, in some embodiments, at least 2 (e.g., at least 3, at least 4, 2, 3, 4, or 5) mutations corresponding to one of the following positions relative to SEQ ID NO: 28 can be present in a promoter element: T688; A696; T702; A712; or T714. For example, in some embodiments, at least 2 (e.g., at least 3, at least 4, 2, 3, 4, or 5) mutations corresponding to one of the following positions relative to SEQ ID NO: 28 can be present in a promoter element: 688; 696; 702; 712; or 714.

In some embodiments, a mutation in a nucleic acid can be an insertion, a deletion or a substitution. In some embodiments, a mutation in a nucleic acid can be a substitution (e.g., a guanosine to cytosine mutation). In some embodiments, a mutation in a nucleic acid can be in a non-coding sequence. In some embodiments, a substitution in a coding sequence (e.g., encoding a protein) can be a silent mutation (e.g., the same amino acid is encoded). In some embodiments, a substitution in a coding sequence can be a nonsynonymous mutation (e.g., a missense mutation or a nonsense mutation). In some embodiments, a substitution in a coding sequence can be a missense mutation (e.g., a different amino acid is encoded). In some embodiments, a substitution in a coding sequence can be nonsense mutation (e.g., a premature stop codon is encoded). It will be understood that mutations can be used to alter an endogenous nucleic acid, using, for example, CRISPR, TALEN, and/or Zinc-finger nucleases.

In some embodiments, a mutation in a protein sequence can be an insertion, a deletion, or a substitution. It will be understood that a mutation in a nucleic acid that encodes a protein can cause a mutation in a protein sequence. In some embodiments, a mutation in a protein sequence is a substitution (e.g., a cysteine to serine mutation, or a cysteine to alanine mutation).

As used herein, a "corresponding" nucleic acid position (or substitution) in a nucleic acid sequence different from a reference nucleic acid sequence (e.g., in a truncated, extended, or mutated nucleic acid sequence of a pAOX1 promoter compared to a reference pAOX nucleic acid sequence, such as SEQ ID NO: 28) can be identified by performing a sequence alignment between the nucleic acid sequences of interest. It will be understood that in some cases, a gap can exist in a nucleic acid alignment. Similarly, a "corresponding" amino acid position (or substitution) in a protein sequence different from a reference protein sequence (e.g., in the myoglobin protein sequence of a different organism compared to a reference myoglobin protein sequence, such as SEQ ID NO: 18) can be identified by performing a sequence alignment between the protein sequences of interest. It will be understood that in some cases, a gap can exist in a protein alignment. As used herein, a nucleotide or amino acid position "relative to" a reference sequence can be the corresponding nucleotide or amino acid position in a reference sequence.

In some embodiments, a reference sequence can be from the same taxonomic rank as a comparator sequence. In some embodiments, a reference sequence can be from the same domain as a comparator sequence. For example, in some embodiments, both a reference sequence and a comparator sequence can be from domain Eukarya. In some embodiments, a reference sequence can be from the same kingdom as a comparator sequence. For example, in some embodiments, both a reference sequence and a comparator sequence can be from the kingdom Fungi. In some embodiments, a reference sequence can be from the same phylum as a comparator sequence. For example, in some embodiments, both a reference sequence and a comparator sequence can be from phylum Ascomycota. In some embodiments, a reference sequence can be from the same class as a comparator sequence. For example, in some embodiments, both a reference sequence and a comparator sequence can be from the class Saccharomycetes. In some embodiments, a reference sequence can be from the same order as a comparator sequence. For example, in some embodiments, both a reference sequence and a comparator sequence can be from the order Saccharomycetales. In some embodiments, a reference sequence can be from the same family as a comparator sequence. For example, in some embodiments, both a reference sequence and comparator sequence can be from the family Saccharomycetaceae. In some embodiments, a reference sequence can be from the same genus as a comparator sequence. For example, in some embodiments, both a reference sequence and a comparator sequence can be from the genus *Pichia*. In some embodiments, a reference sequence can be from the same species as a comparator sequence.

In some embodiments, a reference sequence and a comparator sequence can both be from yeast. In some embodiments, a reference sequence and a comparator sequence can both be from methylotrophic yeast.

In some embodiments, a reference sequence and a comparator sequence can have at least 50% (e.g., at least 55%, 60%, 65%, 70%, 75%, 80%, 85%, 90%, or 99%) sequence identity.

In some embodiments, the nucleotide sequence of a promoter element as provided herein can include two mutations as compared to the nucleotide sequence of a reference promoter element. For example, in some embodiments, two mutations corresponding to the following mutations relative to SEQ ID NO: 28 can be present in a promoter sequence: T146C and C154T; T146C and T303C; T146C and T426A; T146C and A433T; T146C and A435G; T146C and T530A; T146C and C572T; T146C and T596C; T146C and T617C; T146C and T688C; T146C and A696T; T146C and T702C; T146C and A709G; T146C and A712G; T146C and T714G; T146C and A790G; T146C and A841T; T146C and T862A; C154T and T303C; C154T and T426A; C154T and A433T; C154T and A435G; C154T and T530A; C154T and C572T; C154T and T596C; C154T and T617C; C154T and T688C; C154T and A696T; C154T and T702C; C154T and A709G; C154T and A712G; C154T and T714G; C154T and A790G; C154T and A841T; C154T and T862A; T303C and T426A; T303C and A433T; T303C and A435G; T303C and T530A; T303C and C572T; T303C and T596C; T303C and T617C; T303C and T688C; T303C and A696T; T303C and T702C; T303C and A709G; T303C and A712G; T303C and T714G; T303C and A790G; T303C and A841T; T303C and T862A; T426A and A433T; T426A and A435G; T426A and T530A; T426A and C572T; T426A and T596C; T426A and T617C; T426A and T688C; T426A and A696T; T426A and T702C; T426A and A709G; T426A and A712G; T426A and T714G; T426A and A790G; T426A and A841T; T426A and T862A; A433T and A435G; A433T and T530A; A433T and C572T; A433T and T596C; A433T and T617C; A433T and T688C; A433T and A696T; A433T and T702C; A433T and A709G; A433T and A712G; A433T and T714G; A433T and A790G; A433T and A841T; A433T and T862A; A435G and T530A;

A435G and C572T; A435G and T596C; A435G and T617C; A435G and T688C; A435G and A696T; A435G and T702C; A435G and A709G; A435G and A712G; A435G and T714G; A435G and A790G; A435G and A841T; A435G and T862A; T530A and C572T; T530A and T596C; T530A and T617C; T530A and T688C; T530A and A696T; T530A and T702C; T530A and A709G; T530A and A712G; T530A and T714G; T530A and A790G; T530A and A841T; T530A and T862A; C572T and T596C; C572T and T617C; C572T and T688C; C572T and A696T; C572T and T702C; C572T and A709G; C572T and A712G; C572T and T714G; C572T and A790G; C572T and A841T; C572T and T862A; T596C and T617C; T596C and T688C; T596C and A696T; T596C and T702C; T596C and A709G; T596C and A712G; T596C and T714G; T596C and A790G; T596C and A841T; T596C and T862A; T617C and T688C; T617C and A696T; T617C and T702C; T617C and A709G; T617C and A712G; T617C and T714G; T617C and A790G; T617C and A841T; T617C and T862A; T688C and A696T; T688C and T702C; T688C and A709G; T688C and A712G; T688C and T714G; T688C and A790G; T688C and A841T; T688C and T862A; A696T and T702C; A696T and A709G; A696T and A712G; A696T and T714G; A696T and A790G; A696T and A841T; A696T and T862A; T702C and A709G; T702C and A712G; T702C and T714G; T702C and A790G; T702C and A841T; T702C and T862A; A709G and A712G; A709G and T714G; A709G and A790G; A709G and A841T; A709G and T862A; A712G and T714G; A712G and A790G; A712G and A841T; A712G and T862A; T714G and A790G; T714G and A841T; T714G and T862A; A790G and A841T; A790G and T862A; or A841T and T862A.

In some embodiments, the nucleotide sequence of a promoter element as provided herein can include three mutations as compared to the nucleotide sequence of a reference promoter element. For example, in some embodiments, three mutations corresponding to the following mutations relative to SEQ ID NO: 28 can be present in a promoter sequence: T146C, C154T, and T303C; T146C, C154T, and T426A; T146C, C154T, and A433T; T146C, C154T, and A435G; T146C, C154T, and T530A; T146C, C154T, and C572T; T146C, C154T, and T596C; T146C, C154T, and T617C; T146C, C154T, and T688C; T146C, C154T, and A696T; T146C, C154T, and T702C; T146C, C154T, and A709G; T146C, C154T, and A712G; T146C, C154T, and T714G; T146C, C154T, and A790G; T146C, C154T, and A841T; T146C, C154T, and T862A; T146C, T303C, and T426A; T146C, T303C, and A433T; T146C, T303C, and A435G; T146C, T303C, and T530A; T146C, T303C, and C572T; T146C, T303C, and T596C; T146C, T303C, and T617C; T146C, T303C, and T688C; T146C, T303C, and A696T; T146C, T303C, and T702C; T146C, T303C, and A709G; T146C, T303C, and A712G; T146C, T303C, and T714G; T146C, T303C, and A790G; T146C, T303C, and A841T; T146C, T303C, and T862A; T146C, T426A, and A433T; T146C, T426A, and A435G; T146C, T426A, and T530A; T146C, T426A, and C572T; T146C, T426A, and T596C; T146C, T426A, and T617C; T146C, T426A, and T688C; T146C, T426A, and A696T; T146C, T426A, and T702C; T146C, T426A, and A709G; T146C, T426A, and A712G; T146C, T426A, and T714G; T146C, T426A, and A790G; T146C, T426A, and A841T; T146C, T426A, and T862A; T146C, A433T, and A435G; T146C, A433T, and T530A; T146C, A433T, and C572T; T146C, A433T, and T596C; T146C, A433T, and T617C; T146C, A433T, and T688C; T146C, A433T, and A696T; T146C, A433T, and T702C; T146C, A433T, and A709G; T146C, A433T, and A712G; T146C, A433T, and T714G; T146C, A433T, and A790G; T146C, A433T, and A841T; T146C, A433T, and T862A; T146C, A435G, and T530A; T146C, A435G, and C572T; T146C, A435G, and T596C; T146C, A435G, and T617C; T146C, A435G, and T688C; T146C, A435G, and A696T; T146C, A435G, and T702C; T146C, A435G, and A709G; T146C, A435G, and A712G; T146C, A435G, and T714G; T146C, A435G, and A790G; T146C, A435G, and A841T; T146C, A435G, and T862A; T146C, T530A, and C572T; T146C, T530A, and T596C; T146C, T530A, and T617C; T146C, T530A, and T688C; T146C, T530A, and A696T; T146C, T530A, and T702C; T146C, T530A, and A709G; T146C, T530A, and A712G; T146C, T530A, and T714G; T146C, T530A, and A790G; T146C, T530A, and A841T; T146C, T530A, and T862A; T146C, C572T, and T596C; T146C, C572T, and T617C; T146C, C572T, and T688C; T146C, C572T, and A696T; T146C, C572T, and T702C; T146C, C572T, and A709G; T146C, C572T, and A712G; T146C, C572T, and T714G; T146C, C572T, and A790G; T146C, C572T, and A841T; T146C, C572T, and T862A; T146C, T596C, and T617C; T146C, T596C, and T688C; T146C, T596C, and A696T; T146C, T596C, and T702C; T146C, T596C, and A709G; T146C, T596C, and A712G; T146C, T596C, and T714G; T146C, T596C, and A790G; T146C, T596C, and A841T; T146C, T596C, and T862A; T146C, T617C, and T688C; T146C, T617C, and A696T; T146C, T617C, and T702C; T146C, T617C, and A709G; T146C, T617C, and A712G; T146C, T617C, and T714G; T146C, T617C, and A790G; T146C, T617C, and A841T; T146C, T617C, and T862A; T146C, T688C, and A696T; T146C, T688C, and T702C; T146C, T688C, and A709G; T146C, T688C, and A712G; T146C, T688C, and T714G; T146C, T688C, and A790G; T146C, T688C, and A841T; T146C, T688C, and T862A; T146C, A696T, and T702C; T146C, A696T, and A709G; T146C, A696T, and A712G; T146C, A696T, and T714G; T146C, A696T, and A790G; T146C, A696T, and A841T; T146C, A696T, and T862A; T146C, T702C, and A709G; T146C, T702C, and A712G; T146C, T702C, and T714G; T146C, T702C, and A790G; T146C, T702C, and A841T; T146C, T702C, and T862A; T146C, A709G, and A712G; T146C, A709G, and T714G; T146C, A709G, and A790G; T146C, A709G, and A841T; T146C, A709G, and T862A; T146C, A712G, and T714G; T146C, A712G, and A790G; T146C, A712G, and A841T; T146C, A712G, and T862A; T146C, T714G, and A790G; T146C, T714G, and A841T; T146C, T714G, and T862A; T146C, A790G, and A841T; T146C, A790G, and T862A; T146C, A841T, and T862A; C154T, T303C, and T426A; C154T, T303C, and A433T; C154T, T303C, and A435G; C154T, T303C, and T530A; C154T, T303C, and C572T; C154T, T303C, and T596C; C154T, T303C, and T617C; C154T, T303C, and T688C; C154T, T303C, and A696T; C154T, T303C, and T702C; C154T, T303C, and A709G; C154T, T303C, and A712G; C154T, T303C, and T714G; C154T, T303C, and A790G; C154T, T303C, and A841T; C154T, T303C, and T862A; C154T, T426A, and A433T; C154T, T426A, and A435G; C154T, T426A, and T530A; C154T, T426A, and C572T; C154T, T426A, and T596C; C154T, T426A, and T617C; C154T, T426A, and T688C; C154T, T426A, and A696T; C154T, T426A, and T702C; C154T, T426A, and A709G; C154T, T426A, and A712G; C154T, T426A, and T714G; C154T, T426A, and A790G; C154T, T426A, and A841T; C154T, T426A, and T862A; C154T, A433T, and A435G; C154T, A433T, and T530A; C154T, A433T, and C572T; C154T, A433T, and T596C; C154T, A433T, and T617C; C154T, A433T, and T688C; C154T, A433T, and A696T; C154T, A433T, and T702C; C154T, A433T, and A709G; C154T, A433T, and A712G; C154T, A433T, and T714G; C154T, A433T, and A790G; C154T, A433T, and A841T; C154T, A433T, and T862A; C154T, A435G, and T530A; C154T, A435G, and C572T; C154T, A435G, and T596C; C154T, A435G, and T617C; C154T, A435G, and T688C; C154T, A435G, and A696T; C154T, A435G, and T702C; C154T, A435G, and A709G; C154T, A435G, and A712G; C154T, A435G, and T714G; C154T, A435G, and A790G; C154T, A435G, and A841T; C154T, A435G, and T862A; C154T, T530A, and C572T; C154T, T530A, and T596C; C154T, T530A, and T617C; C154T, T530A, and T688C; C154T, T530A, and A696T; C154T, T530A, and T702C; C154T, T530A, and A709G; C154T, T530A, and A712G; C154T, T530A, and T714G; C154T, T530A, and A790G; C154T, T530A, and A841T; C154T, T530A, and T862A; C154T, C572T, and T596C; C154T, C572T, and T617C; C154T, C572T, and T688C; C154T, C572T, and A696T; C154T, C572T, and T702C; C154T, C572T, and A709G; C154T, C572T, and A712G; C154T, C572T, and T714G; C154T, C572T, and A790G; C154T, C572T, and A841T; C154T, C572T, and T862A; C154T, T596C, and T617C; C154T, T596C, and T688C; C154T, T596C, and A696T; C154T, T596C, and T702C; C154T, T596C, and A709G; C154T, T596C, and A712G; C154T, T596C, and T714G; C154T, T596C, and A790G; C154T, T596C, and A841T; C154T, T596C, and T862A; C154T, T617C, and T688C; C154T, T617C, and A696T; C154T, T617C, and T702C; C154T, T617C, and A709G; C154T, T617C, and A712G; C154T, T617C, and T714G; C154T, T617C, and A790G; C154T, T617C, and A841T; C154T, T617C, and T862A; C154T, T688C, and A696T; C154T, T688C, and T702C; C154T, T688C, and A709G; C154T, T688C, and A712G; C154T, T688C, and T714G; C154T, T688C, and A790G; C154T, T688C, and A841T; C154T, T688C, and T862A; C154T, A696T, and T702C; C154T, A696T, and A709G; C154T, A696T, and A712G; C154T, A696T, and T714G; C154T, A696T, and A790G; C154T, A696T, and A841T; C154T, A696T, and T862A; C154T, T702C, and A709G; C154T, T702C, and A712G; C154T, T702C, and T714G; C154T, T702C, and A790G; C154T, T702C, and A841T; C154T, T702C, and T862A; C154T, A709G, and A712G; C154T, A709G, and T714G; C154T, A709G, and A790G; C154T, A709G, and A841T; C154T, A709G, and T862A; C154T, A712G, and T714G; C154T, A712G, and A790G; C154T, A712G, and A841T; C154T, A712G, and T862A; C154T, T714G, and A790G; C154T, T714G, and A841T; C154T, T714G, and T862A; C154T, A790G, and A841T; C154T, A790G, and T862A; C154T, A841T, and T862A; T303C, T426A, and A433T; T303C, T426A, and A435G; T303C, T426A, and T530A; T303C, T426A, and C572T; T303C, T426A, and T596C; T303C, T426A, and T617C; T303C, T426A, and T688C; T303C, T426A, and A696T; T303C, T426A, and T702C; T303C, T426A, and A709G; T303C, T426A, and A712G; T303C, T426A, and T714G; T303C, T426A, and A790G; T303C, T426A, and A841T; T303C, T426A, and T862A; T303C, A433T, and A435G; T303C, A433T, and T530A; T303C, A433T, and C572T; T303C, A433T, and T596C; T303C, A433T, and T617C; T303C, A433T, and T688C; T303C, A433T, and A696T; T303C, A433T, and T702C; T303C, A433T, and A709G; T303C, A433T, and A712G; T303C, A433T, and T714G; T303C, A433T, and A790G; T303C, A433T, and A841T; T303C, A433T, and T862A; T303C, A435G, and T530A; T303C, A435G, and C572T; T303C, A435G, and T596C; T303C, A435G, and T617C; T303C, A435G, and T688C; T303C, A435G, and A696T; T303C, A435G, and T702C; T303C, A435G, and A709G; T303C, A435G, and A712G; T303C, A435G, and T714G; T303C, A435G, and A790G; T303C, A435G, and A841T; T303C, A435G, and T862A; T303C, T530A, and C572T; T303C, T530A, and T596C; T303C, T530A, and T617C; T303C, T530A, and T688C; T303C, T530A, and A696T; T303C, T530A, and T702C; T303C, T530A, and A709G; T303C, T530A, and A712G; T303C, T530A, and T714G; T303C, T530A, and A790G; T303C, T530A, and A841T; T303C, T530A, and T862A; T303C, C572T, and T596C; T303C, C572T, and T617C; T303C, C572T, and T688C; T303C, C572T, and A696T; T303C, C572T, and T702C; T303C, C572T, and A709G; T303C, C572T, and A712G; T303C, C572T, and T714G; T303C, C572T, and A790G; T303C, C572T, and A841T; T303C, C572T, and T862A; T303C, T596C, and T617C; T303C, T596C, and T688C; T303C, T596C, and A696T; T303C, T596C, and T702C; T303C, T596C, and A709G; T303C, T596C, and A712G; T303C, T596C, and T714G; T303C, T596C, and A790G; T303C, T596C, and A841T; T303C, T596C, and T862A; T303C, T617C, and T688C; T303C, T617C, and A696T; T303C, T617C, and T702C; T303C, T617C, and A709G; T303C, T617C, and A712G; T303C, T617C, and T714G; T303C, T617C, and A790G; T303C, T617C, and A841T; T303C, T617C, and T862A; T303C, T688C, and A696T; T303C, T688C, and T702C; T303C, T688C, and A709G; T303C, T688C, and A712G; T303C, T688C, and T714G; T303C, T688C, and A790G; T303C, T688C, and A841T; T303C, T688C, and T862A; T303C, A696T, and T702C; T303C, A696T, and A709G; T303C, A696T, and A712G; T303C, A696T, and T714G; T303C, A696T, and A790G; T303C, A696T, and A841T; T303C, A696T, and T862A; T303C, T702C, and A709G; T303C, T702C, and A712G; T303C, T702C, and T714G; T303C, T702C, and A790G; T303C, T702C, and A841T; T303C, T702C, and T862A; T303C, A709G, and A712G; T303C, A709G, and T714G; T303C, A709G, and A790G; T303C, A709G, and A841T; T303C, A709G, and T862A; T303C, A712G, and T714G; T303C, A712G, and A790G; T303C, A712G, and A841T; T303C, A712G, and T862A; T303C, T714G, and A790G; T303C, T714G, and A841T; T303C, T714G, and T862A; T303C, A790G, and A841T; T303C, A790G, and T862A; T303C, A841T, and T862A; T426A, A433T, and A435G; T426A, A433T, and T530A; T426A, A433T, and C572T; T426A, A433T, and T596C; T426A, A433T, and T617C; T426A, A433T, and T688C; T426A, A433T, and A696T; T426A, A433T, and T702C; T426A, A433T, and A709G; T426A, A433T, and A712G; T426A, A433T, and T714G; T426A, A433T, and A790G; T426A, A433T, and A841T; T426A, A433T, and T862A; T426A, A435G, and T530A; T426A, A435G, and C572T; T426A, A435G, and T596C; T426A, A435G, and T617C; T426A, A435G, and T688C; T426A, A435G, and A696T; T426A, A435G, and T702C; T426A, A435G, and A709G; T426A, A435G, and A712G; T426A, A435G, and T714G; T426A, A435G, and A790G; T426A, A435G, and A841T; T426A, A435G, and T862A; T426A, T530A, and C572T; T426A, T530A, and T596C; T426A, T530A, and T617C; T426A, T530A, and T688C; T426A, T530A, and A696T; T426A, T530A, and T702C; T426A, T530A, and A709G; T426A, T530A, and A712G; T426A, T530A, and T714G; T426A, T530A, and A790G; T426A, T530A, and A841T; T426A, T530A, and T862A; T426A, C572T, and T596C; T426A, C572T, and T617C; T426A, C572T, and T688C; T426A, C572T, and A696T; T426A, C572T, and T702C; T426A, C572T, and A709G; T426A, C572T, and A712G; T426A, C572T, and T714G; T426A, C572T, and A790G; T426A, C572T, and A841T; T426A, C572T, and T862A; T426A, T596C, and T617C; T426A, T596C, and T688C; T426A, T596C, and A696T; T426A, T596C, and T702C; T426A, T596C, and A709G; T426A, T596C, and A712G; T426A, T596C, and T714G; T426A, T596C, and A790G; T426A, T596C, and A841T; T426A, T596C, and T862A; T426A, T617C, and T688C; T426A, T617C, and A696T; T426A, T617C, and T702C; T426A, T617C, and A709G; T426A, T617C, and A712G; T426A, T617C, and T714G; T426A, T617C, and A790G; T426A, T617C, and A841T; T426A, T617C, and T862A; T426A, T688C, and A696T; T426A, T688C, and T702C; T426A, T688C, and A709G; T426A, T688C, and A712G; T426A, T688C, and T714G; T426A, T688C, and A790G; T426A, T688C, and A841T; T426A, T688C, and T862A; T426A, A696T, and T702C; T426A, A696T, and A709G; T426A, A696T, and A712G; T426A, A696T, and T714G; T426A, A696T, and A790G; T426A, A696T, and A841T; T426A, A696T, and T862A; T426A, T702C, and A709G; T426A, T702C, and A712G; T426A, T702C, and T714G; T426A, T702C, and A790G; T426A, T702C, and A841T; T426A, T702C, and T862A; T426A, A709G, and A712G; T426A, A709G, and T714G; T426A, A709G, and A790G; T426A, A709G, and A841T; T426A, A709G, and T862A; T426A, A712G, and T714G; T426A, A712G, and A790G; T426A, A712G, and A841T; T426A, A712G, and T862A; T426A, T714G, and A790G; T426A, T714G, and A841T; T426A, T714G, and T862A; T426A, A790G, and A841T; T426A, A790G, and T862A; T426A, A841T, and T862A; A433T, A435G, and T530A; A433T, A435G, and C572T; A433T, A435G, and T596C; A433T, A435G, and T617C; A433T, A435G, and T688C; A433T, A435G, and A696T; A433T, A435G, and T702C; A433T, A435G, and A709G; A433T, A435G, and A712G; A433T, A435G, and T714G; A433T, A435G, and A790G; A433T, A435G, and A841T; A433T, A435G, and T862A; A433T, T530A, and C572T; A433T, T530A, and T596C; A433T, T530A, and T617C; A433T, T530A, and T688C; A433T, T530A, and A696T; A433T, T530A, and T702C; A433T, T530A, and A709G; A433T, T530A, and A712G; A433T, T530A, and T714G; A433T, T530A, and A790G; A433T, T530A, and A841T; A433T, T530A, and T862A; A433T, C572T, and T596C; A433T, C572T, and T617C; A433T, C572T, and T688C; A433T, C572T, and A696T; A433T, C572T, and T702C; A433T, C572T, and A709G; A433T, C572T, and A712G; A433T, C572T, and T714G; A433T, C572T, and A790G; A433T, C572T, and A841T; A433T, C572T, and T862A; A433T, T596C, and T617C; A433T, T596C, and T688C; A433T, T596C, and A696T; A433T, T596C, and T702C; A433T, T596C, and A709G; A433T, T596C, and A712G; A433T, T596C, and T714G; A433T, T596C, and A790G; A433T, T596C, and A841T; A433T, T596C, and T862A; A433T, T617C, and T688C; A433T, T617C, and A696T; A433T, T617C, and T702C; A433T, T617C, and A709G; A433T, T617C, and A712G; A433T, T617C, and T714G; A433T, T617C, and A790G; A433T, T617C, and A841T; A433T, T617C, and T862A; A433T, T688C, and A696T; A433T, T688C, and T702C; A433T, T688C, and A709G; A433T, T688C, and A712G; A433T, T688C, and T714G; A433T, T688C, and A790G; A433T, T688C, and A841T; A433T, T688C, and T862A; A433T, A696T, and T702C; A433T, A696T, and A709G; A433T, A696T, and A712G; A433T, A696T, and T714G; A433T, A696T, and A790G; A433T, A696T, and A841T; A433T, A696T, and T862A; A433T, T702C, and A709G; A433T, T702C, and A712G; A433T, T702C, and T714G; A433T, T702C, and A790G; A433T, T702C, and A841T; A433T, T702C, and T862A; A433T, A709G, and A712G; A433T, A709G, and T714G; A433T, A709G, and A790G; A433T, A709G, and A841T; A433T, A709G, and T862A; A433T, A712G, and T714G; A433T, A712G, and A790G; A433T, A712G, and A841T; A433T, A712G, and T862A; A433T, T714G, and A790G; A433T, T714G, and A841T; A433T, T714G, and T862A; A433T, A790G, and A841T; A433T, A790G, and T862A; A433T, A841T, and T862A; A435G, T530A, and C572T; A435G, T530A, and T596C; A435G, T530A, and T617C; A435G, T530A, and T688C; A435G, T530A, and A696T; A435G, T530A, and T702C; A435G, T530A, and A709G; A435G, T530A, and A712G; A435G, T530A, and T714G; A435G, T530A, and A790G; A435G, T530A, and A841T; A435G, T530A, and T862A; A435G, C572T, and T596C; A435G, C572T, and T617C; A435G, C572T, and T688C; A435G, C572T, and A696T; A435G, C572T, and T702C; A435G, C572T, and A709G; A435G, C572T, and A712G; A435G, C572T, and T714G; A435G, C572T, and A790G; A435G, C572T, and A841T; A435G, C572T, and T862A; A435G, T596C, and T617C; A435G, T596C, and T688C; A435G, T596C, and A696T; A435G, T596C, and T702C; A435G, T596C, and A709G; A435G, T596C, and A712G; A435G, T596C, and T714G; A435G, T596C, and A790G; A435G, T596C, and A841T; A435G, T596C, and T862A; A435G, T617C, and T688C; A435G, T617C, and A696T; A435G, T617C, and T702C; A435G, T617C, and A709G; A435G, T617C, and A712G; A435G, T617C, and T714G; A435G, T617C, and A790G; A435G, T617C, and A841T; A435G, T617C, and T862A; A435G, T688C, and A696T; A435G, T688C, and T702C; A435G, T688C, and A709G; A435G, T688C, and A712G; A435G, T688C, and T714G; A435G, T688C, and A790G; A435G, T688C, and A841T; A435G, T688C, and T862A; A435G, A696T, and T702C; A435G, A696T, and A709G; A435G, A696T, and A712G; A435G, A696T, and T714G; A435G, A696T, and A790G; A435G, A696T, and A841T; A435G, A696T, and T862A; A435G, T702C, and A709G; A435G, T702C, and A712G; A435G, T702C, and T714G; A435G, T702C, and A790G; A435G, T702C, and A841T; A435G, T702C, and T862A; A435G, A709G, and A712G; A435G, A709G, and T714G; A435G, A709G, and A790G; A435G, A709G, and A841T; A435G, A709G, and T862A; A435G, A712G, and T714G; A435G, A712G, and A790G; A435G, A712G, and A841T; A435G, A712G, and T862A; A435G, T714G, and A790G; A435G, T714G, and A841T; A435G, T714G, and T862A; A435G, A790G, and A841T; A435G, A790G, and T862A; A435G, A841T, and T862A; T530A, C572T, and T596C; T530A, C572T, and T617C; T530A, C572T, and T688C; T530A, C572T, and A696T; T530A, C572T, and T702C; T530A, C572T, and A709G; T530A, C572T, and A712G; T530A, C572T, and T714G; T530A, C572T, and A790G; T530A, C572T, and A841T; T530A, C572T, and T862A; T530A, T596C, and T617C; T530A, T596C, and T688C; T530A, T596C, and A696T; T530A, T596C, and T702C; T530A, T596C, and A709G; T530A, T596C, and A712G; T530A, T596C, and T714G; T530A, T596C, and A790G; T530A, T596C, and A841T; T530A, T596C, and T862A; T530A, T617C, and T688C; T530A, T617C, and A696T; T530A, T617C, and T702C; T530A, T617C, and A709G; T530A, T617C, and A712G; T530A, T617C, and T714G; T530A, T617C, and A790G; T530A, T617C, and A841T; T530A, T617C, and T862A; T530A, T688C, and A696T; T530A, T688C, and T702C; T530A, T688C, and A709G; T530A, T688C, and A712G; T530A, T688C, and T714G; T530A, T688C, and A790G; T530A, T688C, and A841T; T530A, T688C, and T862A; T530A, A696T, and T702C; T530A, A696T, and A709G; T530A, A696T, and A712G; T530A, A696T, and T714G; T530A, A696T, and A790G; T530A, A696T, and A841T; T530A, A696T, and T862A; T530A, T702C, and A709G; T530A, T702C, and A712G; T530A, T702C, and T714G; T530A, T702C, and A790G; T530A, T702C, and A841T; T530A, T702C, and T862A; T530A, A709G, and A712G; T530A, A709G, and T714G; T530A, A709G, and A790G; T530A, A709G, and A841T; T530A, A709G, and T862A; T530A, A712G, and T714G; T530A, A712G, and A790G; T530A, A712G, and A841T; T530A, A712G, and T862A; T530A, T714G, and A790G; T530A, T714G, and A841T; T530A, T714G, and T862A; T530A, A790G, and A841T; T530A, A790G, and T862A; T530A, A841T, and T862A; C572T, T596C, and T617C; C572T, T596C, and T688C; C572T, T596C, and A696T; C572T, T596C, and T702C; C572T, T596C, and A709G; C572T, T596C, and A712G; C572T, T596C, and T714G; C572T, T596C, and A790G; C572T, T596C, and A841T; C572T, T596C, and T862A; C572T, T617C, and T688C; C572T, T617C, and A696T; C572T, T617C, and T702C; C572T, T617C, and A709G; C572T, T617C, and A712G; C572T, T617C, and T714G; C572T, T617C, and A790G; C572T, T617C, and A841T; C572T, T617C, and T862A; C572T, T688C, and A696T; C572T, T688C, and T702C; C572T, T688C, and A709G; C572T, T688C, and A712G; C572T, T688C, and T714G; C572T, T688C, and A790G; C572T, T688C, and A841T; C572T, T688C, and T862A; C572T, A696T, and T702C; C572T, A696T, and A709G; C572T, A696T, and A712G; C572T, A696T, and T714G; C572T, A696T, and A790G; C572T, A696T, and A841T; C572T, A696T, and T862A; C572T, T702C, and A709G; C572T, T702C, and A712G; C572T, T702C, and T714G; C572T, T702C, and A790G; C572T, T702C, and A841T; C572T, T702C, and T862A; C572T, A709G, and A712G; C572T, A709G, and T714G; C572T, A709G, and A790G; C572T, A709G, and A841T; C572T, A709G, and T862A; C572T, A712G, and T714G; C572T, A712G, and A790G; C572T, A712G, and A841T; C572T, A712G, and T862A; C572T, T714G, and A790G; C572T, T714G, and A841T; C572T, T714G, and T862A; C572T, A790G, and A841T; C572T, A790G, and T862A; C572T, A841T, and T862A; T596C, T617C, and T688C; T596C, T617C, and A696T; T596C, T617C, and T702C; T596C, T617C, and A709G; T596C, T617C, and A712G; T596C, T617C, and T714G; T596C, T617C, and A790G; T596C, T617C, and A841T; T596C, T617C, and T862A; T596C, T688C, and A696T; T596C, T688C, and T702C; T596C, T688C, and A709G; T596C, T688C, and A712G; T596C, T688C, and T714G; T596C, T688C, and A790G; T596C, T688C, and A841T; T596C, T688C, and T862A; T596C, A696T, and T702C; T596C, A696T, and A709G; T596C, A696T, and A712G; T596C, A696T, and T714G; T596C, A696T, and A790G; T596C, A696T, and A841T; T596C, A696T, and T862A; T596C, T702C, and A709G; T596C, T702C, and A712G; T596C, T702C, and T714G; T596C, T702C, and A790G; T596C, T702C, and A841T; T596C, T702C, and T862A; T596C, A709G, and A712G; T596C, A709G, and T714G; T596C, A709G, and A790G; T596C, A709G, and A841T; T596C, A709G, and T862A; T596C, A712G, and T714G; T596C, A712G, and A790G; T596C, A712G, and A841T; T596C, A712G, and T862A; T596C, T714G, and A790G; T596C, T714G, and A841T; T596C, T714G, and T862A; T596C, A790G, and A841T; T596C, A790G, and T862A; T596C, A841T, and T862A; T617C, T688C, and A696T; T617C, T688C, and T702C; T617C, T688C, and A709G; T617C, T688C, and A712G; T617C, T688C, and T714G; T617C, T688C, and A790G; T617C, T688C, and A841T; T617C, T688C, and T862A; T617C, A696T, and T702C; T617C, A696T, and A709G; T617C, A696T, and A712G; T617C, A696T, and T714G; T617C, A696T, and A790G; T617C, A696T, and A841T; T617C, A696T, and T862A; T617C, T702C, and A709G; T617C, T702C, and A712G; T617C, T702C, and T714G; T617C, T702C, and A790G; T617C, T702C, and A841T; T617C, T702C, and T862A; T617C, A709G, and A712G; T617C, A709G, and T714G; T617C, A709G, and A790G; T617C, A709G, and A841T; T617C, A709G, and T862A; T617C, A712G, and T714G; T617C, A712G, and A790G; T617C, A712G, and A841T; T617C, A712G, and T862A; T617C, T714G, and A790G; T617C, T714G, and A841T; T617C, T714G, and T862A; T617C, A790G, and A841T; T617C, A790G, and T862A; T617C, A841T, and T862A; T688C, A696T, and T702C; T688C, A696T, and A709G; T688C, A696T, and A712G; T688C, A696T, and T714G; T688C, A696T, and A790G; T688C, A696T, and A841T; T688C, A696T, and T862A; T688C, T702C, and A709G; T688C, T702C, and A712G; T688C, T702C, and T714G; T688C, T702C, and A790G; T688C, T702C, and A841T; T688C, T702C, and T862A; T688C, A709G, and A712G; T688C, A709G, and T714G; T688C, A709G, and A790G; T688C, A709G, and A841T; T688C, A709G, and T862A; T688C, A712G, and T714G; T688C, A712G, and A790G; T688C, A712G, and A841T; T688C, A712G, and T862A; T688C, T714G, and A790G; T688C, T714G, and A841T; T688C, T714G, and T862A; T688C, A790G, and A841T; T688C, A790G, and T862A; T688C, A841T, and T862A; A696T, T702C, and A709G; A696T, T702C, and A712G; A696T, T702C, and T714G; A696T, T702C, and A790G; A696T, T702C, and A841T; A696T, T702C, and T862A; A696T, A709G, and A712G; A696T, A709G, and T714G; A696T, A709G, and A790G; A696T, A709G, and A841T; A696T, A709G, and T862A; A696T, A712G, and T714G; A696T, A712G, and A790G; A696T, A712G, and A841T; A696T, A712G, and T862A; A696T, T714G, and A790G; A696T, T714G, and A841T; A696T, T714G, and T862A; A696T, A790G, and A841T; A696T, A790G, and T862A; A696T, A841T, and T862A; T702C, A709G, and A712G; T702C, A709G, and T714G; T702C, A709G, and A790G; T702C, A709G, and A841T; T702C, A709G, and T862A; T702C, A712G, and T714G; T702C, A712G, and A790G; T702C, A712G, and A841T; T702C, A712G, and T862A; T702C, T714G, and A790G; T702C, T714G, and A841T; T702C, T714G, and T862A; T702C, A790G, and A841T; T702C, A790G, and T862A; T702C, A841T, and T862A; A709G, A712G, and T714G; A709G, A712G, and A790G; A709G, A712G, and A841T; A709G, A712G, and T862A; A709G, T714G, and A790G; A709G, T714G, and A841T; A709G, T714G, and T862A; A709G, A790G, and A841T; A709G, A790G, and T862A; A709G, A841T, and T862A; A712G, T714G, and A790G; A712G, T714G, and A841T; A712G, T714G, and T862A; A712G, A790G, and A841T; A712G, A790G, and T862A; A712G, A841T, and T862A; T714G, A790G, and A841T; T714G, A790G, and T862A; T714G, A841T, and T862A; or A790G, A841T, and T862A.

In some embodiments, the nucleotide sequence of a promoter element as provided herein can include two mutations as compared to the nucleotide sequence of a reference promoter element. For example, in some embodiments, two mutations corresponding to the following mutations relative to SEQ ID NO: 28 can be present in a promoter sequence: T688C and A696T; T688C and T702C; T688C and A712G; T688C and T714G; A696T and T702C; A696T and A712G; A696T and T714G; T702C and A712G; T702C and T714G; or A712G and T714G.

In some embodiments, the nucleotide sequence of a promoter element as provided herein can include three mutations as compared to the nucleotide sequence of a reference promoter element. For example, in some embodiments, three mutations corresponding to the following mutations relative to SEQ ID NO: 28 can be present in a promoter sequence: T688C, A696T, and T702C; T688C, A696T, and A712G; T688C, A696T, and T714G; T688C, T702C, and A712G; T688C, T702C, and T714G; T688C, A712G, and T714G; A696T, T702C, and A712G; A696T, T702C, and T714G; A696T, A712G, and T714G; or T702C, A712G, and T714G.

In some embodiments, the nucleotide sequence of a promoter element as provided herein can include four mutations as compared to the nucleotide sequence of a reference promoter element. For example, in some embodiments, four mutations corresponding to the following mutations relative to SEQ ID NO: 28 can be present in a promoter sequence: T688C, A696T, T702C, and A712G; T688C, A696T, T702C, and T714G; T688C, A696T, A712G, and T714G; T688C, T702C, A712G, and T714G; or A696T, T702C, A712G, and T714G.

In some embodiments, the nucleotide sequence of a promoter element as provided herein can include five mutations as compared to the nucleotide sequence of a reference promoter element. For example, in some embodiments, five mutations corresponding to the following mutations relative to SEQ ID NO: 28 can be present in a promoter sequence: T688C, A696T, T702C, A712G, and T714G.

In some embodiments, the nucleotide sequence of a promoter element as provided herein can include two mutations as compared to the nucleotide sequence of a reference promoter element. For example, in some embodiments, two mutations corresponding to the following mutations relative to SEQ ID NO: 28 can be present in a promoter sequence: 146C and 154T; 146C and 303C; 146C and 426A; 146C and 433T; 146C and 435G; 146C and 530A; 146C and 572T; 146C and 596C; 146C and 617C; 146C and 688C; 146C and 696T; 146C and 702C; 146C and 709G; 146C and 712G; 146C and 714G; 146C and 790G; 146C and A841T; 146C and 862A; 154T and 303C; 154T and 426A; 154T and 433T; 154T and 435G; 154T and 530A; 154T and 572T; 154T and 596C; 154T and 617C; 154T and 688C; 154T and 696T; 154T and 702C; 154T and 709G; 154T and 712G; 154T and 714G; 154T and 790G; 154T and A841T; 154T and 862A; 303C and 426A; 303C and 433T; 303C and 435G; 303C and 530A; 303C and 572T; 303C and 596C; 303C and 617C; 303C and 688C; 303C and 696T; 303C and 702C; 303C and 709G; 303C and 712G; 303C and 714G; 303C and 790G; 303C and A841T; 303C and 862A; 426A and 433T; 426A and 435G; 426A and 530A; 426A and 572T; 426A and 596C; 426A and 617C; 426A and 688C; 426A and 696T; 426A and 702C; 426A and 709G; 426A and 712G; 426A and 714G; 426A and 790G; 426A and A841T; 426A and 862A; 433T and 435G; 433T and 530A; 433T and 572T; 433T and 596C; 433T and 617C; 433T and 688C; 433T and 696T; 433T and 702C; 433T and 709G; 433T and 712G; 433T and 714G; 433T and 790G; 433T and A841T; 433T and 862A; 435G and 530A; 435G and 572T; 435G and 596C; 435G and 617C; 435G and 688C; 435G and 696T; 435G and 702C; 435G and 709G; 435G and 712G; 435G and 714G; 435G and 790G; 435G and A841T; 435G and 862A; 530A and 572T; 530A and 596C; 530A and 617C; 530A and 688C; 530A and 696T; 530A and 702C; 530A and 709G; 530A and 712G; 530A and 714G; 530A and 790G; 530A and A841T; 530A and 862A; 572T and 596C; 572T and 617C; 572T and 688C; 572T and 696T; 572T and 702C; 572T and 709G; 572T and 712G; 572T and 714G; 572T and 790G; 572T and A841T; 572T and 862A; 596C and 617C; 596C and 688C; 596C and 696T; 596C and 702C; 596C and 709G; 596C and 712G; 596C and 714G; 596C and 790G; 596C and A841T; 596C and 862A; 617C and 688C; 617C and 696T; 617C and 702C; 617C and 709G; 617C and 712G; 617C and 714G; 617C and 790G; 617C and A841T; 617C and 862A; 688C and 696T; 688C and 702C; 688C and 709G; 688C and 712G; 688C and 714G; 688C and 790G; 688C and A841T; 688C and 862A; 696T and 702C; 696T and 709G; 696T and 712G; 696T and 714G; 696T and 790G; 696T and A841T; 696T and 862A; 702C and 709G; 702C and 712G; 702C and 714G; 702C and 790G; 702C and A841T; 702C and 862A; 709G and 712G; 709G and 714G; 709G and 790G; 709G and A841T; 709G and 862A; 712G and 714G; 712G and 790G; 712G and A841T; 712G and 862A; 714G and 790G; 714G and A841T; 714G and 862A; 790G and A841T; 790G and 862A; or A841T and 862A, as long as the indicated nucleobase is not the same as the corresponding naturally-occurring nucleobase.

In some embodiments, the nucleotide sequence of a promoter element as provided herein can include three mutations as compared to the nucleotide sequence of a reference promoter element. For example, in some embodiments, three mutations corresponding to the following mutations relative to SEQ ID NO: 28 can be present in a promoter sequence: 146C, 154T, and 303C; 146C, 154T, and 426A; 146C, 154T, and 433T; 146C, 154T, and 435G; 146C, 154T, and 530A; 146C, 154T, and 572T; 146C, 154T, and 596C; 146C, 154T, and 617C; 146C, 154T, and 688C; 146C, 154T, and 696T; 146C, 154T, and 702C; 146C, 154T, and 709G; 146C, 154T, and 712G; 146C, 154T, and 714G; 146C, 154T, and 790G; 146C, 154T, and A841T; 146C, 154T, and 862A; 146C, 303C, and 426A; 146C, 303C, and 433T; 146C, 303C, and 435G; 146C, 303C, and 530A; 146C, 303C, and 572T; 146C, 303C, and 596C; 146C, 303C, and 617C; 146C, 303C, and 688C; 146C, 303C, and 696T; 146C, 303C, and 702C; 146C, 303C, and 709G; 146C, 303C, and 712G; 146C, 303C, and 714G; 146C, 303C, and 790G; 146C, 303C, and A841T; 146C, 303C, and 862A; 146C, 426A, and 433T; 146C, 426A, and 435G; 146C, 426A, and 530A; 146C, 426A, and 572T; 146C, 426A, and 596C; 146C, 426A, and 617C; 146C, 426A, and 688C; 146C, 426A, and 696T; 146C, 426A, and 702C; 146C, 426A, and 709G; 146C, 426A, and 712G; 146C, 426A, and 714G; 146C, 426A, and 790G; 146C, 426A, and A841T; 146C, 426A, and 862A; 146C, 433T, and 435G; 146C, 433T, and 530A; 146C, 433T, and 572T; 146C, 433T, and 596C; 146C, 433T, and 617C; 146C, 433T, and 688C; 146C, 433T, and 696T; 146C, 433T, and 702C; 146C, 433T, and 709G; 146C, 433T, and 712G; 146C, 433T, and 714G; 146C, 433T, and 790G; 146C, 433T, and A841T; 146C, 433T, and 862A; 146C, 435G, and 530A; 146C, 435G, and 572T; 146C, 435G, and 596C; 146C, 435G, and 617C; 146C, 435G, and 688C; 146C, 435G, and 696T; 146C, 435G, and 702C; 146C, 435G, and 709G; 146C, 435G, and 712G; 146C, 435G, and 714G; 146C, 435G, and 790G; 146C, 435G, and A841T; 146C, 435G, and 862A; 146C, 530A, and 572T; 146C, 530A, and 596C; 146C, 530A, and 617C; 146C, 530A, and 688C; 146C, 530A, and 696T; 146C, 530A, and 702C; 146C, 530A, and 709G; 146C, 530A, and 712G; 146C, 530A, and 714G; 146C, 530A, and 790G; 146C, 530A, and A841T; 146C, 530A, and 862A; 146C, 572T, and 596C; 146C, 572T, and 617C; 146C, 572T, and 688C; 146C, 572T, and 696T; 146C, 572T, and 702C; 146C, 572T, and 709G; 146C, 572T, and 712G; 146C, 572T, and 714G; 146C, 572T, and 790G; 146C, 572T, and A841T; 146C, 572T, and 862A; 146C, 596C, and 617C; 146C, 596C, and 688C; 146C, 596C, and 696T; 146C, 596C, and 702C; 146C, 596C, and 709G; 146C, 596C, and 712G; 146C, 596C, and 714G; 146C, 596C, and 790G; 146C, 596C, and A841T; 146C, 596C, and 862A; 146C, 617C, and 688C; 146C, 617C, and 696T; 146C, 617C, and 702C; 146C, 617C, and 709G; 146C, 617C, and 712G; 146C, 617C, and 714G; 146C, 617C, and 790G; 146C, 617C, and A841T; 146C, 617C, and 862A; 146C, 688C, and 696T; 146C, 688C, and 702C; 146C, 688C, and 709G; 146C, 688C, and 712G; 146C, 688C, and 714G; 146C, 688C, and 790G; 146C, 688C, and A841T; 146C, 688C, and 862A; 146C, 696T, and 702C; 146C, 696T, and 709G; 146C, 696T, and 712G; 146C, 696T, and 714G; 146C, 696T, and 790G; 146C, 696T, and A841T; 146C, 696T, and 862A; 146C, 702C, and 709G; 146C, 702C, and 712G; 146C, 702C, and 714G; 146C, 702C, and 790G; 146C, 702C, and A841T; 146C, 702C, and 862A; 146C, 709G, and 712G; 146C, 709G, and 714G; 146C, 709G, and 790G; 146C, 709G, and A841T; 146C, 709G, and 862A; 146C, 712G, and 714G; 146C, 712G, and 790G; 146C, 712G, and A841T; 146C, 712G, and 862A; 146C, 714G, and 790G; 146C, 714G, and A841T; 146C, 714G, and 862A; 146C, 790G, and A841T; 146C, 790G, and 862A; 146C, A841T, and 862A; 154T, 303C, and 426A; 154T, 303C, and 433T; 154T, 303C, and 435G; 154T, 303C, and 530A; 154T, 303C, and 572T; 154T, 303C, and 596C; 154T, 303C, and 617C; 154T, 303C, and 688C; 154T, 303C, and 696T; 154T, 303C, and 702C; 154T, 303C, and 709G; 154T, 303C, and 712G; 154T, 303C, and 714G; 154T, 303C, and 790G; 154T, 303C, and A841T; 154T, 303C, and 862A; 154T, 426A, and 433T; 154T, 426A, and 435G; 154T, 426A, and 530A; 154T, 426A, and 572T; 154T, 426A, and 596C; 154T, 426A, and 617C; 154T, 426A, and 688C; 154T, 426A, and 696T; 154T, 426A, and 702C; 154T, 426A, and 709G; 154T, 426A, and 712G; 154T, 426A, and 714G; 154T, 426A, and 790G; 154T, 426A, and A841T; 154T, 426A, and 862A; 154T, 433T, and 435G; 154T, 433T, and 530A; 154T, 433T, and 572T; 154T, 433T, and 596C; 154T, 433T, and 617C; 154T, 433T, and 688C; 154T, 433T, and 696T; 154T, 433T, and 702C; 154T, 433T, and 709G; 154T, 433T, and 712G; 154T, 433T, and 714G; 154T, 433T, and 790G; 154T, 433T, and A841T; 154T, 433T, and 862A; 154T, 435G, and 530A; 154T, 435G, and 572T; 154T, 435G, and 596C; 154T, 435G, and 617C; 154T, 435G, and 688C; 154T, 435G, and 696T; 154T, 435G, and 702C; 154T, 435G, and 709G; 154T, 435G, and 712G; 154T, 435G, and 714G; 154T, 435G, and 790G; 154T, 435G, and A841T; 154T, 435G, and 862A; 154T, 530A, and 572T; 154T, 530A, and 596C; 154T, 530A, and 617C; 154T, 530A, and 688C; 154T, 530A, and 696T; 154T, 530A, and 702C; 154T, 530A, and 709G; 154T, 530A, and 712C; 154T, 530A, and 714G; 154T, 530A, and 790G; 154T, 530A, and A841T; 154T, 530A, and 862A; 154T, 572T, and 596C; 154T, 572T, and 617C; 154T, 572T, and 688C; 154T, 572T, and 696T; 154T, 572T, and 702C; 154T, 572T, and 709G; 154T, 572T, and 712G; 154T, 572T, and 714G; 154T, 572T, and 790G; 154T, 572T, and A841T; 154T, 572T, and 862A; 154T, 596C, and 617C; 154T, 596C, and 688C; 154T, 596C, and 696T; 154T, 596C, and 702C; 154T, 596C, and 709G; 154T, 596C, and 712G; 154T, 596C, and 714G; 154T, 596C, and 790G; 154T, 596C, and A841T; 154T, 596C, and 862A; 154T, 617C, and 688C; 154T, 617C, and 696T; 154T, 617C, and 702C; 154T, 617C, and 709G; 154T, 617C, and 712G; 154T, 617C, and 714G; 154T, 617C, and 790G; 154T, 617C, and A841T; 154T, 617C, and 862A; 154T, 688C, and 696T; 154T, 688C, and 702C; 154T, 688C, and 709G; 154T, 688C, and 712G; 154T, 688C, and 714G; 154T, 688C, and 790G; 154T, 688C, and A841T; 154T, 688C, and 862A; 154T, 696T, and 702C; 154T, 696T, and 709G; 154T, 696T, and 712G; 154T, 696T, and 714G; 154T, 696T, and 790G; 154T, 696T, and A841T; 154T, 696T, and 862A; 154T, 702C, and 709G; 154T, 702C, and 712G; 154T, 702C, and 714G; 154T, 702C, and 790G; 154T, 702C, and A841T; 154T, 702C, and 862A; 154T, 709G, and 712G; 154T, 709G, and 714G; 154T, 709G, and 790G; 154T, 709G, and A841T; 154T, 709G, and 862A; 154T, 712G, and 714G; 154T, 712G, and 790G; 154T, 712G, and A841T; 154T, 712G, and 862A; 154T, 714G, and 790G; 154T, 714G, and A841T; 154T, 714G, and 862A; 154T, 790G, and A841T; 154T, 790G, and 862A; 154T, A841T, and 862A; 303C, 426A, and 433T; 303C, 426A, and 435G; 303C, 426A, and 530A; 303C, 426A, and 572T; 303C, 426A, and 596C; 303C, 426A, and 617C; 303C, 426A, and 688C; 303C, 426A, and 696T; 303C, 426A, and 702C; 303C, 426A, and 709G; 303C, 426A, and 712G; 303C, 426A, and 714G; 303C, 426A, and 790G; 303C, 426A, and A841T; 303C, 426A, and 862A; 303C, 433T, and 435G; 303C, 433T, and 530A; 303C, 433T, and 572T; 303C, 433T, and 596C; 303C, 433T, and 617C; 303C, 433T, and 688C; 303C, 433T, and 696T; 303C, 433T, and 702C; 303C, 433T, and 709G; 303C, 433T, and 712G; 303C, 433T, and 714G; 303C, 433T, and 790G; 303C, 433T, and A841T; 303C, 433T, and 862A; 303C, 435G, and 530A; 303C, 435G, and 572T; 303C, 435G, and 596C; 303C, 435G, and 617C; 303C, 435G, and 688C; 303C, 435G, and 696T; 303C, 435G, and 702C; 303C, 435G, and 709G; 303C, 435G, and 712G; 303C, 435G, and 714G; 303C, 435G, and 790G; 303C, 435G, and A841T; 303C, 435G, and 862A; 303C, 530A, and 572T; 303C, 530A, and 596C; 303C, 530A, and 617C; 303C, 530A, and 688C; 303C, 530A, and 696T; 303C, 530A, and 702C; 303C, 530A, and 709G; 303C, 530A, and 712G; 303C, 530A, and 714G; 303C, 530A, and 790G; 303C, 530A, and A841T; 303C, 530A, and 862A; 303C, 572T, and 596C; 303C, 572T, and 617C; 303C, 572T, and 688C; 303C, 572T, and 696T; 303C, 572T, and 702C; 303C, 572T, and 709G; 303C, 572T, and 712G; 303C, 572T, and 714G; 303C, 572T, and 790G; 303C, 572T, and A841T; 303C, 572T, and 862A; 303C, 596C, and 617C; 303C, 596C, and 688C; 303C, 596C, and 696T; 303C, 596C, and 702C; 303C, 596C, and 709G; 303C, 596C, and 712G; 303C, 596C, and 714G; 303C, 596C, and 790G; 303C, 596C, and A841T; 303C, 596C, and 862A; 303C, 617C, and 688C; 303C, 617C, and 696T; 303C, 617C, and 702C; 303C, 617C, and 709G; 303C, 617C, and 712G; 303C, 617C, and 714G; 303C, 617C, and 790G; 303C, 617C, and A841T; 303C, 617C, and 862A; 303C, 688C, and 696T; 303C, 688C, and 702C; 303C, 688C, and 709G; 303C, 688C, and 712G; 303C, 688C, and 714G; 303C, 688C, and 790G; 303C, 688C, and A841T; 303C, 688C, and 862A; 303C, 696T, and 702C; 303C, 696T, and 709G; 303C, 696T, and 712G; 303C, 696T, and 714G; 303C, 696T, and 790G; 303C, 696T, and A841T; 303C, 696T, and 862A; 303C, 702C, and 709G; 303C, 702C, and 712G; 303C, 702C, and 714G; 303C, 702C, and 790G; 303C, 702C, and A841T; 303C, 702C, and 862A; 303C, 709G, and 712G; 303C, 709G, and 714G; 303C, 709G, and 790G; 303C, 709G, and A841T; 303C, 709G, and 862A; 303C, 712G, and 714G; 303C, 712G, and 790G; 303C, 712G, and A841T; 303C, 712G, and 862A; 303C, 714G, and 790G; 303C, 714G, and A841T; 303C, 714G, and 862A; 303C, 790G, and A841T; 303C, 790G, and 862A; 303C, A841T, and 862A; 426A, 433T, and 435G; 426A, 433T, and 530A; 426A, 433T, and 572T; 426A, 433T, and 596C; 426A, 433T, and 617C; 426A, 433T, and 688C; 426A, 433T, and 696T; 426A, 433T, and 702C; 426A, 433T, and 709G; 426A, 433T, and 712G; 426A, 433T, and 714G; 426A, 433T, and 790G; 426A, 433T, and A841T; 426A, 433T, and 862A; 426A, 435G, and 530A; 426A, 435G, and 572T; 426A, 435G, and 596C; 426A, 435G, and 617C; 426A, 435G, and 688C; 426A, 435G, and 696T; 426A, 435G, and 702C;

426A, 435G, and 709G; 426A, 435G, and 712G; 426A, 435G, and 714G; 426A, 435G, and 790G; 426A, 435G, and A841T; 426A, 435G, and 862A; 426A, 530A, and 572T; 426A, 530A, and 596C; 426A, 530A, and 617C; 426A, 530A, and 688C; 426A, 530A, and 696T; 426A, 530A, and 702C; 426A, 530A, and 709G; 426A, 530A, and 712G; 426A, 530A, and 714G; 426A, 530A, and 790G; 426A, 530A, and A841T; 426A, 530A, and 862A; 426A, 572T, and 596C; 426A, 572T, and 617C; 426A, 572T, and 688C; 426A, 572T, and 696T; 426A, 572T, and 702C; 426A, 572T, and 709G; 426A, 572T, and 712G; 426A, 572T, and 714G; 426A, 572T, and 790G; 426A, 572T, and A841T; 426A, 572T, and 862A; 426A, 596C, and 617C; 426A, 596C, and 688C; 426A, 596C, and 696T; 426A, 596C, and 702C; 426A, 596C, and 709G; 426A, 596C, and 712G; 426A, 596C, and 714G; 426A, 596C, and 790G; 426A, 596C, and A841T; 426A, 596C, and 862A; 426A, 617C, and 688C; 426A, 617C, and 696T; 426A, 617C, and 702C; 426A, 617C, and 709G; 426A, 617C, and 712G; 426A, 617C, and 714G; 426A, 617C, and 790G; 426A, 617C, and A841T; 426A, 617C, and 862A; 426A, 688C, and 696T; 426A, 688C, and 702C; 426A, 688C, and 709G; 426A, 688C, and 712G; 426A, 688C, and 714G; 426A, 688C, and 790G; 426A, 688C, and A841T; 426A, 688C, and 862A; 426A, 696T, and 702C; 426A, 696T, and 709G; 426A, 696T, and 712G; 426A, 696T, and 714G; 426A, 696T, and 790G; 426A, 696T, and A841T; 426A, 696T, and 862A; 426A, 702C, and 709G; 426A, 702C, and 712G; 426A, 702C, and 714G; 426A, 702C, and 790G; 426A, 702C, and A841T; 426A, 702C, and 862A; 426A, 709G, and 712G; 426A, 709G, and 714G; 426A, 709G, and 790G; 426A, 709G, and A841T; 426A, 709G, and 862A; 426A, 712G, and 714G; 426A, 712G, and 790G; 426A, 712G, and A841T; 426A, 712G, and 862A; 426A, 714G, and 790G; 426A, 714G, and A841T; 426A, 714G, and 862A; 426A, 790G, and A841T; 426A, 790G, and 862A; 426A, A841T, and 862A; 433T, 435G, and 530A; 433T, 435G, and 572T; 433T, 435G, and 596C; 433T, 435G, and 617C; 433T, 435G, and 688C; 433T, 435G, and 696T; 433T, 435G, and 702C; 433T, 435G, and 709G; 433T, 435G, and 712G; 433T, 435G, and 714G; 433T, 435G, and 790G; 433T, 435G, and A841T; 433T, 435G, and 862A; 433T, 530A, and 572T; 433T, 530A, and 596C; 433T, 530A, and 617C; 433T, 530A, and 688C; 433T, 530A, and 696T; 433T, 530A, and 702C; 433T, 530A, and 709G; 433T, 530A, and 712G; 433T, 530A, and 714G; 433T, 530A, and 790G; 433T, 530A, and A841T; 433T, 530A, and 862A; 433T, 572T, and 596C; 433T, 572T, and 617C; 433T, 572T, and 688C; 433T, 572T, and 696T; 433T, 572T, and 702C; 433T, 572T, and 709G; 433T, 572T, and 712G; 433T, 572T, and 714G; 433T, 572T, and 790G; 433T, 572T, and A841T; 433T, 572T, and 862A; 433T, 596C, and 617C; 433T, 596C, and 688C; 433T, 596C, and 696T; 433T, 596C, and 702C; 433T, 596C, and 709G; 433T, 596C, and 712G; 433T, 596C, and 714G; 433T, 596C, and 790G; 433T, 596C, and A841T; 433T, 596C, and 862A; 433T, 617C, and 688C; 433T, 617C, and 696T; 433T, 617C, and 702C; 433T, 617C, and 709G; 433T, 617C, and 712G; 433T, 617C, and 714G; 433T, 617C, and 790G; 433T, 617C, and A841T; 433T, 617C, and 862A; 433T, 688C, and 696T; 433T, 688C, and 702C; 433T, 688C, and 709G; 433T, 688C, and 712G; 433T, 688C, and 714G; 433T, 688C, and 790G; 433T, 688C, and A841T; 433T, 688C, and 862A; 433T, 696T, and 702C; 433T, 696T, and 709G; 433T, 696T, and 712G; 433T, 696T, and 714G; 433T, 696T, and 790G; 433T, 696T, and A841T; 433T, 696T, and 862A; 433T, 702C, and 709G; 433T, 702C, and 712G; 433T, 702C, and 714G; 433T, 702C, and 790G; 433T, 702C, and A841T; 433T, 702C, and 862A; 433T, 709G, and 712G; 433T, 709G, and 714G; 433T, 709G, and 790G; 433T, 709G, and A841T; 433T, 709G, and 862A; 433T, 712G, and 714G; 433T, 712G, and 790G; 433T, 712G, and A841T; 433T, 712G, and 862A; 433T, 714G, and 790G; 433T, 714G, and A841T; 433T, 714G, and 862A; 433T, 790G, and A841T; 433T, 790G, and 862A; 433T, A841T, and 862A; 435G, 530A, and 572T; 435G, 530A, and 596C; 435G, 530A, and 617C; 435G, 530A, and 688C; 435G, 530A, and 696T; 435G, 530A, and 702C; 435G, 530A, and 709G; 435G, 530A, and 712G; 435G, 530A, and 714G; 435G, 530A, and 790G; 435G, 530A, and A841T; 435G, 530A, and 862A; 435G, 572T, and 596C; 435G, 572T, and 617C; 435G, 572T, and 688C; 435G, 572T, and 696T; 435G, 572T, and 702C; 435G, 572T, and 709G; 435G, 572T, and 712G; 435G, 572T, and 714G; 435G, 572T, and 790G; 435G, 572T, and A841T; 435G, 572T, and 862A; 435G, 596C, and 617C; 435G, 596C, and 688C; 435G, 596C, and 696T; 435G, 596C, and 702C; 435G, 596C, and 709G; 435G, 596C, and 712G; 435G, 596C, and 714G; 435G, 596C, and 790G; 435G, 596C, and A841T; 435G, 596C, and 862A; 435G, 617C, and 688C; 435G, 617C, and 696T; 435G, 617C, and 702C; 435G, 617C, and 709G; 435G, 617C, and 712G; 435G, 617C, and 714G; 435G, 617C, and 790G; 435G, 617C, and A841T; 435G, 617C, and 862A; 435G, 688C, and 696T; 435G, 688C, and 702C; 435G, 688C, and 709G; 435G, 688C, and 712G; 435G, 688C, and 714G; 435G, 688C, and 790G; 435G, 688C, and A841T; 435G, 688C, and 862A; 435G, 696T, and 702C; 435G, 696T, and 709G; 435G, 696T, and 712G; 435G, 696T, and 714G; 435G, 696T, and 790G; 435G, 696T, and A841T; 435G, 696T, and 862A; 435G, 702C, and 709G; 435G, 702C, and 712G; 435G, 702C, and 714G; 435G, 702C, and 790G; 435G, 702C, and A841T; 435G, 702C, and 862A; 435G, 709G, and 712G; 435G, 709G, and 714G; 435G, 709G, and 790G; 435G, 709G, and A841T; 435G, 709G, and 862A; 435G, 712G, and 714G; 435G, 712G, and 790G; 435G, 712G, and A841T; 435G, 712G, and 862A; 435G, 714G, and 790G; 435G, 714G, and A841T; 435G, 714G, and 862A; 435G, 790G, and A841T; 435G, 790G, and 862A; 435G, A841T, and 862A; 530A, 572T, and 596C; 530A, 572T, and 617C; 530A, 572T, and 688C; 530A, 572T, and 696T; 530A, 572T, and 702C; 530A, 572T, and 709G; 530A, 572T, and 712G; 530A, 572T, and 714G; 530A, 572T, and 790G; 530A, 572T, and A841T; 530A, 572T, and 862A; 530A, 596C, and 617C; 530A, 596C, and 688C; 530A, 596C, and 696T; 530A, 596C, and 702C; 530A, 596C, and 709G; 530A, 596C, and 712G; 530A, 596C, and 714G; 530A, 596C, and 790G; 530A, 596C, and A841T; 530A, 596C, and 862A; 530A, 617C, and 688C; 530A, 617C, and 696T; 530A, 617C, and 702C; 530A, 617C, and 709G; 530A, 617C, and 712G; 530A, 617C, and 714G; 530A, 617C, and 790G; 530A, 617C, and A841T; 530A, 617C, and 862A; 530A, 688C, and 696T; 530A, 688C, and 702C; 530A, 688C, and 709G; 530A, 688C, and 712G; 530A, 688C, and 714G; 530A, 688C, and 790G; 530A, 688C, and A841T; 530A, 688C, and 862A; 530A, 696T, and 702C; 530A, 696T, and 709G; 530A, 696T, and 712G; 530A, 696T, and 714G; 530A, 696T, and 790G; 530A, 696T, and A841T; 530A, 696T, and 862A; 530A, 702C, and 709G; 530A, 702C, and 712G; 530A, 702C, and 714G; 530A, 702C, and 790G; 530A, 702C, and A841T; 530A, 702C, and 862A; 530A, 709G, and 712G; 530A, 709G, and 714G; 530A, 709G, and 790G; 530A, 709G, and A841T; 530A, 709G, and 862A; 530A, 712G, and 714G; 530A, 712G, and 790G; 530A, 712G, and A841T; 530A, 712G, and 862A; 530A, 714G, and 790G; 530A, 714G, and A841T; 530A, 714G, and 862A; 530A, 790G, and A841T; 530A, 790G, and 862A; 530A, A841T, and 862A; 572T, 596C, and 617C; 572T, 596C, and 688C; 572T, 596C, and 696T; 572T, 596C, and 702C; 572T, 596C, and 709G; 572T, 596C, and 712G; 572T, 596C, and 714G; 572T, 596C, and 790G; 572T, 596C, and A841T; 572T, 596C, and 862A; 572T, 617C, and 688C; 572T, 617C, and 696T; 572T, 617C, and 702C; 572T, 617C, and 709G; 572T, 617C, and 712G; 572T, 617C, and 714G; 572T, 617C, and 790G; 572T, 617C, and A841T; 572T, 617C, and 862A; 572T, 688C, and 696T; 572T, 688C, and 702C; 572T, 688C, and 709G; 572T, 688C, and 712G; 572T, 688C, and 714G; 572T, 688C, and 790G; 572T, 688C, and A841T; 572T, 688C, and 862A; 572T, 696T, and 702C; 572T, 696T, and 709G; 572T, 696T, and 712G; 572T, 696T, and 714G; 572T, 696T, and 790G; 572T, 696T, and A841T; 572T, 696T, and 862A; 572T, 702C, and 709G; 572T, 702C, and 712G; 572T, 702C, and 714G; 572T, 702C, and 790G; 572T, 702C, and A841T; 572T, 702C, and 862A; 572T, 709G, and 712G; 572T, 709G, and 714G; 572T, 709G, and 790G; 572T, 709G, and A841T; 572T, 709G, and 862A; 572T, 712G, and 714G; 572T, 712G, and 790G; 572T, 712G, and A841T; 572T, 712G, and 862A; 572T, 714G, and 790G; 572T, 714G, and A841T; 572T, 714G, and 862A; 572T, 790G, and A841T; 572T, 790G, and 862A; 572T, A841T, and 862A; 596C, 617C, and 688C; 596C, 617C, and 696T; 596C, 617C, and 702C; 596C, 617C, and 709G; 596C, 617C, and 712G; 596C, 617C, and 714G; 596C, 617C, and 790G; 596C, 617C, and A841T; 596C, 617C, and 862A; 596C, 688C, and 696T; 596C, 688C, and 702C; 596C, 688C, and 709G; 596C, 688C, and 712G; 596C, 688C, and 714G; 596C, 688C, and 790G; 596C, 688C, and A841T; 596C, 688C, and 862A; 596C, 696T, and 702C; 596C, 696T, and 709G; 596C, 696T, and 712G; 596C, 696T, and 714G; 596C, 696T, and 790G; 596C, 696T, and A841T; 596C, 696T, and 862A; 596C, 702C, and 709G; 596C, 702C, and 712G; 596C, 702C, and 714G; 596C, 702C, and 790G; 596C, 702C, and A841T; 596C, 702C, and 862A; 596C, 709G, and 712G; 596C, 709G, and 714G; 596C, 709G, and 790G; 596C, 709G, and A841T; 596C, 709G, and 862A; 596C, 712G, and 714G; 596C, 712G, and 790G; 596C, 712G, and A841T; 596C, 712G, and 862A; 596C, 714G, and 790G; 596C, 714G, and A841T; 596C, 714G, and 862A; 596C, 790G, and A841T; 596C, 790G, and 862A; 596C, A841T, and 862A; 617C, 688C, and 696T; 617C, 688C, and 702C; 617C, 688C, and 709G; 617C, 688C, and 712G; 617C, 688C, and 714G; 617C, 688C, and 790G; 617C, 688C, and A841T; 617C, 688C, and 862A; 617C, 696T, and 702C; 617C, 696T, and 709G; 617C, 696T, and 712G; 617C, 696T, and 714G; 617C, 696T, and 790G; 617C, 696T, and A841T; 617C, 696T, and 862A; 617C, 702C, and 709G; 617C, 702C, and 712G; 617C, 702C, and 714G; 617C, 702C, and 790G; 617C, 702C, and A841T; 617C, 702C, and 862A; 617C, 709G, and 712G; 617C, 709G, and 714G; 617C, 709G, and 790G; 617C, 709G, and A841T; 617C, 709G, and 862A; 617C, 712G, and 714G; 617C, 712G, and 790G; 617C, 712G, and A841T; 617C, 712G, and 862A; 617C, 714G, and 790G; 617C, 714G, and A841T; 617C, 714G, and 862A; 617C, 790G, and A841T; 617C, 790G, and 862A; 617C, A841T, and 862A; 688C, 696T, and 702C; 688C, 696T, and 709G; 688C, 696T, and 712G; 688C, 696T, and 714G; 688C, 696T, and 790G; 688C, 696T, and A841T; 688C, 696T, and 862A; 688C, 702C, and 709G; 688C, 702C, and 712G; 688C, 702C, and 714G; 688C, 702C, and 790G; 688C, 702C, and A841T; 688C, 702C, and 862A; 688C, 709G, and 712G; 688C, 709G, and 714G; 688C, 709G, and 790G; 688C, 709G, and A841T; 688C, 709G, and 862A; 688C, 712G, and 714G; 688C, 712G, and 790G; 688C, 712G, and A841T; 688C, 712G, and 862A; 688C, 714G, and 790G; 688C, 714G, and A841T; 688C, 714G, and 862A; 688C, 790G, and A841T; 688C, 790G, and 862A; 688C, A841T, and 862A; 696T, 702C, and 709G; 696T, 702C, and 712G; 696T, 702C, and 714G; 696T, 702C, and 790G; 696T, 702C, and A841T; 696T, 702C, and 862A; 696T, 709G, and 712G; 696T, 709G, and 714G; 696T, 709G, and 790G; 696T, 709G, and A841T; 696T, 709G, and 862A; 696T, 712G, and 714G; 696T, 712G, and 790G; 696T, 712G, and A841T; 696T, 712G, and 862A; 696T, 714G, and 790G; 696T, 714G, and A841T; 696T, 714G, and 862A; 696T, 790G, and A841T; 696T, 790G, and 862A; 696T, A841T, and 862A; 702C, 709G, and 712G; 702C, 709G, and 714G; 702C, 709G, and 790G; 702C, 709G, and A841T; 702C, 709G, and 862A; 702C, 712G, and 714G; 702C, 712G, and 790G; 702C, 712G, and A841T; 702C, 712G, and 862A; 702C, 714G, and 790G; 702C, 714G, and A841T; 702C, 714G, and 862A; 702C, 790G, and A841T; 702C, 790G, and 862A; 702C, A841T, and 862A; 709G, 712G, and 714G; 709G, 712G, and 790G; 709G, 712G, and A841T; 709G, 712G, and 862A; 709G, 714G, and 790G; 709G, 714G, and A841T; 709G, 714G, and 862A; 709G, 790G, and A841T; 709G, 790G, and 862A; 709G, A841T, and 862A; 712G, 714G, and 790G; 712G, 714G, and A841T; 712G, 714G, and 862A; 712G, 790G, and A841T; 712G, 790G, and 862A; 712G, A841T, and 862A; 714G, 790G, and A841T; 714G, 790G, and 862A; 714G, A841T, and 862A; or 790G, A841T, and 862A, as long as the indicated nucleobase is not the same as the corresponding naturally-occurring nucleobase.

In some embodiments, the nucleotide sequence of a promoter element as provided herein can include two mutations as compared to the nucleotide sequence of a reference promoter element. For example, in some embodiments, two mutations corresponding to the following mutations relative to SEQ ID NO: 28 can be present in a promoter sequence: 688C and 696T; 688C and 702C; 688C and 712G; 688C and 714G; 696T and 702C; 696T and 712G; 696T and 714G; 702C and 712G; 702C and 714G; or 712G and 714G, as long as the indicated nucleobase is not the same as the corresponding naturally-occurring nucleobase.

In some embodiments, the nucleotide sequence of a promoter element as provided herein can include three mutations as compared to the nucleotide sequence of a reference promoter element. For example, in some embodiments, three mutations corresponding to the following mutations relative to SEQ ID NO: 28 can be present in a promoter sequence: 688C, 696T, and 702C; 688C, 696T, and 712G; 688C, 696T, and 714G; 688C, 702C, and 712G; 688C, 702C, and 714G; 688C, 712G, and 714G; 696T, 702C, and 712G; 696T, 702C, and 714G; 696T, 712G, and 714G; or 702C, 712G, and 714G, as long as the indicated nucleobase is not the same as the corresponding naturally-occurring nucleobase.

In some embodiments, the nucleotide sequence of a promoter element as provided herein can include four mutations as compared to the nucleotide sequence of a reference promoter element. For example, in some embodiments, four mutations corresponding to the following mutations relative to SEQ ID NO: 28 can be present in a promoter sequence: 688C, 696T, 702C, and 712G; 688C, 696T, 702C, and 714G; 688C, 696T, 712G, and 714G; 688C, 702C, 712G, and 714G; or 696T, 702C, 712G, and 714G, as long as the indicated nucleobase is not the same as the corresponding naturally-occurring nucleobase.

In some embodiments, the nucleotide sequence of a promoter element as provided herein can include five mutations as compared to the nucleotide sequence of a reference promoter element. For example, in some embodiments, five mutations corresponding to the following mutations relative to SEQ ID NO: 28 can be present in a promoter sequence: 688C, 696T, 702C, 712G, and 714G, as long as the indicated nucleobase is not the same as the corresponding naturally-occurring nucleobase.

In some embodiments, the nucleotide sequence of a promoter element as provided herein can include two mutations as compared to the nucleotide sequence of a reference promoter element. For example, in some embodiments, two mutations at positions corresponding to the following positions relative to SEQ ID NO: 28 can be present in a promoter sequence: T146 and C154; T146 and T303; T146 and T426; T146 and A433; T146 and A435; T146 and T530; T146 and C572; T146 and T596; T146 and T617; T146 and T688; T146 and A696; T146 and T702; T146 and A709; T146 and A712; T146 and T714; T146 and A790; T146 and A841; T146 and T862; C154 and T303; C154 and T426; C154 and A433; C154 and A435; C154 and T530; C154 and C572; C154 and T596; C154 and T617; C154 and T688; C154 and A696; C154 and T702; C154 and A709; C154 and A712; C154 and T714; C154 and A790; C154 and A841; C154 and T862; T303 and T426; T303 and A433; T303 and A435; T303 and T530; T303 and C572; T303 and T596; T303 and T617; T303 and T688; T303 and A696; T303 and T702; T303 and A709; T303 and A712; T303 and T714; T303 and A790; T303 and A841; T303 and T862; T426 and A433; T426 and A435; T426 and T530; T426 and C572; T426 and T596; T426 and T617; T426 and T688; T426 and A696; T426 and T702; T426 and A709; T426 and A712; T426 and T714; T426 and A790; T426 and A841; T426 and T862; A433 and A435; A433 and T530; A433 and C572; A433 and T596; A433 and T617; A433 and T688; A433 and A696; A433 and T702; A433 and A709; A433 and A712; A433 and T714; A433 and A790; A433 and A841; A433 and T862; A435 and T530; A435 and C572; A435 and T596; A435 and T617; A435 and T688; A435 and A696; A435 and T702; A435 and A709; A435 and A712; A435 and T714; A435 and A790; A435 and A841; A435 and T862; T530 and C572; T530 and T596; T530 and T617; T530 and T688; T530 and A696; T530 and T702; T530 and A709; T530 and A712; T530 and T714; T530 and A790; T530 and A841; T530 and T862; C572 and T596; C572 and T617; C572 and T688; C572 and A696; C572 and T702; C572 and A709; C572 and A712; C572 and T714; C572 and A790; C572 and A841; C572 and T862; T596 and T617; T596 and T688; T596 and A696; T596 and T702; T596 and A709; T596 and A712; T596 and T714; T596 and A790; T596 and A841; T596 and T862; T617 and T688; T617 and A696; T617 and T702; T617 and A709; T617 and A712; T617 and T714; T617 and A790; T617 and A841; T617 and T862; T688 and A696; T688 and T702; T688 and A709; T688 and A712; T688 and T714; T688 and A790; T688 and A841; T688 and T862; A696 and T702; A696 and A709; A696 and A712; A696 and T714; A696 and A790; A696 and A841; A696 and T862; T702 and A709; T702 and A712; T702 and T714; T702 and A790; T702 and A841; T702 and T862; A709 and A712; A709 and T714; A709 and A790; A709 and A841; A709 and T862; A712 and T714; A712 and A790; A712 and A841; A712 and T862; T714 and A790; T714 and A841; T714 and T862; A790 and A841; A790 and T862; or A841 and T862.

In some embodiments, the nucleotide sequence of a promoter element as provided herein can include three mutations as compared to the nucleotide sequence of a reference promoter element. For example, in some embodiments, three mutations at positions corresponding to the following positions relative to SEQ ID NO: 28 can be present in a promoter sequence: T146, C154, and T303; T146, C154, and T426; T146, C154, and A433; T146, C154, and A435; T146, C154, and T530; T146, C154, and C572; T146, C154, and T596; T146, C154, and T617; T146, C154, and T688; T146, C154, and A696; T146, C154, and T702; T146, C154, and A709; T146, C154, and A712; T146, C154, and T714; T146, C154, and A790; T146, C154, and A841; T146, C154, and T862; T146, T303, and T426; T146, T303, and A433; T146, T303, and A435; T146, T303, and T530; T146, T303, and C572; T146, T303, and T596; T146, T303, and T617; T146, T303, and T688; T146, T303, and A696; T146, T303, and T702; T146, T303, and A709; T146, T303, and A712; T146, T303, and T714; T146, T303, and A790; T146, T303, and A841; T146, T303, and T862; T146, T426, and A433; T146, T426, and A435; T146, T426, and T530; T146, T426, and C572; T146, T426, and T596; T146, T426, and T617; T146, T426, and T688; T146, T426, and A696; T146, T426, and T702; T146, T426, and A709; T146, T426, and A712; T146, T426, and T714; T146, T426, and A790; T146, T426, and A841; T146, T426, and T862; T146, A433, and A435; T146, A433, and T530; T146, A433, and C572; T146, A433, and T596; T146, A433, and T617; T146, A433, and T688; T146, A433, and A696; T146, A433, and T702; T146, A433, and A709; T146, A433, and A712; T146, A433, and T714; T146, A433, and A790; T146, A433, and A841; T146, A433, and T862; T146, A435, and T530; T146, A435, and C572; T146, A435, and T596; T146, A435, and T617; T146, A435, and T688; T146, A435, and A696; T146, A435, and T702; T146, A435, and A709; T146, A435, and A712; T146, A435, and T714; T146, A435, and A790; T146, A435, and A841; T146, A435, and T862; T146, T530, and C572; T146, T530, and T596; T146, T530, and T617; T146, T530, and T688; T146, T530, and A696; T146, T530, and T702; T146, T530, and A709; T146, T530, and A712; T146, T530, and T714; T146, T530, and A790; T146, T530, and A841; T146, T530, and T862; T146, C572, and T596; T146, C572, and T617; T146, C572, and T688; T146, C572, and A696; T146, C572, and T702; T146, C572, and A709; T146, C572, and A712; T146, C572, and T714; T146, C572, and A790; T146, C572, and A841; T146, C572, and T862; T146, T596, and T617; T146, T596, and T688; T146, T596, and A696; T146, T596, and T702; T146, T596, and A709; T146, T596, and A712; T146, T596, and T714; T146, T596, and A790; T146, T596, and A841; T146, T596, and T862; T146, T617, and T688; T146, T617, and A696; T146, T617, and T702; T146, T617, and A709; T146, T617, and A712; T146, T617, and T714; T146, T617, and A790; T146, T617, and A841; T146, T617, and T862; T146, T688, and A696; T146, T688, and T702; T146, T688, and A709; T146, T688, and A712; T146, T688, and T714; T146, T688, and A790; T146, T688, and A841; T146, T688, and T862; T146, A696, and T702; T146, A696, and A709; T146, A696, and A712; T146, A696, and T714; T146, A696, and A790; T146, A696, and A841; T146, A696, and T862; T146, T702, and A709; T146, T702, and A712; T146, T702, and T714; T146, T702, and A790; T146, T702, and A841; T146, T702, and T862; T146, A709, and A712; T146, A709, and T714; T146, A709, and A790; T146, A709, and A841; T146, A709, and T862; T146, A712, and T714; T146, A712, and A790; T146, A712, and A841; T146, A712, and T862; T146, T714, and A790; T146, T714, and A841; T146, T714, and T862; T146, A790, and A841; T146, A790, and T862; T146, A841, and T862; C154, T303, and T426; C154, T303, and A433; C154, T303, and A435; C154, T303, and T530; C154, T303, and C572; C154, T303, and T596; C154, T303, and T617; C154, T303, and T688; C154, T303, and A696; C154, T303, and T702; C154, T303, and A709; C154, T303, and A712; C154, T303, and T714; C154, T303, and A790; C154, T303, and A841; C154, T303, and T862; C154, T426, and A433; C154, T426, and A435; C154, T426, and T530; C154, T426, and C572; C154, T426, and T596; C154, T426, and T617; C154, T426, and T688; C154, T426, and A696; C154, T426, and T702; C154, T426, and A709; C154, T426, and A712; C154, T426, and T714; C154, T426, and A790; C154, T426, and A841; C154, T426, and T862; C154, A433, and A435; C154, A433, and T530; C154, A433, and C572; C154, A433, and T596; C154, A433, and T617; C154, A433, and T688; C154, A433, and A696; C154, A433, and T702; C154, A433, and A709; C154, A433, and A712; C154, A433, and T714; C154, A433, and A790; C154, A433, and A841; C154, A433, and T862; C154, A435, and T530; C154, A435, and C572; C154, A435, and T596; C154, A435, and T617; C154, A435, and T688; C154, A435, and A696; C154, A435, and T702; C154, A435, and A709; C154, A435, and A712; C154, A435, and T714; C154, A435, and A790; C154, A435, and A841; C154, A435, and T862; C154, T530, and C572; C154, T530, and T596; C154, T530, and T617; C154, T530, and T688; C154, T530, and A696; C154, T530, and T702; C154, T530, and A709; C154, T530, and A712; C154, T530, and T714; C154, T530, and A790; C154, T530, and A841; C154, T530, and T862; C154, C572, and T596; C154, C572, and T617; C154, C572, and T688; C154, C572, and A696; C154, C572, and T702; C154, C572, and A709; C154, C572, and A712; C154, C572, and T714; C154, C572, and A790; C154, C572, and A841; C154, C572, and T862; C154, T596, and T617; C154, T596, and T688; C154, T596, and A696; C154, T596, and T702; C154, T596, and A709; C154, T596, and A712; C154, T596, and T714; C154, T596, and A790; C154, T596, and A841; C154, T596, and T862; C154, T617, and T688; C154, T617, and A696; C154, T617, and T702; C154, T617, and A709; C154, T617, and A712; C154, T617, and T714; C154, T617, and A790; C154, T617, and A841; C154, T617, and T862; C154, T688, and A696; C154, T688, and T702; C154, T688, and A709; C154, T688, and A712; C154, T688, and T714; C154, T688, and A790; C154, T688, and A841; C154, T688, and T862; C154, A696, and T702; C154, A696, and A709; C154, A696, and A712; C154, A696, and T714; C154, A696, and A790; C154, A696, and A841; C154, A696, and T862; C154, T702, and A709; C154, T702, and A712; C154, T702, and T714; C154, T702, and A790; C154, T702, and A841; C154, T702, and T862; C154, A709, and A712; C154, A709, and T714; C154, A709, and A790; C154, A709, and A841; C154, A709, and T862; C154, A712, and T714; C154, A712, and A790; C154, A712, and A841; C154, A712, and T862; C154, T714, and A790; C154, T714, and A841; C154, T714, and T862; C154, A790, and A841; C154, A790, and T862; C154, A841, and T862; T303, T426, and A433; T303, T426, and A435; T303, T426, and T530; T303, T426, and C572; T303, T426, and T596; T303, T426, and T617; T303, T426, and T688; T303, T426, and A696; T303, T426, and T702; T303, T426, and A709; T303, T426, and A712; T303, T426, and T714; T303, T426, and A790; T303, T426, and A841; T303, T426, and T862; T303, A433, and A435; T303, A433, and T530; T303, A433, and C572; T303, A433, and T596; T303, A433, and T617; T303, A433, and T688; T303, A433, and A696; T303, A433, and T702; T303, A433, and A709; T303, A433, and A712; T303, A433, and T714; T303, A433, and A790; T303, A433, and A841; T303, A433, and T862; T303, A435, and T530; T303, A435, and C572; T303, A435, and T596; T303, A435, and T617; T303, A435, and T688; T303, A435, and A696; T303, A435, and T702; T303, A435, and A709; T303, A435, and A712; T303, A435, and T714; T303, A435, and A790; T303, A435, and A841; T303, A435, and T862; T303, T530, and C572; T303, T530, and T596; T303, T530, and T617; T303, T530, and T688; T303, T530, and A696; T303, T530, and T702; T303, T530, and A709; T303, T530, and A712; T303, T530, and T714; T303, T530, and A790; T303, T530, and A841; T303, T530, and T862; T303, C572, and T596; T303, C572, and T617; T303, C572, and T688; T303, C572, and A696; T303, C572, and T702; T303, C572, and A709; T303, C572, and A712; T303, C572, and T714; T303, C572, and A790; T303, C572, and A841; T303, C572, and T862; T303, T596, and T617; T303, T596, and T688; T303, T596, and A696; T303, T596, and T702; T303, T596, and A709; T303, T596, and A712; T303, T596, and T714; T303, T596, and A790; T303, T596, and A841; T303, T596, and T862; T303, T617, and T688; T303, T617, and A696; T303, T617, and T702; T303, T617, and A709; T303, T617, and A712; T303, T617, and T714; T303, T617, and A790; T303, T617, and A841; T303, T617, and T862; T303, T688, and A696; T303, T688, and T702; T303, T688, and A709; T303, T688, and A712; T303, T688, and T714; T303, T688, and A790; T303, T688, and A841; T303, T688, and T862; T303, A696, and T702; T303, A696, and A709; T303, A696, and A712; T303, A696, and T714; T303, A696, and A790; T303, A696, and A841; T303, A696, and T862; T303, T702, and A709; T303, T702, and A712; T303, T702, and T714; T303, T702, and A790; T303, T702, and A841; T303, T702, and T862; T303, A709, and A712; T303, A709, and T714; T303, A709, and A790; T303, A709, and A841; T303, A709, and T862; T303, A712, and T714; T303, A712, and A790; T303, A712, and A841; T303, A712, and T862; T303, T714, and A790; T303, T714, and A841; T303, T714, and T862; T303, A790, and A841; T303, A790, and T862; T303, A841, and T862; T426, A433, and A435; T426, A433, and T530; T426, A433, and C572; T426, A433, and T596; T426, A433, and T617; T426, A433, and T688; T426, A433, and A696; T426, A433, and T702; T426, A433, and A709; T426, A433, and A712; T426, A433, and T714; T426, A433, and A790; T426, A433, and A841; T426, A433, and T862; T426, A435, and T530; T426, A435, and C572; T426, A435, and T596; T426, A435, and T617; T426, A435, and T688; T426, A435, and A696; T426, A435, and T702; T426, A435, and A709; T426, A435, and A712; T426, A435, and T714; T426, A435, and A790; T426, A435, and A841; T426, A435, and T862; T426, T530, and C572; T426, T530, and T596; T426, T530, and T617; T426, T530, and T688; T426, T530, and A696; T426, T530, and T702; T426, T530, and A709; T426, T530, and A712; T426, T530, and T714; T426, T530, and A790; T426, T530, and A841; T426, T530, and T862; T426, C572, and T596; T426, C572, and T617; T426, C572, and T688; T426, C572, and A696; T426, C572, and T702; T426, C572, and A709; T426, C572, and A712; T426, C572, and T714; T426, C572, and A790; T426, C572, and A841; T426, C572, and T862; T426, T596, and T617; T426, T596, and T688; T426, T596, and A696; T426, T596, and T702; T426, T596, and A709; T426, T596, and A712; T426, T596, and T714; T426, T596, and A790; T426, T596, and A841; T426, T596, and T862; T426, T617, and T688; T426, T617, and A696; T426, T617, and T702; T426, T617, and A709; T426, T617, and A712; T426, T617, and T714; T426, T617, and A790; T426, T617, and A841; T426, T617, and T862; T426, T688, and A696; T426, T688, and T702; T426, T688, and A709; T426, T688, and A712; T426, T688, and T714; T426, T688, and A790; T426, T688, and A841; T426, T688, and T862; T426, A696, and T702; T426, A696, and A709; T426, A696, and A712; T426, A696, and T714; T426, A696, and A790; T426, A696, and A841; T426, A696, and T862; T426, T702, and A709; T426, T702, and A712; T426, T702, and T714; T426, T702, and A790; T426, T702, and A841; T426, T702, and T862; T426, A709, and A712; T426, A709, and T714; T426, A709, and A790; T426, A709, and A841; T426, A709, and T862; T426, A712, and T714; T426, A712, and A790; T426, A712, and A841; T426, A712, and T862; T426, T714, and A790; T426, T714, and A841; T426, T714, and T862; T426, A790, and A841; T426, A790, and T862; T426, A841, and T862; A433, A435, and T530; A433, A435, and C572; A433, A435, and T596; A433, A435, and T617; A433, A435, and T688; A433, A435, and A696; A433, A435, and T702; A433, A435, and A709; A433, A435, and A712; A433, A435, and T714; A433, A435, and A790; A433, A435, and A841; A433, A435, and T862; A433, T530, and C572; A433, T530, and T596; A433, T530, and T617; A433, T530, and T688; A433, T530, and A696; A433, T530, and T702; A433, T530, and A709; A433, T530, and A712; A433, T530, and T714; A433, T530, and A790; A433, T530, and A841; A433, T530, and T862; A433, C572, and T596; A433, C572, and T617; A433, C572, and T688; A433, C572, and A696; A433, C572, and T702; A433, C572, and A709; A433, C572, and A712; A433, C572, and T714; A433, C572, and A790; A433, C572, and A841; A433, C572, and T862; A433, T596, and T617; A433, T596, and T688; A433, T596, and A696; A433, T596, and T702; A433, T596, and A709; A433, T596, and A712; A433, T596, and T714; A433, T596, and A790; A433, T596, and A841; A433, T596, and T862; A433, T617, and T688; A433, T617, and A696; A433, T617, and T702; A433, T617, and A709; A433, T617, and A712; A433, T617, and T714; A433, T617, and A790; A433, T617, and A841; A433, T617, and T862; A433, T688, and A696; A433, T688, and T702; A433, T688, and A709; A433, T688, and A712; A433, T688, and T714; A433, T688, and A790; A433, T688, and A841; A433, T688, and T862; A433, A696, and T702; A433, A696, and A709; A433, A696, and A712; A433, A696, and T714; A433, A696, and A790; A433, A696, and A841; A433, A696, and T862; A433, T702, and A709; A433, T702, and A712; A433, T702, and T714; A433, T702, and A790; A433, T702, and A841; A433, T702, and T862; A433, A709, and A712; A433, A709, and T714; A433, A709, and A790; A433, A709, and A841; A433, A709, and T862; A433, A712, and T714; A433, A712, and A790; A433, A712, and A841; A433, A712, and T862; A433, T714, and A790; A433, T714, and A841; A433, T714, and T862; A433, A790, and A841; A433, A790, and T862; A433, A841, and T862; A435, T530, and C572; A435, T530, and T596; A435, T530, and T617; A435, T530, and T688; A435, T530, and A696; A435, T530, and T702; A435, T530, and A709; A435, T530, and A712; A435, T530, and T714; A435, T530, and A790; A435, T530, and A841; A435, T530, and T862; A435, C572, and T596; A435, C572, and T617; A435, C572, and T688; A435, C572, and A696; A435, C572, and T702; A435, C572, and A709; A435, C572, and A712; A435, C572, and T714; A435, C572, and A790; A435, C572, and A841; A435, C572, and T862; A435, T596, and T617; A435, T596, and T688; A435, T596, and A696; A435, T596, and T702; A435, T596, and A709; A435, T596, and A712; A435, T596, and T714; A435, T596, and A790; A435, T596, and A841; A435, T596, and T862; A435, T617, and T688; A435, T617, and A696; A435, T617, and T702; A435, T617, and A709; A435, T617, and A712; A435, T617, and T714; A435, T617, and A790; A435, T617, and A841; A435, T617, and T862; A435, T688, and A696; A435, T688, and T702; A435, T688, and A709; A435, T688, and A712; A435, T688, and T714; A435, T688, and A790; A435, T688, and A841; A435, T688, and T862; A435, A696, and T702; A435, A696, and A709; A435, A696, and A712; A435, A696, and T714; A435, A696, and A790; A435, A696, and A841; A435, A696, and T862; A435, T702, and A709; A435, T702, and A712; A435, T702, and A790; A435, T702, and A841; A435, T702, and T862; A435, A709, and A712; A435, A709, and T714; A435, A709, and A790; A435, A709, and A841; A435, A709, and T862; A435, A712, and T714; A435, A712, and A790; A435, A712, and A841; A435, A712, and T862; A435, T714, and A790; A435, T714, and A841; A435, T714, and T862; A435, A790, and A841; A435, A790, and T862; A435, A841, and T862; T530, C572, and T596; T530, C572, and T617; T530, C572, and T688; T530, C572, and A696; T530, C572, and T702; T530, C572, and A709; T530, C572, and A712; T530, C572, and T714; T530, C572, and A790; T530, C572, and A841; T530, C572, and T862; T530, T596, and T617; T530, T596, and T688; T530, T596, and A696; T530, T596, and T702; T530, T596, and A709; T530, T596, and A712; T530, T596, and T714; T530, T596, and A790; T530, T596, and A841; T530, T596, and T862; T530, T617, and T688; T530, T617, and A696; T530, T617, and T702; T530, T617, and A709; T530, T617, and A712; T530, T617, and T714; T530, T617, and A790; T530, T617, and A841; T530, T617, and T862; T530, T688, and A696; T530, T688, and T702; T530, T688, and A709; T530, T688, and A712; T530, T688, and T714; T530, T688, and A790; T530, T688, and A841; T530, T688, and T862; T530, A696, and T702; T530, A696, and A709; T530, A696, and A712; T530, A696, and T714; T530, A696, and A790; T530, A696, and A841; T530, A696, and T862; T530, T702, and A709; T530, T702, and A712; T530, T702, and T714; T530, T702, and A790; T530, T702, and A841; T530, T702, and T862; T530, A709, and A712; T530, A709, and T714; T530, A709, and A790; T530, A709, and A841; T530, A709, and T862; T530, A712, and T714; T530, A712, and A790; T530, A712, and A841; T530, A712, and T862; T530, T714, and A790; T530, T714, and A841; T530, T714, and T862; T530, A790, and A841; T530, A790, and T862; T530, A841, and T862; C572, T596, and T617; C572, T596, and T688; C572, T596, and A696; C572, T596, and T702; C572, T596, and A709; C572, T596, and A712; C572, T596, and T714; C572, T596, and A790; C572, T596, and A841; C572, T596, and T862; C572, T617, and T688; C572, T617, and A696; C572, T617, and T702; C572, T617, and A709; C572, T617, and A712; C572, T617, and T714; C572, T617, and A790; C572, T617, and A841; C572, T617, and T862; C572, T688, and A696; C572, T688, and T702; C572, T688, and A709; C572, T688, and A712; C572, T688, and T714; C572, T688, and A790; C572, T688, and A841; C572, T688, and T862; C572, A696, and T702; C572, A696, and A709; C572, A696, and A712; C572, A696, and T714; C572, A696, and A790; C572, A696, and A841; C572, A696, and T862; C572, T702, and A709; C572, T702, and A712; C572, T702, and T714; C572, T702, and A790; C572, T702, and A841; C572, T702, and T862; C572, A709, and A712; C572, A709, and T714; C572, A709, and A790; C572, A709, and A841; C572, A709, and T862; C572, A712, and T714; C572, A712, and A790; C572, A712, and A841; C572, A712, and T862; C572, T714, and A790; C572, T714, and A841; C572, T714, and T862; C572, A790, and A841; C572, A790, and T862; C572, A841, and T862; T596, T617, and T688; T596, T617, and A696; T596, T617, and T702; T596, T617, and A709; T596, T617, and A712; T596, T617, and T714; T596, T617, and A790; T596, T617, and A841; T596, T617, and T862; T596, T688, and A696; T596, T688, and T702; T596, T688, and A709; T596, T688, and A712; T596, T688, and T714; T596, T688, and A790; T596, T688, and A841; T596, T688, and T862; T596, A696, and T702; T596, A696, and A709; T596, A696, and A712; T596, A696, and T714; T596, A696, and A790; T596, A696, and A841; T596, A696, and T862; T596, T702, and A709; T596, T702, and A712; T596, T702, and T714; T596, T702, and A790; T596, T702, and A841;

T596, T702, and T862; T596, A709, and A712; T596, A709, and T714; T596, A709, and A790; T596, A709, and A841; T596, A709, and T862; T596, A712, and T714; T596, A712, and A790; T596, A712, and A841; T596, A712, and T862; T596, T714, and A790; T596, T714, and A841; T596, T714, and T862; T596, A790, and A841; T596, A790, and T862; T596, A841, and T862; T617, T688, and A696; T617, T688, and T702; T617, T688, and A709; T617, T688, and A712; T617, T688, and T714; T617, T688, and A790; T617, T688, and A841; T617, T688, and T862; T617, A696, and T702; T617, A696, and A709; T617, A696, and A712; T617, A696, and T714; T617, A696, and A790; T617, A696, and A841; T617, A696, and T862; T617, T702, and A709; T617, T702, and A712; T617, T702, and T714; T617, T702, and A790; T617, T702, and A841; T617, T702, and T862; T617, A709, and A712; T617, A709, and T714; T617, A709, and A790; T617, A709, and A841; T617, A709, and T862; T617, A712, and T714; T617, A712, and A790; T617, A712, and A841; T617, A712, and T862; T617, T714, and A790; T617, T714, and A841; T617, T714, and T862; T617, A790, and A841; T617, A790, and T862; T617, A841, and T862; T688, A696, and T702; T688, A696, and A709; T688, A696, and A712; T688, A696, and T714; T688, A696, and A790; T688, A696, and A841; T688, A696, and T862; T688, T702, and A709; T688, T702, and A712; T688, T702, and T714; T688, T702, and A790; T688, T702, and A841; T688, T702, and T862; T688, A709, and A712; T688, A709, and T714; T688, A709, and A790; T688, A709, and A841; T688, A709, and T862; T688, A712, and T714; T688, A712, and A790; T688, A712, and A841; T688, A712, and T862; T688, T714, and A790; T688, T714, and A841; T688, T714, and T862; T688, A790, and A841; T688, A790, and T862; T688, A841, and T862; A696, T702, and A709; A696, T702, and A712; A696, T702, and T714; A696, T702, and A790; A696, T702, and A841; A696, T702, and T862; A696, A709, and A712; A696, A709, and T714; A696, A709, and A790; A696, A709, and A841; A696, A709, and T862; A696, A712, and T714; A696, A712, and A790; A696, A712, and A841; A696, A712, and T862; A696, T714, and A790; A696, T714, and A841; A696, T714, and T862; A696, A790, and A841; A696, A790, and T862; A696, A841, and T862; T702, A709, and A712; T702, A709, and T714; T702, A709, and A790; T702, A709, and A841; T702, A709, and T862; T702, A712, and T714; T702, A712, and A790; T702, A712, and A841; T702, A712, and T862; T702, T714, and A790; T702, T714, and A841; T702, T714, and T862; T702, A790, and A841; T702, A790, and T862; T702, A841, and T862; A709, A712, and T714; A709, A712, and A790; A709, A712, and A841; A709, A712, and T862; A709, T714, and A790; A709, T714, and A841; A709, T714, and T862; A709, A790, and A841; A709, A790, and T862; A709, A841, and T862; A712, T714, and A790; A712, T714, and A841; A712, T714, and T862; A712, A790, and A841; A712, A790, and T862; A712, A841, and T862; T714, A790, and A841; T714, A790, and T862; T714, A841, and T862; or A790, A841, and T862.

In some embodiments, the nucleotide sequence of a promoter element as provided herein can include two mutations as compared to the nucleotide sequence of a reference promoter element. For example, in some embodiments, two mutations at positions corresponding to the following positions relative to SEQ ID NO: 28 can be present in a promoter sequence: T688 and A696; T688 and T702; T688 and A712; T688 and T714; A696 and T702; A696 and A712; A696 and T714; T702 and A712; T702 and T714; or A712 and T714.

In some embodiments, the nucleotide sequence of a promoter element as provided herein can include three mutations as compared to the nucleotide sequence of a reference promoter element. For example, in some embodiments, three mutations at positions corresponding to the following positions relative to SEQ ID NO: 28 can be present in a promoter sequence: T688, A696, and T702; T688, A696, and A712; T688, A696, and T714; T688, T702, and A712; T688, T702, and T714; T688, A712, and T714; A696, T702, and A712; A696, T702, and T714; A696, A712, and T714; or T702, A712, and T714.

In some embodiments, the nucleotide sequence of a promoter element as provided herein can include four mutations as compared to the nucleotide sequence of a reference promoter element. For example, in some embodiments, four mutations at positions corresponding to the following positions relative to SEQ ID NO: 28 can be present in a promoter sequence: T688, A696, T702, and A712; T688, A696, T702, and T714; T688, A696, A712, and T714; T688, T702, A712, and T714; or A696, T702, A712, and T714.

In some embodiments, the nucleotide sequence of a promoter element as provided herein can include five mutations as compared to the nucleotide sequence of a reference promoter element. For example, in some embodiments, five mutations at positions corresponding to the following positions relative to SEQ ID NO: 28 can be present in a promoter sequence: T688, A696, T702, A712, and T714.

In some embodiments, the nucleotide sequence of a promoter element as provided herein can include two mutations as compared to the nucleotide sequence of a reference promoter element. For example, in some embodiments, two mutations at positions corresponding to the following positions relative to SEQ ID NO: 28 can be present in a promoter sequence: 146 and 154; 146 and 303; 146 and 426; 146 and 433; 146 and 435; 146 and 530; 146 and 572; 146 and 596; 146 and 617; 146 and 688; 146 and 696; 146 and 702; 146 and 709; 146 and A712; 146 and 714; 146 and 790; 146 and 841; 146 and 862; 154 and 303; 154 and 426; 154 and 433; 154 and 435; 154 and 530; 154 and 572; 154 and 596; 154 and 617; 154 and 688; 154 and 696; 154 and 702; 154 and 709; 154 and A712; 154 and 714; 154 and 790; 154 and 841; 154 and 862; 303 and 426; 303 and 433; 303 and 435; 303 and 530; 303 and 572; 303 and 596; 303 and 617; 303 and 688; 303 and 696; 303 and 702; 303 and 709; 303 and A712; 303 and 714; 303 and 790; 303 and 841; 303 and 862; 426 and 433; 426 and 435; 426 and 530; 426 and 572; 426 and 596; 426 and 617; 426 and 688; 426 and 696; 426 and 702; 426 and 709; 426 and A712; 426 and 714; 426 and 790; 426 and 841; 426 and 862; 433 and 435; 433 and 530; 433 and 572; 433 and 596; 433 and 617; 433 and 688; 433 and 696; 433 and 702; 433 and 709; 433 and A712; 433 and 714; 433 and 790; 433 and 841; 433 and 862; 435 and 530; 435 and 572; 435 and 596; 435 and 617; 435 and 688; 435 and 696; 435 and 702; 435 and 709; 435 and A712; 435 and 714; 435 and 790; 435 and 841; 435 and 862; 530 and 572; 530 and 596; 530 and 617; 530 and 688; 530 and 696; 530 and 702; 530 and 709; 530 and A712; 530 and 714; 530 and 790; 530 and 841; 530 and 862; 572 and 596; 572 and 617; 572 and 688; 572 and 696; 572 and 702; 572 and 709; 572 and A712; 572 and 714; 572 and 790; 572 and 841; 572 and 862; 596 and 617; 596 and 688; 596 and 696; 596 and 702; 596 and 709; 596 and A712; 596 and 714; 596 and 790; 596 and 841; 596 and 862; 617 and 688; 617 and 696; 617 and 702; 617 and 709; 617 and A712; 617 and 714; 617 and 790; 617 and 841; 617 and 862; 688 and 696; 688 and 702; 688 and 709; 688 and A712; 688 and 714; 688 and 790; 688 and 841; 688 and 862; 696 and 702; 696 and 709; 696 and A712; 696 and 714; 696 and 790; 696 and 841; 696 and 862; 702 and 709; 702 and A712; 702 and 714; 702 and 790; 702 and 841; 702 and 862; 709 and A712; 709 and 714; 709 and 790; 709 and 841; 709 and 862; A712 and 714; A712 and 790; A712 and 841; A712 and 862; 714 and 790; 714 and 841; 714 and 862; 790 and 841; 790 and 862; or 841 and 862.

In some embodiments, the nucleotide sequence of a promoter element as provided herein can include three mutations as compared to the nucleotide sequence of a reference promoter element. For example, in some embodiments, three mutations at positions corresponding to the following positions relative to SEQ ID NO: 28 can be present in a promoter sequence: 146, 154, and 303; 146, 154, and 426; 146, 154, and 433; 146, 154, and 435; 146, 154, and 530; 146, 154, and 572; 146, 154, and 596; 146, 154, and 617; 146, 154, and 688; 146, 154, and 696; 146, 154, and 702; 146, 154, and 709; 146, 154, and A712; 146, 154, and 714; 146, 154, and 790; 146, 154, and 841; 146, 154, and 862; 146, 303, and 426; 146, 303, and 433; 146, 303, and 435; 146, 303, and 530; 146, 303, and 572; 146, 303, and 596; 146, 303, and 617; 146, 303, and 688; 146, 303, and 696; 146, 303, and 702; 146, 303, and 709; 146, 303, and A712; 146, 303, and 714; 146, 303, and 790; 146, 303, and 841; 146, 303, and 862; 146, 426, and 433; 146, 426, and 435; 146, 426, and 530; 146, 426, and 572; 146, 426, and 596; 146, 426, and 617; 146, 426, and 688; 146, 426, and 696; 146, 426, and 702; 146, 426, and 709; 146, 426, and A712; 146, 426, and 714; 146, 426, and 790; 146, 426, and 841; 146, 426, and 862; 146, 433, and 435; 146, 433, and 530; 146, 433, and 572; 146, 433, and 596; 146, 433, and 617; 146, 433, and 688; 146, 433, and 696; 146, 433, and 702; 146, 433, and 709; 146, 433, and A712; 146, 433, and 714; 146, 433, and 790; 146, 433, and 841; 146, 433, and 862; 146, 435, and 530; 146, 435, and 572; 146, 435, and 596; 146, 435, and 617; 146, 435, and 688; 146, 435, and 696; 146, 435, and 702; 146, 435, and 709; 146, 435, and A712; 146, 435, and 714; 146, 435, and 790; 146, 435, and 841; 146, 435, and 862; 146, 530, and 572; 146, 530, and 596; 146, 530, and 617; 146, 530, and 688; 146, 530, and 696; 146, 530, and 702; 146, 530, and 709; 146, 530, and A712; 146, 530, and 714; 146, 530, and 790; 146, 530, and 841; 146, 530, and 862; 146, 572, and 596; 146, 572, and 617; 146, 572, and 688; 146, 572, and 696; 146, 572, and 702; 146, 572, and 709; 146, 572, and A712; 146, 572, and 714; 146, 572, and 790; 146, 572, and 841; 146, 572, and 862; 146, 596, and 617; 146, 596, and 688; 146, 596, and 696; 146, 596, and 702; 146, 596, and 709; 146, 596, and A712; 146, 596, and 714; 146, 596, and 790; 146, 596, and 841; 146, 596, and 862; 146, 617, and 688; 146, 617, and 696; 146, 617, and 702; 146, 617, and 709; 146, 617, and A712; 146, 617, and 714; 146, 617, and 790; 146, 617, and 841; 146, 617, and 862; 146, 688, and 696; 146, 688, and 702; 146, 688, and 709; 146, 688, and A712; 146, 688, and 714; 146, 688, and 790; 146, 688, and 841; 146, 688, and 862; 146, 696, and 702; 146, 696, and 709; 146, 696, and A712; 146, 696, and 714; 146, 696, and 790; 146, 696, and 841; 146, 696, and 862; 146, 702, and 709; 146, 702, and A712; 146, 702, and 714; 146, 702, and 790; 146, 702, and 841; 146, 702, and 862; 146, 709, and A712; 146, 709, and 714; 146, 709, and 790; 146, 709, and 841; 146, 709, and 862; 146, A712, and 714; 146, A712, and 790; 146, A712, and 841; 146, A712, and 862; 146, 714, and 790; 146, 714, and 841; 146, 714, and 862; 146, 790, and 841; 146, 790, and 862; 146, 841, and 862; 154, 303, and 426; 154, 303, and 433; 154, 303, and 435; 154, 303, and 530; 154, 303, and 572; 154, 303, and 596; 154, 303, and 617; 154, 303, and 688; 154, 303, and 696; 154, 303, and 702; 154, 303, and 709; 154, 303, and A712; 154, 303, and 714; 154, 303, and 790; 154, 303, and 841; 154, 303, and 862; 154, 426, and 433; 154, 426, and 435; 154, 426, and 530; 154, 426, and 572; 154, 426, and 596; 154, 426, and 617; 154, 426, and 688; 154, 426, and 696; 154, 426, and 702; 154, 426, and 709; 154, 426, and A712; 154, 426, and 714; 154, 426, and 790; 154, 426, and 841; 154, 426, and 862; 154, 433, and 435; 154, 433, and 530; 154, 433, and 572; 154, 433, and 596; 154, 433, and 617; 154, 433, and 688; 154, 433, and 696; 154, 433, and 702; 154, 433, and 709; 154, 433, and A712; 154, 433, and 714; 154, 433, and 790; 154, 433, and 841; 154, 433, and 862; 154, 435, and 530; 154, 435, and 572; 154, 435, and 596; 154, 435, and 617; 154, 435, and 688; 154, 435, and 696; 154, 435, and 702; 154, 435, and 709; 154, 435, and A712; 154, 435, and 714; 154, 435, and 790; 154, 435, and 841; 154, 435, and 862; 154, 530, and 572; 154, 530, and 596; 154, 530, and 617; 154, 530, and 688; 154, 530, and 696; 154, 530, and 702; 154, 530, and 709; 154, 530, and A712; 154, 530, and 714; 154, 530, and 790; 154, 530, and 841; 154, 530, and 862; 154, 572, and 596; 154, 572, and 617; 154, 572, and 688; 154, 572, and 696; 154, 572, and 702; 154, 572, and 709; 154, 572, and A712; 154, 572, and 714; 154, 572, and 790; 154, 572, and 841; 154, 572, and 862; 154, 596, and 617; 154, 596, and 688; 154, 596, and 696; 154, 596, and 702; 154, 596, and 709; 154, 596, and A712; 154, 596, and 714; 154, 596, and 790; 154, 596, and 841; 154, 596, and 862; 154, 617, and 688; 154, 617, and 696; 154, 617, and 702; 154, 617, and 709; 154, 617, and A712; 154, 617, and 714; 154, 617, and 790; 154, 617, and 841; 154, 617, and 862; 154, 688, and 696; 154, 688, and 702; 154, 688, and 709; 154, 688, and A712; 154, 688, and 714; 154, 688, and 790; 154, 688, and 841; 154, 688, and 862; 154, 696, and 702; 154, 696, and 709; 154, 696, and A712; 154, 696, and 714; 154, 696, and 790; 154, 696, and 841; 154, 696, and 862; 154, 702, and 709; 154, 702, and A712; 154, 702, and 714; 154, 702, and 790; 154, 702, and 841; 154, 702, and 862; 154, 709, and A712; 154, 709, and 714; 154, 709, and 790; 154, 709, and 841; 154, 709, and 862; 154, A712, and 714; 154, A712, and 790; 154, A712, and 841; 154, A712, and 862; 154, 714, and 790; 154, 714, and 841; 154, 714, and 862; 154, 790, and 841; 154, 790, and 862; 154, 841, and 862; 303, 426, and 433; 303, 426, and 435; 303, 426, and 530; 303, 426, and 572; 303, 426, and 596; 303, 426, and 617; 303, 426, and 688; 303, 426, and 696; 303, 426, and 702; 303, 426, and 709; 303, 426, and A712; 303, 426, and 714; 303, 426, and 790; 303, 426, and 841; 303, 426, and 862; 303, 433, and 435; 303, 433, and 530; 303, 433, and 572; 303, 433, and 596; 303, 433, and 617; 303, 433, and 688; 303, 433, and 696; 303, 433, and 702; 303, 433, and 709; 303, 433, and A712; 303, 433, and 714; 303, 433, and 790; 303, 433, and 841; 303, 433, and 862; 303, 435, and 530; 303, 435, and 572; 303, 435, and 596; 303, 435, and 617; 303, 435, and 688; 303, 435, and 696; 303, 435, and 702; 303, 435, and 709; 303, 435, and A712; 303, 435, and 714; 303, 435, and 790; 303, 435, and 841; 303, 435, and 862; 303, 530, and 572; 303, 530, and 596; 303, 530, and 617; 303, 530, and 688; 303, 530, and 696; 303, 530, and 702; 303, 530, and 709; 303, 530, and A712; 303, 530, and 714; 303, 530, and 790; 303, 530, and 841; 303, 530, and 862; 303, 572, and 596; 303, 572, and 617; 303, 572, and 688; 303, 572, and 696; 303, 572, and 702; 303, 572, and 709; 303, 572, and A712; 303, 572, and 714; 303, 572, and 790; 303, 572, and 841; 303, 572, and 862; 303, 596, and 617; 303, 596, and 688; 303, 596, and 696; 303, 596, and 702; 303, 596, and 709; 303, 596, and A712; 303, 596, and 714; 303, 596, and 790; 303, 596, and 841; 303, 596, and 862; 303, 617, and 688; 303, 617, and 696; 303, 617, and 702; 303, 617, and 709; 303, 617, and A712; 303, 617, and 714; 303, 617, and 790; 303, 617, and 841; 303, 617, and 862;

303, 688, and 696; 303, 688, and 702; 303, 688, and 709; 303, 688, and A712; 303, 688, and 714; 303, 688, and 790; 303, 688, and 841; 303, 688, and 862; 303, 696, and 702; 303, 696, and 709; 303, 696, and A712; 303, 696, and 714; 303, 696, and 790; 303, 696, and 841; 303, 696, and 862; 303, 702, and 709; 303, 702, and A712; 303, 702, and 714; 303, 702, and 790; 303, 702, and 841; 303, 702, and 862; 303, 709, and A712; 303, 709, and 714; 303, 709, and 790; 303, 709, and 841; 303, 709, and 862; 303, A712, and 714; 303, A712, and 790; 303, A712, and 841; 303, A712, and 862; 303, 714, and 790; 303, 714, and 841; 303, 714, and 862; 303, 790, and 841; 303, 790, and 862; 303, 841, and 862; 426, 433, and 435; 426, 433, and 530; 426, 433, and 572; 426, 433, and 596; 426, 433, and 617; 426, 433, and 688; 426, 433, and 696; 426, 433, and 702; 426, 433, and 709; 426, 433, and A712; 426, 433, and 714; 426, 433, and 790; 426, 433, and 841; 426, 433, and 862; 426, 435, and 530; 426, 435, and 572; 426, 435, and 596; 426, 435, and 617; 426, 435, and 688; 426, 435, and 696; 426, 435, and 702; 426, 435, and 709; 426, 435, and A712; 426, 435, and 714; 426, 435, and 790; 426, 435, and 841; 426, 435, and 862; 426, 530, and 572; 426, 530, and 596; 426, 530, and 617; 426, 530, and 688; 426, 530, and 696; 426, 530, and 702; 426, 530, and 709; 426, 530, and A712; 426, 530, and 714; 426, 530, and 790; 426, 530, and 841; 426, 530, and 862; 426, 572, and 596; 426, 572, and 617; 426, 572, and 688; 426, 572, and 696; 426, 572, and 702; 426, 572, and 709; 426, 572, and A712; 426, 572, and 714; 426, 572, and 790; 426, 572, and 841; 426, 572, and 862; 426, 596, and 617; 426, 596, and 688; 426, 596, and 696; 426, 596, and 702; 426, 596, and 709; 426, 596, and A712; 426, 596, and 714; 426, 596, and 790; 426, 596, and 841; 426, 596, and 862; 426, 617, and 688; 426, 617, and 696; 426, 617, and 702; 426, 617, and 709; 426, 617, and A712; 426, 617, and 714; 426, 617, and 790; 426, 617, and 841; 426, 617, and 862; 426, 688, and 696; 426, 688, and 702; 426, 688, and 709; 426, 688, and A712; 426, 688, and 714; 426, 688, and 790; 426, 688, and 841; 426, 688, and 862; 426, 696, and 702; 426, 696, and 709; 426, 696, and A712; 426, 696, and 714; 426, 696, and 790; 426, 696, and 841; 426, 696, and 862; 426, 702, and 709; 426, 702, and A712; 426, 702, and 714; 426, 702, and 790; 426, 702, and 841; 426, 702, and 862; 426, 709, and A712; 426, 709, and 714; 426, 709, and 790; 426, 709, and 841; 426, 709, and 862; 426, A712, and 714; 426, A712, and 790; 426, A712, and 841; 426, A712, and 862; 426, 714, and 790; 426, 714, and 841; 426, 714, and 862; 426, 790, and 841; 426, 790, and 862; 426, 841, and 862; 433, 435, and 530; 433, 435, and 572; 433, 435, and 596; 433, 435, and 617; 433, 435, and 688; 433, 435, and 696; 433, 435, and 702; 433, 435, and 709; 433, 435, and A712; 433, 435, and 714; 433, 435, and 790; 433, 435, and 841; 433, 435, and 862; 433, 530, and 572; 433, 530, and 596; 433, 530, and 617; 433, 530, and 688; 433, 530, and 696; 433, 530, and 702; 433, 530, and 709; 433, 530, and A712; 433, 530, and 714; 433, 530, and 790; 433, 530, and 841; 433, 530, and 862; 433, 572, and 596; 433, 572, and 617; 433, 572, and 688; 433, 572, and 696; 433, 572, and 702; 433, 572, and 709; 433, 572, and A712; 433, 572, and 714; 433, 572, and 790; 433, 572, and 841; 433, 572, and 862; 433, 596, and 617; 433, 596, and 688; 433, 596, and 696; 433, 596, and 702; 433, 596, and 709; 433, 596, and A712; 433, 596, and 714; 433, 596, and 790; 433, 596, and 841; 433, 596, and 862; 433, 617, and 688; 433, 617, and 696; 433, 617, and 702; 433, 617, and 709; 433, 617, and A712; 433, 617, and 714; 433, 617, and 790; 433, 617, and 841; 433, 617, and 862; 433, 688, and 696; 433, 688, and 702; 433, 688, and 709; 433, 688, and A712; 433, 688, and 714; 433, 688, and 790; 433, 688, and 841; 433, 688, and 862; 433, 696, and 702; 433, 696, and 709; 433, 696, and A712; 433, 696, and 714; 433, 696, and 790; 433, 696, and 841; 433, 696, and 862; 433, 702, and 709; 433, 702, and A712; 433, 702, and 714; 433, 702, and 790; 433, 702, and 841; 433, 702, and 862; 433, 709, and A712; 433, 709, and 714; 433, 709, and 790; 433, 709, and 841; 433, 709, and 862; 433, A712, and 714; 433, A712, and 790; 433, A712, and 841; 433, A712, and 862; 433, 714, and 790; 433, 714, and 841; 433, 714, and 862; 433, 790, and 841; 433, 790, and 862; 433, 841, and 862; 435, 530, and 572; 435, 530, and 596; 435, 530, and 617; 435, 530, and 688; 435, 530, and 696; 435, 530, and 702; 435, 530, and 709; 435, 530, and A712; 435, 530, and 714; 435, 530, and 790; 435, 530, and 841; 435, 530, and 862; 435, 572, and 596; 435, 572, and 617; 435, 572, and 688; 435, 572, and 696; 435, 572, and 702; 435, 572, and 709; 435, 572, and A712; 435, 572, and 714; 435, 572, and 790; 435, 572, and 841; 435, 572, and 862; 435, 596, and 617; 435, 596, and 688; 435, 596, and 696; 435, 596, and 702; 435, 596, and 709; 435, 596, and A712; 435, 596, and 714; 435, 596, and 790; 435, 596, and 841; 435, 596, and 862; 435, 617, and 688; 435, 617, and 696; 435, 617, and 702; 435, 617, and 709; 435, 617, and A712; 435, 617, and 714; 435, 617, and 790; 435, 617, and 841; 435, 617, and 862; 435, 688, and 696; 435, 688, and 702; 435, 688, and 709; 435, 688, and A712; 435, 688, and 714; 435, 688, and 790; 435, 688, and 841; 435, 688, and 862; 435, 696, and 702; 435, 696, and 709; 435, 696, and A712; 435, 696, and 714; 435, 696, and 790; 435, 696, and 841; 435, 696, and 862; 435, 702, and 709; 435, 702, and A712; 435, 702, and 714; 435, 702, and 790; 435, 702, and 841; 435, 702, and 862; 435, 709, and A712; 435, 709, and 714; 435, 709, and 790; 435, 709, and 841; 435, 709, and 862; 435, A712, and 714; 435, A712, and 790; 435, A712, and 841; 435, A712, and 862; 435, 714, and 790; 435, 714, and 841; 435, 714, and 862; 435, 790, and 841; 435, 790, and 862; 435, 841, and 862; 530, 572, and 596; 530, 572, and 617; 530, 572, and 688; 530, 572, and 696; 530, 572, and 702; 530, 572, and 709; 530, 572, and A712; 530, 572, and 714; 530, 572, and 790; 530, 572, and 841; 530, 572, and 862; 530, 596, and 617; 530, 596, and 688; 530, 596, and 696; 530, 596, and 702; 530, 596, and 709; 530, 596, and A712; 530, 596, and 714; 530, 596, and 790; 530, 596, and 841; 530, 596, and 862; 530, 617, and 688; 530, 617, and 696; 530, 617, and 702; 530, 617, and 709; 530, 617, and A712; 530, 617, and 714; 530, 617, and 790; 530, 617, and 841; 530, 617, and 862; 530, 688, and 696; 530, 688, and 702; 530, 688, and 709; 530, 688, and A712; 530, 688, and 714; 530, 688, and 790; 530, 688, and 841; 530, 688, and 862; 530, 696, and 702; 530, 696, and 709; 530, 696, and A712; 530, 696, and 714; 530, 696, and 790; 530, 696, and 841; 530, 696, and 862; 530, 702, and 709; 530, 702, and A712; 530, 702, and 714; 530, 702, and 790; 530, 702, and 841; 530, 702, and 862; 530, 709, and A712; 530, 709, and 714; 530, 709, and 790; 530, 709, and 841; 530, 709, and 862; 530, A712, and 714; 530, A712, and 790; 530, A712, and 841; 530, A712, and 862; 530, 714, and 790; 530, 714, and 841; 530, 714, and 862; 530, 790, and 841; 530, 790, and 862; 530, 841, and 862; 572, 596, and 617; 572, 596, and 688; 572, 596, and 696; 572, 596, and 702; 572, 596, and 709; 572, 596, and A712; 572, 596, and 714; 572, 596, and 790; 572, 596, and 841; 572, 596, and 862; 572, 617, and 688; 572, 617, and 696; 572, 617, and 702; 572, 617, and 709; 572, 617, and A712; 572, 617, and 714; 572, 617, and 790; 572, 617, and 841; 572, 617, and 862; 572, 688, and 696; 572, 688, and 702; 572, 688, and 709; 572, 688, and A712; 572, 688, and 714; 572, 688, and 790; 572, 688, and 841; 572, 688, and 862; 572, 696, and 702; 572, 696, and 709; 572, 696, and A712; 572, 696, and 714; 572, 696, and 790; 572, 696, and 841; 572, 696, and 862; 572, 702, and 709; 572, 702, and A712; 572, 702, and 714; 572, 702, and 790; 572, 702, and 841; 572, 702, and 862; 572, 709, and A712; 572, 709, and 714; 572, 709, and 790; 572, 709, and 841; 572, 709, and 862; 572, A712, and 714; 572, A712, and 790; 572, A712, and 841; 572, A712, and 862; 572, 714, and 790; 572, 714, and 841; 572, 714, and 862; 572, 790, and 841; 572, 790, and 862; 572, 841, and 862; 596, 617, and 688; 596, 617, and 696; 596, 617, and 702; 596, 617, and 709; 596, 617, and A712; 596, 617, and 714; 596, 617, and 790; 596, 617, and 841; 596, 617, and 862; 596, 688, and 696; 596, 688, and 702; 596, 688, and 709; 596, 688, and A712; 596, 688, and 714; 596, 688, and 790; 596, 688, and 841; 596, 688, and 862; 596, 696, and 702; 596, 696, and 709; 596, 696, and A712; 596, 696, and 714; 596, 696, and 790; 596, 696, and 841; 596, 696, and 862; 596, 702, and 709; 596, 702, and A712; 596, 702, and 714; 596, 702, and 790; 596, 702, and 841; 596, 702, and 862; 596, 709, and A712; 596, 709, and 714; 596, 709, and 790; 596, 709, and 841; 596, 709, and 862; 596, A712, and 714; 596, A712, and 790; 596, A712, and 841; 596, A712, and 862; 596, 714, and 790; 596, 714, and 841; 596, 714, and 862; 596, 790, and 841; 596, 790, and 862; 596, 841, and 862; 617, 688, and 696; 617, 688, and 702; 617, 688, and 709; 617, 688, and A712; 617, 688, and 714; 617, 688, and 790; 617, 688, and 841; 617, 688, and 862; 617, 696, and 702; 617, 696, and 709; 617, 696, and A712; 617, 696, and 714; 617, 696, and 790; 617, 696, and 841; 617, 696, and 862; 617, 702, and 709; 617, 702, and A712; 617, 702, and 714; 617, 702, and 790; 617, 702, and 841; 617, 702, and 862; 617, 709, and A712; 617, 709, and 714; 617, 709, and 790; 617, 709, and 841; 617, 709, and 862; 617, A712, and 714; 617, A712, and 790; 617, A712, and 841; 617, A712, and 862; 617, 714, and 790; 617, 714, and 841; 617, 714, and 862; 617, 790, and 841; 617, 790, and 862; 617, 841, and 862; 688, 696, and 702; 688, 696, and 709; 688, 696, and A712; 688, 696, and 714; 688, 696, and 790; 688, 696, and 841; 688, 696, and 862; 688, 702, and 709; 688, 702, and A712; 688, 702, and 714; 688, 702, and 790; 688, 702, and 841; 688, 702, and 862; 688, 709, and A712; 688, 709, and 714; 688, 709, and 790; 688, 709, and 841; 688, 709, and 862; 688, A712, and 714; 688, A712, and 790; 688, A712, and 841; 688, A712, and 862; 688, 714, and 790; 688, 714, and 841; 688, 714, and 862; 688, 790, and 841; 688, 790, and 862; 688, 841, and 862; 696, 702, and 709; 696, 702, and A712; 696, 702, and 714; 696, 702, and 790; 696, 702, and 841; 696, 702, and 862; 696, 709, and A712; 696, 709, and 714; 696, 709, and 790; 696, 709, and 841; 696, 709, and 862; 696, A712, and 714; 696, A712, and 790; 696, A712, and 841; 696, A712, and 862; 696, 714, and 790; 696, 714, and 841; 696, 714, and 862; 696, 790, and 841; 696, 790, and 862; 696, 841, and 862; 702, 709, and A712; 702, 709, and 714; 702, 709, and 790; 702, 709, and 841; 702, 709, and 862; 702, A712, and 714; 702, A712, and 790; 702, A712, and 841; 702, A712, and 862; 702, 714, and 790; 702, 714, and 841; 702, 714, and 862; 702, 790, and 841; 702, 790, and 862; 702, 841, and 862; 709, A712, and 714; 709, A712, and 790; 709, A712, and 841; 709, A712, and 862; 709, 714, and 790; 709, 714, and 841; 709, 714, and 862; 709, 790, and 841; 709, 790, and 862; 709, 841, and 862; A712, 714, and 790; A712, 714, and 841; A712, 714, and 862; A712, 790, and 841; A712, 790, and 862; A712, 841, and 862; 714, 790, and 841; 714, 790, and 862; 714, 841, and 862; or 790, 841, and 862.

In some embodiments, the nucleotide sequence of a promoter element as provided herein can include two mutations as compared to the nucleotide sequence of a reference promoter element. For example, in some embodiments, two mutations at positions corresponding to the following positions relative to SEQ ID NO: 28 can be present in a promoter sequence: 688 and 696; 688 and 702; 688 and A712; 688 and 714; 696 and 702; 696 and A712; 696 and 714; 702 and A712; 702 and 714; or A712 and 714.

In some embodiments, the nucleotide sequence of a promoter element as provided herein can include three mutations as compared to the nucleotide sequence of a reference promoter element. For example, in some embodiments, three mutations at positions corresponding to the following positions relative to SEQ ID NO: 28 can be present in a promoter sequence: 688, 696, and 702; 688, 696, and A712; 688, 696, and 714; 688, 702, and A712; 688, 702, and 714; 688, A712, and 714; 696, 702, and A712; 696, 702, and 714; 696, A712, and 714; or 702, A712, and 714.

In some embodiments, the nucleotide sequence of a promoter element as provided herein can include four mutations as compared to the nucleotide sequence of a reference promoter element. For example, in some embodiments, four mutations at positions corresponding to the following positions relative to SEQ ID NO: 28 can be present in a promoter sequence: 688, 696, 702, and A712; 688, 696, 702, and 714; 688, 696, A712, and 714; 688, 702, A712, and 714; or 696, 702, A712, and 714.

In some embodiments, the nucleotide sequence of a promoter element as provided herein can include five mutations as compared to the nucleotide sequence of a reference promoter element. For example, in some embodiments, five mutations at positions corresponding to the following positions relative to SEQ ID NO: 28 can be present in a promoter sequence: 688, 696, 702, A712, and 714.

Nucleic acid molecules used in the methods described herein are typically DNA, but RNA molecules can be used under the appropriate circumstances. As used herein, "exogenous" refers to any nucleic acid sequence that is introduced into a cell from, for example, the same or a different organism or a nucleic acid generated synthetically (e.g., a codon-optimized nucleic acid sequence). For example, an exogenous nucleic acid can be a nucleic acid from one microorganism (e.g., one genus or species of methylotrophic yeast) that is introduced into a different genus or species of methylotrophic yeast; however, an exogenous nucleic acid also can be a nucleic acid from a methylotrophic yeast that is introduced recombinantly into a methylotrophic yeast as an additional copy despite the presence of a corresponding native nucleic acid sequence, or a nucleic acid from a methylotrophic yeast that is introduced recombinantly into a methylotrophic yeast containing one or more mutations, insertions, or deletions compared to the sequence native to the methylotrophic yeast. For example, *P. pastoris* contains an endogenous nucleic acid encoding an ALAS; an additional copy of the *P. pastoris* ALAS nucleic acid (e.g., introduced recombinantly into *P. pastoris*) is considered to be exogenous. Similarly, an "exogenous" protein is a protein encoded by an exogenous nucleic acid.

In some instances, an exogenous nucleic acid can be a heterologous nucleic acid. As used herein, a "heterologous" nucleic acid refers to any nucleic acid sequence that is not native to an organism (e.g., a heterologous nucleic acid can be a nucleic acid from one microorganism (e.g., one genus or species of methylotrophic yeast, whether or not it has been codon-optimized) that is introduced into a different genus or species of methylotrophic yeast)). Similarly, a "heterologous" protein is a protein encoded by a heterologous nucleic acid.

A nucleic acid molecule is considered to be exogenous to a host organism when any portion thereof (e.g., a promoter sequence or a sequence of an encoded protein) is exogenous to the host organism. A nucleic acid molecule is considered to be heterologous to a host organism when any portion thereof (e.g., a promoter sequence or a sequence of an encoded protein) is heterologous to the host organism.

Nucleic acid constructs are provided herein that allow for genetically engineering a cell (e.g., a yeast cell (e.g., a methylotrophic yeast cell)). In some embodiments, nucleic acid constructs are provided herein that allow for genetically engineering a cell (e.g., a yeast cell (e.g., a methylotrophic yeast cell)) to produce an RNA. Recombinantly produced RNAs can be used to modify a function of the cell, for example by RNA interference or as a guide for DNA editing. In some embodiments, nucleic acid constructs are provided herein that allow for genetically engineering a cell (e.g., a yeast cell (e.g., a methylotrophic yeast cell)) to produce a product (e.g., a protein). In some embodiments, nucleic acid constructs are provided herein that allow for genetically engineering a cell (e.g., a yeast cell (e.g., a methylotrophic yeast cell)) to produce an exogenous product (e.g., a protein). In some embodiments, nucleic acid constructs are provided herein that allow for genetically engineering a cell (e.g., a yeast cell (e.g., a methylotrophic yeast cell)) to produce a heterologous product (e.g., a protein). In some embodiments, a nucleic acid constructs are provided herein that allow for genetically engineering a cell (e.g., a yeast cell (e.g., a methylotrophic yeast cell)) to produce a product (e.g., a protein) in the absence of methanol. In addition, nucleic acid constructs are provided herein that allow for genetically engineering a cell (e.g., a yeast cell (e.g., a methylotrophic yeast cell)) to increase the expression of a heme-binding protein.

Also provided herein is a cell including any of the promoter elements described herein. A cell can be any appropriate cell. For example, a cell can be a bacterial cell (e.g., an *E. coli* cell, a *B. subtilis* cell, or a *Lactococcus lactis* cell), a fungal cell, an algal cell, a plant cell, an insect cell, or a mammalian cell. In some embodiments, a cell can be a yeast cell. Non-limiting examples of yeast cells include *Pichia* (e.g., *Pichia methanolica, Pichia pastoris*), *Candida* (e.g., *Candida boidinii*) cells, *Hansenula* (e.g., *Hansenula polymorpha*) cells, *Torulopsis* cells, and *Sacharomyces* (e.g., *Sacaromyces cerevisae*) cells. In some embodiments, a cell can be a methylotrophic yeast cell. Non-limiting examples of methylotrophic yeast cells include *Pichia* cells, *Candida* cells, *Hansenula* cells, and *Torulopsis* cells. In some embodiments, a cell can be a *Pichia* cell or a *Sacharomyces* cell.

In some embodiments, this document provides a cell containing a nucleic acid construct (e.g., a first nucleic acid construct, a second nucleic acid construct, and so forth) including a nucleotide sequence operably linked to a promoter element as described herein. A nucleic acid construct including a nucleotide sequence can include any appropriate nucleotide sequence.

As used herein, "operably linked" means that a promoter or other expression element(s) are positioned relative to a coding sequence in such a way as to direct or regulate expression of the coding sequence (e.g., in-frame).

It will be appreciated that a nucleic acid construct including a nucleotide sequence operably linked to any of the promoter elements as described herein can include nucleotide sequence of interest. In some embodiments, transcription and/or translation of a nucleotide sequence can result in the production of a product (e.g., protein, DNA, RNA, or a small molecule) of interest. For example, in some embodiments, a nucleic acid construct including a nucleotide sequence can be a nucleic acid construct encoding a protein. For example, in some embodiments, a nucleic acid construct including a nucleotide sequence can be a nucleic acid construct encoding an RNA (e.g., an mRNA, a tRNA, a ribozyme, a siRNA, miRNA, or a shRNA). For example, in some embodiments, a nucleic acid construct including a nucleotide sequence can be a nucleic acid construct encoding a DNA. For example, in some embodiments, a nucleic acid construct including a nucleotide sequence can be a nucleic acid construct whose transcription results in or contributes to the production of a small molecule (e.g., heme, ethanol, or a pharmaceutically active agent).

In some embodiments, a nucleic acid construct (e.g., a first nucleic acid construct, a second nucleic acid construct, and so forth) including a nucleotide sequence can be a nucleic acid construct encoding a protein (e.g., a first protein, a second protein, and so forth).

Recombinantly expressed proteins can be widely used in many applications, such as for food, research, and medicine. In some embodiments, a protein encoded by a nucleic acid construct including a nucleotide sequence operably linked to any of the promoter elements as described herein can be a dehydrin, a phytase, a protease, a catalase, a lipase, a peroxidase, an amylase, a transglutaminase, an oxidoreductase, a transferase, a hydrolase, a lyase, an isomerase, or a ligase. In some embodiments, a protein encoded by a nucleic acid operably linked to any of the promoter elements as described herein can be an antibody or fragment thereof (e.g., adalimumab, rituximab, trastuzumab, bevacizumab, infliximab, or ranibizumab), an enzyme (e.g., a therapeutic enzyme such as alpha-galactosidase A, alpha-L-iduronidase, N-acetylgalactosamine-4-sulfatase, dornase alfa, glucocerebrosidase, tissue plasminogen activator, rasburicase, an industrial enzyme (e.g., a catalase, a cellulase, a laccase, a glutaminase, or a glycosidase), or a biocatalyst (e.g., a transaminase, a cytochrome P450, a kinase, a phosphorylase, or an isomerase)), a regulatory protein (e.g., a transcription factor (e.g. Mxr1, Adr1)), a peptide hormone (e.g., insulin, insulin-like growth factor 1, granulocyte colony-stimulating factor, follicle-stimulating hormone, or a growth hormone such as human growth hormone), a blood clotting protein (e.g., Factor VII), a cytokine (e.g., an interferon or erythropoietin), or a cytokine inhibitor (e.g., etanercept).

In some embodiments, a protein can be a heme-binding protein (e.g., an exogenous or heterologous heme binding protein). In some embodiments, a heme-binding protein can be selected from the group consisting of a globin (PF00042 in the Pfam database), a cytochrome (e.g., a cytochrome P450, a cytochrome a, a cytochrome b, a cytochrome c), a cytochrome c oxidase, a ligninase, a catalase, and a peroxidase. In some embodiments, a globin can be selected from the group consisting of an androglobin, a chlorocruorin, a cytoglobin, an erythrocruorin, a flavohemoglobin, a globin E, a globin X, a globin Y, a hemoglobin (e.g., a beta hemoglobin, an alpha hemoglobin), a histoglobin, a leghemoglobin, a myoglobin, a neuroglobin, a non-symbiotic hemoglobin, a protoglobin, and a truncated hemoglobin (e.g., a HbN, a HbO, a Glb3, a cyanoglobin). In some embodiments, the heme-binding protein can be a non-symbiotic hemoglobin. In some embodiments, the heme-binding protein can be a leghemoglobin. In some embodiments, the heme-binding protein can be soybean leghemoglobin (LegH). A reference amino acid sequence for LegH is provided in FIG. 1 as SEQ ID NO: 4. LegH is a protein that binds to heme, which results in a characteristic absorption at 415 nm and a distinct red color. The LegH protein (also known as LGB2) is naturally found in root nodules of soybean (see, for example, UniprotKB Accession No. P02236). See, also, WO 2014/110539 and WO 2014/110532, each of which is incorporated by reference herein in its entirety. In some embodiments, a heme-binding protein can have an amino acid sequence that is at least 70% (e.g., at least 75%, 80%, 85%, 90%, 91%, 92%, 93%, 94%, 95%, 96%, 97%, 98%, or 99%) identical to the amino acid sequence set forth in any of SEQ ID NOs: 1-27 (FIG. 1). In some embodiments, a heme-binding protein is the amino acid sequence set forth in any of SEQ ID NOs: 1-27 (FIG. 1).

While the materials and methods are exemplified herein using an alcohol oxidase promoter element from a *Pichia* species (*P. pastoris*), other organisms can be used. For example, an alcohol oxidase promoter element from a different methylotrophic yeast can be used, such as other species of the *Pichia* genus or species from any of the *Candida*, *Hansenula*, *Pichia*, and *Torulopsis* genera. Non-limiting examples of methylotrophic yeast species include *Pichia methanolica*, *Pichia pastoris*, *Candida boidinii*, and *Hansenula polymorpha* (also called *Pichia angusta*). In some embodiments, a promoter element can be an alcohol oxidase promoter element from any of the *Candida*, *Hansenula*, *Pichia*, and *Torulopsis* genera. In some embodiments, a promoter element can have at least 70% (e.g., at least 75%, 80%, 85%, 90%, 95%, 97%, 98%, or 99%) sequence identity to an alcohol oxidase promoter element from any of the *Candida*, *Hansenula*, *Pichia*, and *Torulopsis* genera. In some embodiments, a promoter element can be an alcohol oxidase promoter element from any of the *Candida*, *Hansenula*, *Pichia*, and *Torulopsis* genera. In some embodiments, a promoter element can be an alcohol oxidase promoter element from *Pichia methanolica*, *Pichia pastoris*, *Candida boidinii*, or *Hansenula polymorpha*. In some embodiments, a promoter element can have at least 70% (e.g., at least 75%, 80%, 85%, 90%, 95%, 97%, 98%, or 99%) sequence identity to an alcohol oxidase promoter element from *Pichia methanolica*, *Pichia pastoris*, *Candida boidinii*, or *Hansenula polymorpha*. In some embodiments, a promoter element can be an alcohol oxidase promoter element from *Pichia methanolica*, *Pichia pastoris*, *Candida boidinii*, or *Hansenula polymorpha*. Non-limiting examples of other alcohol oxidase promoters include the AOX2 promoter from *Pichia pastoris*, *pastoris* (see, e.g., Ohi, Hideyuki, et al. Molecular and General Genetics MGG 243.5 (1994): 489-499, incorporated herein by reference in its entirety), the alcohol oxidase (AOD1) promoter from *Candida boidinii* (see, for example, GenBank Accession No. YSAAOD1A), the alcohol oxidase (MOX) promoter from *Hansenula polymorpha* (see, for example, GenBank Accession No. X02425), or the MOD1 or MOD2 promoter from *Pichia methanolica* (see, for example, Raymond et al., 1998, Yeast, 14:11-23; and Nakagawa et al., 1999, Yeast, 15:1223-30). In some embodiments, an alcohol oxidase promoter element can be selected from the group consisting of a promoter element from AOX1, AOX2, AOD1, MOX, MOD1, and MOD2. In some embodiments, an alcohol oxidase promoter element can be a promoter element from AOX1. In some embodiments, an alcohol oxidase promoter element can be a promoter element from AOX2. In some embodiments, an alcohol oxidase promoter element can be a promoter element from AOD1. In some embodiments, an alcohol oxidase promoter element can be a promoter element from MOX. In some embodiments, an alcohol oxidase promoter element can be a promoter element from MOD1. In some embodiments, an alcohol oxidase promoter element can be a promoter element from MOD2.

In some embodiments, any of the cells (e.g., yeast cells (e.g., methylotrophic yeast cells)) described herein can include a second nucleic acid construct including a nucleotide sequence, transcription and/or translation of which can result in the production of a product a second product (e.g., a protein, an RNA, a DNA, or a small molecule) operably linked to a promoter element. In some embodiments, the promoter element to which the nucleotide sequence of the second nucleic acid construct is operably linked is the same as the promoter element to which the nucleotide sequence of the first nucleic acid construct is operably linked. In some embodiments, the promoter element to which the nucleotide sequence of the second nucleic acid construct is operably linked is a second promoter element. In some embodiments, a second promoter element can be any of the promoter elements described herein. In some embodiments, the second promoter element can have the same sequence as the first promoter element. In some embodiments, the second promoter element can include one or more mutations corresponding to nucleotide positions 668-734 (e.g., nucleotide positions 673-729, nucleotide positions 678-724, nucleotide positions 683-719, or nucleotide positions 688-714) relative to SEQ ID NO: 28. In some embodiments, the second promoter element can include one or more (e.g., 2, 3, 4, 5, 6, 7, 8, 9, 10, 11, 12, 13, 14, 15, 16, 17, 18, or 19) mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. In some embodiments, the second promoter element can include one or more (e.g., 2, 3, 4, 5, 6, 7, 8, 9, 10, 11, 12, 13, 14, 15, 16, 17, 18, or 19) mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28, as long as the indicated nucleobase is not the same as the corresponding naturally-occurring nucleobase. In some embodiments, one or more (e.g., 2, 3, 4, 5, 6, 7, 8, 9, 10, 11, 12, 13, 14, 15, 16, 17, 18, or 19) mutations at positions corresponding to the following positions relative to SEQ ID NO: 28 can be present in a second promoter element: T146; C154; T303; T426; A433; A435; T530; C572; T596; T617; T688; A696; T702; A709; A712; T714; A790; A841; or T862. In some embodiments, one or more (e.g., 2, 3, 4, 5, 6, 7, 8, 9, 10, 11, 12, 13, 14, 15, 16, 17, 18, or 19) mutations at positions corresponding to the following positions relative to SEQ ID NO: 28 can be present in a second promoter element: 146; 154; 303; 426; 433; 435; 530; 572; 596; 617; 688; 696; 702; 709; 712; 714; 790; 841; or 862. In some embodiments, the second promoter element can include one or more (e.g., 2, 3, 4, or 5) mutations selected from the group consisting of mutations corresponding to T688C, A696T, T702C, A712G, or T714G relative to SEQ ID NO: 28. In some embodiments, the second promoter element can include one or more (e.g., 2, 3, 4, or 5) mutations selected from the group consisting of mutations corresponding to 688C, 696T, 702C, 712G, or 714G relative to SEQ ID NO: 28, as long as the indicated nucleobase is not the same as the corresponding naturally-occurring nucleobase. In some embodiments, one or more (e.g., 2, 3, 4, or 5) mutations corresponding to one of the following positions relative to SEQ ID NO: 28 can be present in a second promoter element: T688; A696; T702; A712; or T714. In some embodiments, one or more (e.g., 2, 3, 4, or 5) mutations corresponding to one of the following positions relative to SEQ ID NO: 28 can be present in a second promoter element: 688; 696; 702; 712; or 714. In some embodiments, the second promoter element can be an inducible promoter element (e.g., a methanol-inducible promoter element) or a constitutive promoter element.

Any of a number of inducible promoters can generally be used when genetically engineering cells (e.g., yeast (e.g., methylotrophic yeast). For example, a methanol-inducible promoter, or a promoter element therefrom, can be used. Suitable methanol inducible promoters include pAOX1, as described herein, as well as other methanol-inducible promoters, or promoter elements therefrom. These include, without limitation, the pAOX2 promoter from *Pichia pastoris*, the alcohol oxidase (AOD1) promoter from *Candida boidinii* (see, for example, GenBank Accession No. YSAAOD1A), the alcohol oxidase (MOX) promoter from *Hansenula polymorpha* (see, for example, GenBank Accession No. X02425), the MOD1 or MOD2 promoter from *Pichia methanolica* (see, for example, Raymond et al., 1998, *Yeast*, 14:11-23; and Nakagawa et al., 1999, *Yeast*, 15:1223-30), the DHAS promoter from *P. pastoris* (see, for example, GenBank Accession No. FJ752551) or a promoter element therefrom, the formaldehyde dehydrogenase (FLD1) promoter from *P. pastoris* (see, for example, GenBank Accession No. AF066054), or the PEX8 promoter from *P. pastoris* (see, for example, Kranthi et al., 2010, Yeast, 27:705-11). All of these promoters are known to be induced by methanol. Suitable constitutive promoters and constitutive promoter elements include, without limitation, the *P. pastoris* promoter (or a portion thereof) from the transcriptional elongation factor EF-1α gene (TEF1), which is strongly transcribed in a constitutive manner. Other suitable constitutive promoters (or promoter elements therefrom) also can be used, including, without limitation, the glyceraldehyde-3-phosphate dehydrogenase (GAPDH) promoter from *P. pastoris* (see, for example, GenBank Accession No. U62648.1), the promoter from the potential glycosyl phosphatidyl inositol (GPI)-anchored protein, GCW14p (PAS_chr1-4_0586) from *P. pastoris* (see, for example, GenBank Accession No. XM_002490678), and the promoter from the 3-phosphoglycerate kinase gene (PGK1) from *P. pastoris* (see, for example, GenBank Accession No. AY288296). Further, it is noted that a combination of inducible (e.g., methanol-inducible) and constitutive promoters (or promoter elements therefrom) can be combined to further increase the expression of any of the nucleic acids operably linked thereto.

In some embodiments, a second protein can be any of the proteins as described above. In some embodiments, the second protein can be a transcription factor (e.g., Mxr1). In some embodiments, any of the promoter elements herein (e.g., a first promoter element or a second promoter element) can contain one or more recognition sequences for a transcription factor. Therefore, in some embodiments, a feedback loop may be constructed such that the transcription factor drives the expression of a protein of interest and also expression of additional copies of the transcription factor. In some embodiments, the transcription factor can be Mxr1. In some embodiments, the second protein can be a protein involved in heme biosynthesis (e.g., a protein selected from the group consisting of aminolevulinic acid synthase (ALAS), δ-aminolevulinic acid dehydratase (ALAD), porphobilinogen deaminase (PBGD), uroporphyrinogen III synthase (UPG3S), uroporphyrinogen III decarboxylase (UPG3D), coprotoporphyrinogen oxidase (COPROX), protoporphyrinogen IX oxidase (PROTOX), and/or ferrochelatase (FC)).

Nucleic acids encoding one or more of the eight different enzymes involved in heme biosynthesis (as determined and annotated from the sequence of the *Pichia pastoris* genome) can be expressed as described herein. For example, a heterologous nucleic acid molecule encoding ALA synthase, ALA dehydratase, porphobilinogen deaminase, UPG III synthase, UPG III decarboxylase, CPG oxidase, PPG oxidase, and ferrochelatase can be expressed in the strains (e.g., yeast strains (e.g., methylotrophic yeast strains)) described herein. For genetically engineering cells (e.g., yeast (e.g., methylotrophic yeast)) to contain more than one heterologous nucleic acids (e.g., transgenes), a combination of methanol-inducible and constitutive promoters, or elements therefrom, can be combined to further increase the expression of such nucleic acids.

It will be understood that any of the cells (e.g., yeast cells (e.g., methylotrophic yeast cells) described herein can include additional nucleic acid constructs as a third, fourth, fifth, and so on, nucleic acid construct, and such constructs can, in some embodiments, be as described above for a second nucleic acid construct.

Previous studies in *Saccharomyces cerevisiae* identified ALAD and porphobilinogen deaminase as rate limiting enzymes in heme biosynthesis (see, for example, Hoffman et al., 2003, *Biochem. Biophys. Res. Commun.*, 310(4):1247-53). However, heterologous expression of individual heme enzymes in *P. pastoris* from the glyceraldehyde-3-phosphate dehydrogenase (GAP) promoter failed to overcome limitations associated with the expression of a recombinant protein containing a heme (see, Krainer et al., 2015, *Microb. Cell Fact.*, 13; 14:4). Expression of a recombinant heme containing protein in *P. pastoris* can be achieved by co-expressing the entire heme biosynthetic pathway from methanol-inducible promoters, although it would be appreciated that one or more of the genes involved in the heme biosynthetic pathway could be expressed from one or more constitutive promoters (see, e.g., U.S. Pat. No. 9,938,327, which is incorporated by reference in its entirety).

Also provided herein are methods of producing a product (e.g., a protein) using any of the nucleic acid constructs and/or cells described herein. In some embodiments, the methods provided herein can include expressing a nucleic acid construct including a nucleotide sequence (e.g., encoding a first protein) operably linked to a first promoter element. In some embodiments, a first promoter element can be any promoter element described herein. In some embodiments, the first promoter element includes one or more mutations corresponding to nucleotide positions 668-734 (e.g., nucleotide positions 673-729, nucleotide positions 678-724, nucleotide positions 683-719, or nucleotide positions 688-714) relative to SEQ ID NO: 28. In some embodiments, the methods provided herein can include expressing a nucleic acid construct including a nucleotide sequence (e.g., encoding a first protein) operably linked to a first promoter element, where the first promoter element includes one or more (e.g., 2, 3, 4, 5, 6, 7, 8, 9, 10, 11, 12, 13, 14, 15, 16, 17, 18, or 19) mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. In some embodiments, the methods provided herein can include expressing a nucleic acid construct including a nucleotide sequence (e.g., encoding a first protein) operably linked to a first promoter element, where the first promoter element includes one or more (e.g., 2, 3, 4, 5, 6, 7, 8, 9, 10, 11, 12, 13, 14, 15, 16, 17, 18, or 19) mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28, as long as the indicated nucleobase is not the same as the corresponding naturally-occurring nucleobase. In some embodiments, the methods provided herein can include expressing a nucleic acid construct including a nucleotide sequence (e.g., encoding a first protein) operably linked to a first promoter element, wherein the promoter element includes one or more (e.g., 2, 3, 4, 5, 6, 7, 8, 9, 10, 11, 12, 13, 14, 15, 16, 17, 18, or 19) mutations at positions corresponding to the following positions relative to SEQ ID NO: 28: T146; C154; T303; T426; A433; A435; T530; C572; T596; T617; T688; A696; T702; A709; A712; T714; A790; A841; or T862. In some embodiments, the methods provided herein can include expressing a nucleic acid construct including a nucleotide sequence (e.g., encoding a first protein) operably linked to a first promoter element, wherein the promoter element includes one or more (e.g., 2, 3, 4, 5, 6, 7, 8, 9, 10, 11, 12, 13, 14, 15, 16, 17, 18, or 19) mutations at positions corresponding to the following positions relative to SEQ ID NO: 28: 146; 154; 303; 426; 433; 435; 530; 572; 596; 617; 688; 696; 702; 709; 712; 714; 790; 841; or 862. In some embodiments, the methods provided herein can include expressing a nucleic acid construct including a nucleotide sequence (e.g., encoding a first protein) operably linked to a first promoter element, where the first promoter element includes one or more (e.g., 2, 3, 4, or 5) mutations selected from the group consisting of mutations corresponding to T688C, A696T, T702C, A712G, and T714G relative to SEQ ID NO: 28. In some embodiments, the methods provided herein can include expressing a nucleic acid construct including a nucleotide sequence (e.g., encoding a first protein) operably linked to a first promoter element, where the first promoter element includes one or more (e.g., 2, 3, 4, or 5) mutations selected from the group consisting of mutations corresponding to 688C, 696T, 702C, 712G, and 714G relative to SEQ ID NO: 28, as long as the indicated nucleobase is not the same as the corresponding naturally-occurring nucleobase. In some embodiments, the methods provided herein can include expressing a nucleic acid construct including a nucleotide sequence (e.g., encoding a first protein) operably linked to a first promoter element, wherein the promoter element includes one or more one or more (e.g., 2, 3, 4, or 5) mutations at positions corresponding to the following positions relative to SEQ ID NO: 28: T688; A696; T702; A712; or T714. In some embodiments, the methods provided herein can include expressing a nucleic acid construct including a nucleotide sequence (e.g., encoding a first protein) operably linked to a first promoter element, wherein the promoter element includes one or more one or more (e.g., 2, 3, 4, or 5) mutations at positions corresponding to the following positions relative to SEQ ID NO: 28: 688; 696; 702; 712; or 714. In some embodiments of any of the methods described herein, the method can be performed in the absence of added methanol. In some embodiments, the primary carbon source for methylotrophic yeast cells can be dextrose, sucrose, xylose, lactose, maltose, isomaltose, arabinose, sugar alcohols, ethanol, acetate, or glycerol. In some embodiments, the primary carbon source can be selected from the group consisting of glucose, sucrose, sorbitol, methanol, and glycerol. In some embodiments, the primary carbon source can be selected from the group consisting of glucose, sucrose, sorbitol, and glycerol. In some embodiments the primary carbon source can be an oligosaccharide or a polysaccharide (e.g., a starch, a pectin, cellulose, or hemicellulose). In some embodiments, the primary carbon source for a methylotrophic yeast cell can be a mixture of sugars (e.g., derived from cellulosic biomass or starch).

In some embodiments, the methods provided herein allow for an increase in the titer of a product (e.g., a protein). In some embodiments, the titer of a product (e.g., a protein) can be increased by at least 5% (e.g., at least 6%, 7%, 8%, 9%, 10%, 15%, 20%, 30%, 40%, 50%, 60%, 70%, 80%, 90%, 100%, 150%, 200%, 250%, 300%, 350%, 400%, 500%, 600%, 700%, 800%, 900%, 1000%, or more) compared to a corresponding method lacking a nucleic acid construct as described herein. In some embodiments, the titer of a product (e.g., a protein) can be increased by at least 5% (e.g., at least 6%, 7%, 8%, 9%, 10%, 15%, 20%, 30%, 40%, 50%, 60%, 70%, 80%, 90%, 100%, 150%, 200%, 250%, 300%, 350%, 400%, 500%, 600%, 700%, 800%, 900%, 1000% or more) compared to a corresponding method that includes expressing a nucleic acid encoding a first product (e.g., a protein) operably linked to a first promoter element, where the first promoter element lacks any mutation in a nucleotide position corresponding to nucleotide positions 668-734 (e.g., nucleotide positions 673-729, nucleotide positions 678-724, nucleotide positions 683-719, or nucleotide positions 688-714) relative to SEQ ID NO: 28. In some embodiments, the titer of a product (e.g., a protein) can be increased by at least 5% (e.g., at least 6%, 7%, 8%, 9%, 10%, 15%, 20%, 30%, 40%, 50%, 60%, 70%, 80%, 90%, 100%, 150%, 200%, 250%, 300%, 350%, 400%, 500%, 600%, 700%, 800%, 900%, 1000% or more) compared to a corresponding method that includes expressing a nucleic acid construct including a nucleotide sequence (e.g., encoding a first protein) operably linked to a first promoter element, where the first promoter element lacks any mutation selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. In some embodiments, the titer of a product (e.g., a protein) can be increased by at least 5% (e.g., at least 6%, 7%, 8%, 9%, 10%, 15%, 20%, 30%, 40%, 50%, 60%, 70%, 80%, 90%, 100%, 150%, 200%, 250%, 300%, 350%, 400%, 500%, 600%, 700%, 800%, 900%, 1000% or more) compared to a corresponding method that includes expressing a nucleic acid construct including a nucleotide sequence (e.g., encoding a first protein) operably linked to a first promoter element, where the first promoter element lacks any mutation selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28, as long as the indicated nucleobase is not the same as the corresponding naturally-occurring nucleobase. In some embodiments, the titer of a product (e.g., a protein) can be increased by at least 5% (e.g., at least 6%, 7%, 8%, 9%, 10%, 15%, 20%, 30%, 40%, 50%, 60%, 70%, 80%, 90%, 100%, 150%, 200%, 250%, 300%, 350%, 400%, 500%, 600%, 700%, 800%, 900%, 1000% or more) compared to a corresponding method that includes expressing a nucleic acid construct including a nucleotide sequence (e.g., encoding a first protein) operably linked to a first promoter element, where the first promoter element lacks any mutation lacks any mutation in a nucleotide position corresponding to nucleotide positions T146, C154, T303, T426, A433, A435, T530, C572, T596, T617, T688, A696, T702, A709, A712, T714, A790, A841, and T862 relative to SEQ ID NO: 28. In some embodiments, the titer of a product (e.g., a protein) can be increased by at least 5% (e.g., at least 6%, 7%, 8%, 9%, 10%, 15%, 20%, 30%, 40%, 50%, 60%, 70%, 80%, 90%, 100%, 150%, 200%, 250%, 300%, 350%, 400%, 500%, 600%, 700%, 800%, 900%, 1000% or more) compared to a corresponding method that includes expressing a nucleic acid construct including a nucleotide sequence (e.g., encoding a first protein) operably linked to a first promoter element, where the first promoter element lacks any mutation lacks any mutation in a nucleotide position corresponding to nucleotide positions 146, 154, 303, 426, 433, 435, 530, 572, 596, 617, 688, 696, 702, 709, 712, 714, 790, 841, and 862 relative to SEQ ID NO: 28.

In some embodiments, the titer of a product (e.g., a protein) can be increased by at least 5% (e.g., at least 6%, 7%, 8%, 9%, 10%, 15%, 20%, 30%, 40%, 50%, 60%, 70%, 80%, 90%, 100%, 150%, 200%, 250%, 300%, 350%, 400%, 500%, 600%, 700%, 800%, 900%, 1000% or more) compared to a corresponding method that includes expressing a nucleic acid construct including a nucleotide sequence (e.g., encoding a first protein) operably linked to a first promoter element, where the first promoter element lacks any mutation selected from the group consisting of mutations corresponding to T688C, A696T, T702C, A712G, and T714G relative to SEQ ID NO: 28. In some embodiments, the titer of a product (e.g., a protein) can be increased by at least 5% (e.g., at least 6%, 7%, 8%, 9%, 10%, 15%, 20%, 30%, 40%, 50%, 60%, 70%, 80%, 90%, 100%, 150%, 200%, 250%, 300%, 350%, 400%, 500%, 600%, 700%, 800%, 900%, 1000% or more) compared to a corresponding method that includes expressing a nucleic acid construct including a nucleotide sequence (e.g., encoding a first protein) operably linked to a first promoter element, where the first promoter element lacks any mutation selected from the group consisting of mutations corresponding to 688C, 696T, 702C, 712G, and 714G relative to SEQ ID NO: 28. In some embodiments, the titer of a product (e.g., a protein) can be increased by at least 5% (e.g., at least 6%, 7%, 8%, 9%, 10%, 15%, 20%, 30%, 40%, 50%, 60%, 70%, 80%, 90%, 100%, 150%, 200%, 250%, 300%, 350%, 400%, 500%, 600%, 700%, 800%, 900%, 1000% or more) compared to a corresponding method that includes expressing a nucleic acid construct including a nucleotide sequence (e.g., encoding a first protein) operably linked to a first promoter element, where the first promoter element lacks any mutation lacks any mutation in a nucleotide position corresponding to nucleotide positions T688, A696, T702, A712, and T714 relative to SEQ ID NO: 28. In some embodiments, the titer of a product (e.g., a protein) can be increased by at least 5% (e.g., at least 6%, 7%, 8%, 9%, 10%, 15%, 20%, 30%, 40%, 50%, 60%, 70%, 80%, 90%, 100%, 150%, 200%, 250%, 300%, 350%, 400%, 500%, 600%, 700%, 800%, 900%, 1000% or more) compared to a corresponding method that includes expressing a nucleic acid construct including a nucleotide sequence (e.g., encoding a first protein) operably linked to a first promoter element, where the first promoter element lacks any mutation lacks any mutation in a nucleotide position corresponding to nucleotide positions 688, 696, 702, 712, and 714 relative to SEQ ID NO: 28.

Generally, a "titer" is the measurement of the amount of a substance in solution. As used herein, the "titer" of a heme-binding protein refers to the overall amount of the polypeptide, whether or not it is bound to heme, unless otherwise specified. The titer of a product (e.g., a protein) can be measured by any suitable method, such as high-performance liquid chromatography (HPLC), high-performance liquid chromatography-mass spectrometry (HPLC-MS), enzyme-linked immunosorbent assay (ELISA), or ultraviolet and/or visible light spectroscopy.

As used herein, a "corresponding method" is a method that is essentially identical to a reference method in all ways except for the identified difference. For example, a corresponding method for expressing a nucleic acid construct including a nucleotide sequence (e.g., encoding a first protein) operably linked to a first promoter element, where the first promoter element lacks one or more mutations corresponding to a mutation in a nucleotide position corresponding to nucleotide positions 668-734 (e.g., nucleotide positions 673-729, nucleotide positions 678-724, nucleotide positions 683-719, or nucleotide positions 688-714) relative to SEQ ID NO: 28 would essentially be the same as the reference method in all aspects (e.g., genetic makeup of cell, temperature and time of culture, and so forth), except that the corresponding method would express a nucleic acid construct including a nucleotide sequence (e.g., encoding a first protein) operably linked to a first promoter element that lacks any mutations corresponding to a mutation in a nucleotide position corresponding to nucleotide positions 668-734 (e.g., nucleotide positions 673-729, nucleotide positions 678-724, nucleotide positions 683-719, or nucleotide positions 688-714) relative to SEQ ID NO: 28. For example, a corresponding method for expressing a nucleic acid construct including a nucleotide sequence (e.g., encoding a first protein) operably linked to a first promoter element, where the first promoter element lacks one or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28 would essentially be the same as the reference method in all aspects (e.g., genetic makeup of cell, temperature and time of culture, and so forth), except that the corresponding method would express a nucleic acid construct including a nucleotide sequence (e.g., encoding a first protein) operably linked to a first promoter element that lacks any of the mutations included in the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28. For example, a corresponding method for expressing a nucleic acid construct including a nucleotide sequence (e.g., encoding a first protein) operably linked to a first promoter element, where the first promoter element lacks one or more mutations at a nucleotide position corresponding to nucleotide positions T146, C154, T303, T426, A433, A435, T530, C572, T596, T617, T688, A696, T702, A709, A712, T714, A790, A841, and T862 relative to SEQ ID NO: 28 would essentially be the same as the reference method in all aspects (e.g., genetic makeup of cell, temperature and time of culture, and so forth), except that the corresponding method would express a nucleic acid construct including a nucleotide sequence (e.g., encoding a first protein) operably linked to a first promoter element that lacks any of the mutations at a nucleotide position corresponding to nucleotide positions T146, C154, T303, T426, A433, A435, T530, C572, T596, T617, T688, A696, T702, A709, A712, T714, A790, A841, and T862 relative to SEQ ID NO: 28. For example, a corresponding method for expressing a nucleic acid construct including a nucleotide sequence (e.g., encoding a first protein) operably linked to a first promoter element, where the first promoter element lacks one or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28 would essentially be the same as the reference method in all aspects (e.g., genetic makeup of cell, temperature and time of culture, and so forth), except that the corresponding method would express a nucleic acid construct including a nucleotide sequence (e.g., encoding a first protein) operably linked to a first promoter element that lacks any of the mutations included in the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28. For example, a corresponding method for expressing a nucleic acid construct including a nucleotide sequence (e.g., encoding a first protein) operably linked to a first promoter element, where the first promoter element lacks one or more mutations at a nucleotide position corresponding to nucleotide positions 146, 154, 303, 426, 433, 435, 530, 572, 596, 617, 688, 696, 702, 709, 712, 714, 790, 841, and 862 relative to SEQ ID NO: 28 would essentially be the same as the reference method in all aspects (e.g., genetic makeup of cell, temperature and time of culture, and so forth), except that the corresponding method would express a nucleic acid construct including a nucleotide sequence (e.g., encoding a first protein) operably linked to a first promoter element that lacks any of the mutations at a nucleotide position corresponding to nucleotide positions 146, 154, 303, 426, 433, 435, 530, 572, 596, 617, 688, 696, 702, 709, 712, 714, 790, 841, and 862 relative to SEQ ID NO: 28.

For example, a corresponding method for expressing a nucleic acid construct including a nucleotide sequence (e.g., encoding a first protein) operably linked to a first promoter element, where the first promoter element lacks one or more mutations selected from the group consisting of mutations corresponding to T688C, A696T, T702C, A712G, and T714G relative to SEQ ID NO: 28 would essentially be the same as the reference method in all aspects (e.g., genetic makeup of cell, temperature and time of culture, and so forth), except that the corresponding method would express a nucleic acid construct including a nucleotide sequence (e.g., encoding a first protein) operably linked to a first promoter element that lacks any of the mutations included in the group consisting of mutations corresponding to T688C, A696T, T702C, A712G, and T714G relative to SEQ ID NO: 28. For example, a corresponding method for expressing a nucleic acid construct including a nucleotide sequence (e.g., encoding a first protein) operably linked to a first promoter element, where the first promoter element lacks one or more mutations selected from the group consisting of mutations corresponding to 688C, 696T, 702C, 712G, and 714G relative to SEQ ID NO: 28 would essentially be the same as the reference method in all aspects (e.g., genetic makeup of cell, temperature and time of culture, and so forth), except that the corresponding method would express a nucleic acid construct including a nucleotide sequence (e.g., encoding a first protein) operably linked to a first promoter element that lacks any of the mutations included in the group consisting of mutations corresponding to 688C, 696T, 702C, 712G, and 714G relative to SEQ ID NO: 28. For example, a corresponding method for expressing a nucleic acid construct including a nucleotide sequence (e.g., encoding a first protein) operably linked to a first promoter element, where the first promoter element lacks one or more mutations at a nucleotide position corresponding to nucleotide positions T688, A696, T702, A712, and T714 relative to SEQ ID NO: 28 would essentially be the same as the reference method in all aspects (e.g., genetic makeup of cell, temperature and time of culture, and so forth), except that the corresponding method would express a nucleic acid construct including a nucleotide sequence (e.g., encoding a first protein) operably linked to a first promoter element that lacks any of the mutations included in the group consisting of mutations corresponding to T688, A696, T702, A712, and T714 relative to SEQ ID NO: 28. For example, a corresponding method for expressing a nucleic acid construct including a nucleotide sequence (e.g., encoding a first protein) operably linked to a first promoter element, where the first promoter element lacks one or more mutations at a nucleotide position corresponding to nucleotide positions 688, 696, 702, 712, and 714 relative to SEQ ID NO: 28 would essentially be the same as the reference method in all aspects (e.g., genetic makeup of cell, temperature and time of culture, and so forth), except that the corresponding method would express a nucleic acid construct including a nucleotide sequence (e.g., encoding a first protein) operably linked to a first promoter element that lacks any of the mutations included in the group consisting of mutations corresponding to 688, 696, 702, 712, and 714 relative to SEQ ID NO: 28.

Genetically engineering a cell (e.g., a yeast cell (e.g., a methylotrophic yeast cell) typically includes introducing a recombinant nucleic acid molecule (also called a nucleic acid construct) into the cell. As described herein, a recombinant nucleic acid molecule typically includes an exogenous nucleic acid that encodes a product (e.g., a protein (e.g., a protein involved in heme biosynthesis, a heme-binding protein, or a transcription factor)) operably linked to at least one promoter element (e.g., an inducible or constitutive promoter element). In some embodiments, a recombinant nucleic acid molecule can include a linear sequence of two or more protein-coding sequences operably linked to the same or separate promoter elements (e.g., a first promoter operably linked to a first nucleic acid construct including a nucleotide sequence (e.g., encoding a first protein) and a second promoter operably linked to a second nucleic acid construct including a nucleotide sequence (e.g., encoding a second protein), or a promoter operably linked to a first nucleic acid construct including a nucleotide sequence (e.g., encoding a first protein) and a second nucleic acid construct including a nucleotide sequence (e.g., encoding a second protein)). In some cases, a recombinant nucleic acid molecule including at least one promoter operably linked to a nucleotide sequence (e.g., encoding a protein) can be called a cassette.

A recombinant nucleic acid can include expression elements. Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins.

Nucleic acids can be detected using any number of amplification techniques (see, e.g., *PCR Primer: A Laboratory Manual,* 1995, Dieffenbach & Dveksler, Eds., Cold Spring Harbor Laboratory Press, Cold Spring Harbor, NY; and U.S. Pat. Nos. 4,683,195; 4,683,202; 4,800,159; and 4,965,188) with an appropriate pair of oligonucleotides (e.g., primers). A number of modifications to the original PCR method have been developed and can be used to detect selected nucleic acids.

Suitable transcription factors, and nucleic acids encoding transcription factors (e.g., exogenous nucleic acids encoding transcription factors) include, for example, Mxr1 from *Pichia pastoris*. A representative *P. pastoris* Mxr1 nucleic acid sequence can be found, for example, in GenBank Accession No. DQ395124, while a representative *P. pastoris* Mxr1 polypeptide sequence can be found, for example, in GenBank Accession No. ABD57365). In some embodiments, the transcription factor can be a Mit1 sequence from *P. pastoris* (see, for example, GenBank Accession No. CAY70887). Suitable transcription factors also can be found in *Hansenula polymorpha* (e.g., Adr1; see, for example, GenBank Accession No. AEOI02000005, bases 858873 to 862352, for the nucleic acid sequence and GenBank Accession No. ESX01253 for the amino acid sequence) and *Candida boidinii* (e.g., Trm1; see, for example, GenBank Accession No. AB365355 for the nucleic acid sequence and GenBank Accession No. BAF99700 for the amino acid sequence; and Trm2; see, for example, GenBank Accession No. AB548760 for the nucleic acid sequence and GenBank Accession No. BAJ07608 for the amino acid sequence).

Transcription factors such as Mxr1 may be normally expressed at low levels. In some embodiments, it is desirable to place the exogenous nucleic acid (e.g., the transcription factor) under control of a promoter that is inducible.

In some embodiments, a transcription factor can bind to a promoter element as described herein and activate transcription from the promoter element. In some embodiments, when a nucleic acid sequence encoding the transcription factor is operably linked to a promoter element to which it binds, a positive feedback loop can be created to help drive expression of other nucleic acid sequences (e.g., protein-encoding nucleic acid sequences) operably linked to the promoter. Non-limiting examples of transcription factors that can be used with an AOX1 promoter (e.g., a mutated AOX1 promoter) include Mxr1, Mit1, Adr1, Trm1, Trm2, and combinations thereof. In some embodiments, a transcription factor that can be used with an AOX1 promoter can include Mxr1. A non-limiting example of a transcription factor that can be used with an MOX promoter (e.g., a mutated MOX promoter) is Adr1. Non-limiting examples of transcription factors that can be used with an AOD1 promoter (e.g., a mutated AOD1 promoter) include Trm1, Trm2, or a combination thereof. In some embodiments, two methanol-regulated transcription factors (e.g., Mxr1 and Mit1) can be operably linked to a methanol inducible promoter element (e.g., pAOX1).

The recombinant nucleic acid molecules described herein can be stably integrated into the genome of the cell (e.g., yeast cell (e.g., methylotrophic yeast cell), or can be extra-chromosomally expressed from a replication-competent plasmid. Methods of achieving both are well known and routinely used in the art.

In addition, it is noted that a first nucleic acid construct including a nucleotide sequence (e.g., encoding a first protein (e.g., a heme-binding protein)) operably linked to a promoter element (e.g., a promoter element as described herein) can be physically separate from a second nucleic acid construct including a nucleotide sequence (e.g., encoding a second protein (e.g., a transcription factor)) operably linked to a promoter element (e.g., a promoter element as described herein) (that is, the first and second nucleic acid constructs can be completely separate molecules). Alternatively, a first nucleic acid construct including a nucleotide sequence (e.g., encoding a first protein) operably linked to a promoter element (e.g., a promoter element as described herein) and a second nucleic acid construct including a nucleotide sequence (e.g., encoding a second protein) operably linked to a promoter element (e.g., a promoter element as described herein) can be included in the same nucleic acid construct. In some embodiments, a first nucleic acid construct including a nucleotide sequence (e.g., encoding a first protein) operably linked to a promoter element can be contiguous with a second nucleic acid construct including a nucleotide sequence (e.g., encoding a second protein) operably linked to a promoter element. It would be appreciated by a skilled artisan that, if the second nucleic acid construct including a nucleotide sequence (e.g., encoding a second protein) is contiguous with the first nucleic acid construct including a nucleotide sequence (e.g., encoding a protein of interest), a single promoter, or promoter element therefrom, can be used to drive transcription of both or all of the nucleotide sequences (e.g., a nucleic acid encoding the first protein as well as a second protein).

Methods of introducing nucleic acids into cells (e.g., yeast cells (e.g., methylotrophic yeast cells)) are known in the art, and include, without limitation, transduction, electroporation, biolistic particle delivery, and chemical transformation. Methods of culturing cells (e.g., yeast cells (e.g., methylotrophic yeast cells)) also are known in the art. See, for example, *Pichia* Protocols, *Methods In Molecular Biology*, 389, Cregg, Ed., 2007, $2^{nd}$ Ed., Humana Press, Inc. Under some circumstances, it may be desirable to introduce or add methanol to the culture media, although, as demonstrated herein, methanol is not required to obtain efficient expression at high levels of one or more products (e.g., proteins) of interest. Under some circumstances (e.g., when one or more nucleic acids encoding enzyme(s) involved in heme biosynthesis are expressed), it may be desirable to supplement the culture media with iron or a pharmaceutically or metabolically acceptable (or GRAS) salt thereof.

The methods provided herein also can include purifying an expressed protein. As used herein, an "enriched" protein is a protein that accounts for at least 5% (e.g., at least 6%, 7%, 8%, 9%, 10%, 15%, 20%, 25%, 30%, 35%, 40%, 45%, 50%, 55%, 60%, or more) by dry weight, of the mass of the production cell, or at least 10% (e.g., at least 15%, 20%, 25%, 30%, 35%, 40%, 45%, 50%, 55%, 60%, 65%, 70%, 75%, 80%, 90%, 95%, or 99%) by dry weight, the mass of the production cell lysate (e.g., excluding cell wall or membrane material). As used herein, a "purified" protein is a protein that has been separated from cellular components that naturally accompany it. Typically, the protein is considered "purified" when it is at least 70% (e.g., at least 75%, 80%, 85%, 90%, 95%, or 99%) by dry weight, free from other proteins and naturally occurring molecules with which it is naturally associated.

As used herein, nucleic acids can include DNA and RNA, and includes nucleic acids that contain one or more nucleotide analogs or backbone modifications. A nucleic acid can be single stranded or double stranded, which usually depends upon its intended use. Also provided are nucleic acids and polypeptides that differ from a given sequence. Nucleic acids and polypeptides can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to a given nucleic acid or polypeptide sequence. In some embodiments, a nucleic acid or polypeptide can have 100% sequence identity to a given nucleic acid or polypeptide sequence.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, *Nucleic Acids Res.,* 31(13):3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule, thereby leading to changes in the amino acid sequence of the encoded polypeptide. For example, changes can be introduced into nucleic acid coding sequences using mutagenesis (e.g., site-directed mutagenesis, PCR-mediated mutagenesis, transposon mutagenesis, chemical mutagenesis, UV mutagenesis or radiation induced mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al., 1978, *Atlas of Protein Sequence and Structure,* 5(Suppl. 3):345-352, which provides frequency tables for amino acid substitutions), and a non-conservative substitution is one in which an amino acid residue is replaced with an amino acid residue that does not have a similar side chain. Nucleic acid and/or polypeptide sequences may be modified as described herein to improve one or more properties such as, without limitation, increased expression (e.g., transcription and/or translation), tighter regulation, deregulation, loss of catabolite repression, modified specificity, secretion, thermostability, solvent stability, oxidative stability, protease resistance, catalytic activity, and/or color.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A construct or vector containing a nucleic acid construct as described herein (e.g., a nucleotide sequence that encodes a polypeptide operably linked to a promoter element as described herein) also is provided. Constructs or vectors, including expression constructs or vectors, are commercially available or can be produced by recombinant DNA techniques routine in the art. A construct or vector containing a nucleic acid can have expression elements operably linked to such a nucleic acid, and further can include sequences such as those encoding a selectable marker (e.g., an antibiotic resistance gene). A construct or vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST)).

Nucleic acids also can be detected using hybridization. Hybridization between nucleic acids is discussed in detail in Sambrook et al. (1989, *Molecular Cloning: A Laboratory Manual,* 2nd Ed., Cold Spring Harbor Laboratory Press, Cold Spring Harbor, NY; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, CA).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Methods are described herein that can be used to generate a strain that lacks sequences for selection (i.e., that lacks a selectable marker). These methods include using a circular plasmid DNA vector and a linear DNA sequence; the circular plasmid DNA vector contains a selection marker and an origin of DNA replication (also known as an autonomously replicating sequence (ARS)), and the linear DNA sequence contains sequences for integration into the *Pichia* genome by homologous recombination. A linear DNA molecule additionally can include nucleic acid sequences encoding one or more proteins of interest such as, without limitation, heme-bound LegH, a dehydrin, a phytase, a protease a catalase, a lipase, a peroxidase, an amylase, a transglutaminase, an oxidoreductase, a transferase, a hydrolase, a lyase, an isomerase, a ligase, one or more enzymes involved in the pathway for production of small molecules, such as ethanol, lactic acid, butanol, adipic acid or succinic acid, or an antibody against any such proteins.

Cells (e.g., yeast cells (e.g., methylotrophic yeast cells (e.g., *Pichia*))) can be transformed with both DNA molecules and the transformants selected by the presence of the selectable marker on the circular plasmid. Transformants then can be screened for integration of the linear DNA molecule into the genome using, for example, PCR. Once transformants with the correct integration of the marker-free linear DNA molecule are identified, the cells can be grown in the absence of selection for the circular plasmid. Because the marker-bearing plasmid is not stably maintained in the absence of selection, the plasmid is lost, often very quickly, after selection is relaxed. The resulting strain carries the integrated linear DNA in the absence of heterologous sequences for selection. Therefore, this approach can be used to construct strains (e.g., *Pichia* strains) that lack a selectable marker (e.g., a heterologous selection marker) with little to no impact on recombinant product (e.g., protein) yield.

In accordance with the present disclosure, there may be employed conventional molecular biology, microbiology, biochemical, and recombinant DNA techniques within the skill of the art. Such techniques are explained fully in the literature. The materials and methods of the disclosure will be further described in the following examples, which do not limit the scope of the methods and compositions of matter described in the claims.

EXEMPLARY EMBODIMENTS

Embodiment 1 is a nucleic acid construct comprising a first alcohol oxidase promoter element, wherein the first alcohol oxidase promoter element comprises a mutation at one or more nucleotide positions corresponding to any of nucleotide positions 668-734 relative to SEQ ID NO: 28.

Embodiment 2 is the nucleic acid construct of embodiment 1, wherein the first alcohol oxidase promoter element comprises a mutation at one or more nucleotide positions corresponding to any of nucleotide positions 673-729 relative to SEQ ID NO: 28.

Embodiment 3 is the nucleic acid construct of embodiment 1, wherein the first alcohol oxidase promoter element comprises a mutation at one or more nucleotide positions corresponding to any of nucleotide positions 678-724 relative to SEQ ID NO: 28.

Embodiment 4 is the nucleic acid construct of embodiment 1, wherein the first alcohol oxidase promoter element comprises a mutation at one or more nucleotide positions corresponding to any of nucleotide positions 683-719 relative to SEQ ID NO: 28.

Embodiment 5 is the nucleic acid construct of embodiment 1, wherein the first alcohol oxidase promoter element comprises a mutation at one or more nucleotide positions corresponding to any of nucleotide positions 688-714 relative to SEQ ID NO: 28.

Embodiment 6 is the nucleic acid construct of embodiment 1, wherein the first alcohol oxidase promoter element comprises two or more mutations at nucleotide positions corresponding to any of nucleotide positions 668-734 relative to SEQ ID NO: 28.

Embodiment 7 is the nucleic acid construct of embodiment 1, wherein the first alcohol oxidase promoter element comprises three or more mutations at nucleotide positions corresponding to any of nucleotide positions 668-734 relative to SEQ ID NO: 28.

Embodiment 8 is the nucleic acid construct of embodiment 1, wherein the first alcohol oxidase promoter element comprises four or more mutations at nucleotide positions corresponding to any of nucleotide positions 668-734 relative to SEQ ID NO: 28.

Embodiment 9 is the nucleic acid construct of embodiment 1, wherein the first alcohol oxidase promoter element comprises five or more mutations at nucleotide positions corresponding to any of nucleotide positions 668-734 relative to SEQ ID NO: 28.

Embodiment 10 is the nucleic acid construct of embodiment 1, wherein the first alcohol oxidase promoter has the sequence of SEQ ID NO: 29.

Embodiment 11 is a nucleic acid construct comprising a first alcohol oxidase promoter element, wherein the first alcohol oxidase promoter element comprises one or more mutations at a nucleotide position selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Embodiment 12 is the nucleic acid construct of embodiment 11, wherein the first alcohol oxidase promoter element comprises two or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Embodiment 13 is the nucleic acid construct of embodiment 11, wherein the first alcohol oxidase promoter element comprises three or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Embodiment 14 is the nucleic acid construct of embodiment 11, wherein the first alcohol oxidase promoter element comprises four or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Embodiment 15 is the nucleic acid construct of embodiment 11, wherein the first alcohol oxidase promoter element comprises five or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Embodiment 16 is the nucleic acid construct of any one of embodiments 11-15, wherein the first alcohol oxidase promoter element comprises one or more mutations at a nucleotide position selected from the group consisting of nucleotide positions corresponding to T688, A696, T702, A712, and T714 relative to SEQ ID NO: 28.

Embodiment 17 is the nucleic acid construct of any one of embodiments 11-15, wherein the first alcohol oxidase promoter element comprises two or more mutations at nucleotide positions selected from the group consisting of nucleotide positions corresponding to T688, A696, T702, A712, and T714 relative to SEQ ID NO: 28.

Embodiment 18 is the nucleic acid construct of any one of embodiments 11-15, wherein the first alcohol oxidase promoter element comprises three or more mutations at nucleotide positions selected from the group consisting of nucleotide positions corresponding to T688, A696, T702, A712, and T714 relative to SEQ ID NO: 28.

Embodiment 19 is the nucleic acid construct of any one of embodiments 11-15, wherein the first alcohol oxidase promoter element comprises four or more mutations at nucleotide positions selected from the group consisting of nucleotide positions corresponding to T688, A696, T702, A712, and T714 relative to SEQ ID NO: 28.

Embodiment 20 is the nucleic acid construct of any one of embodiments 11-15, wherein the first alcohol oxidase promoter element comprises mutations at nucleotide positions corresponding to T688, A696, T702, A712, and T714 relative to SEQ ID NO: 28.

Embodiment 21 is a nucleic acid construct comprising a first alcohol oxidase promoter element, wherein the first alcohol oxidase promoter element comprises one or more mutations at a nucleotide position selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28.

Embodiment 22 is the nucleic acid construct of embodiment 21, wherein the first alcohol oxidase promoter element comprises two or more mutations at nucleotide positions selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28.

Embodiment 23 is the nucleic acid construct of embodiment 21, wherein the first alcohol oxidase promoter element comprises three or more mutations at nucleotide positions selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28.

Embodiment 24 is the nucleic acid construct of embodiment 21, wherein the first alcohol oxidase promoter element comprises four or more mutations at nucleotide positions selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28.

Embodiment 25 is the nucleic acid construct of embodiment 21, wherein the first alcohol oxidase promoter element comprises five or more mutations at nucleotide positions selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28.

Embodiment 26 is the nucleic acid construct of any one of embodiments 21-25, wherein the first alcohol oxidase promoter element comprises one or more mutations at a nucleotide position selected from the group consisting of nucleotide positions corresponding to 688, 696, 702, 712, and 714 relative to SEQ ID NO: 28.

Embodiment 27 is the nucleic acid construct of any one of embodiments 21-25, wherein the first alcohol oxidase promoter element comprises two or more mutations at nucleotide positions selected from the group consisting of nucleotide positions corresponding to 688, 696, 702, 712, and 714 relative to SEQ ID NO: 28.

Embodiment 28 is the nucleic acid construct of any one of embodiments 21-25, wherein the first alcohol oxidase promoter element comprises three or more mutations at nucleotide positions selected from the group consisting of nucleotide positions corresponding to 688, 696, 702, 712, and 714 relative to SEQ ID NO: 28.

Embodiment 29 is the nucleic acid construct of any one of embodiments 21-25, wherein the first alcohol oxidase promoter element comprises four or more mutations at nucleotide positions selected from the group consisting of nucleotide positions corresponding to 688, 696, 702, 712, and 714 relative to SEQ ID NO: 28.

Embodiment 30 is the nucleic acid construct of any one of embodiments 21-25, wherein the first alcohol oxidase promoter element comprises mutations at nucleotide positions corresponding to 688, 696, 702, 712, and 714 relative to SEQ ID NO: 28.

Embodiment 31 is a nucleic acid construct comprising a first alcohol oxidase promoter element, wherein the first alcohol oxidase promoter element comprises one or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Embodiment 32 is the nucleic acid construct of embodiment 31, wherein the first alcohol oxidase promoter element comprises two or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Embodiment 33 is the nucleic acid construct of embodiment 31, wherein the first alcohol oxidase promoter element comprises three or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Embodiment 34 is the nucleic acid construct of embodiment 31, wherein the first alcohol oxidase promoter element comprises four or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Embodiment 35 is the nucleic acid construct of embodiment 31, wherein the first alcohol oxidase promoter element comprises five or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Embodiment 36 is the nucleic acid construct of any one of embodiments 1-35, wherein the first alcohol oxidase promoter element comprises one or more mutations selected from the group consisting of T688C, A696T, T702C, A712G, and T714G relative to SEQ ID NO: 28.

Embodiment 37 is the nucleic acid construct of any one of embodiments 1-35, wherein the first alcohol oxidase promoter element comprises two or more mutations selected from the group consisting of T688C, A696T, T702C, A712G, and T714G relative to SEQ ID NO: 28.

Embodiment 38 is the nucleic acid construct of any one of embodiments 1-35, wherein the first alcohol oxidase promoter element comprises three or more mutations selected from the group consisting of T688C, A696T, T702C, A712G, and T714G relative to SEQ ID NO: 28.

Embodiment 39 is the nucleic acid construct of any one of embodiments 1-35, wherein the first alcohol oxidase promoter element comprises four or more mutations selected from the group consisting of T688C, A696T, T702C, A712G, and T714G relative to SEQ ID NO: 28.

Embodiment 40 is the nucleic acid construct of any one of embodiments 1-35, wherein the first alcohol oxidase promoter element comprises the mutations T688C, A696T, T702C, A712G, and T714G relative to SEQ ID NO: 28.

Embodiment 41 is a nucleic acid construct comprising a first alcohol oxidase promoter element, wherein the first alcohol oxidase promoter element comprises one or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28.

Embodiment 42 is the nucleic acid construct of embodiment 41, wherein the first alcohol oxidase promoter element comprises two or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28.

Embodiment 43 is the nucleic acid construct of embodiment 41, wherein the first alcohol oxidase promoter element comprises three or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28.

Embodiment 44 is the nucleic acid construct of embodiment 41, wherein the first alcohol oxidase promoter element comprises four or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28.

Embodiment 45 is the nucleic acid construct of embodiment 41, wherein the first alcohol oxidase promoter element comprises five or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28.

Embodiment 46 is the nucleic acid construct of any one of embodiments 1-45, wherein the first alcohol oxidase promoter element comprises one or more mutations selected from the group consisting of 688C, 696T, 702C, 712G, and 714G relative to SEQ ID NO: 28.

Embodiment 47 is the nucleic acid construct of any one of embodiments 1-45, wherein the first alcohol oxidase promoter element comprises two or more mutations selected from the group consisting of 688C, 696T, 702C, 712G, and 714G relative to SEQ ID NO: 28.

Embodiment 48 is the nucleic acid construct of any one of embodiments 1-45, wherein the first alcohol oxidase promoter element comprises three or more mutations selected from the group consisting of 688C, 696T, 702C, 712G, and 714G relative to SEQ ID NO: 28.

Embodiment 49 is the nucleic acid construct of any one of embodiments 1-45, wherein the first alcohol oxidase promoter element comprises four or more mutations selected from the group consisting of 688C, 696T, 702C, 712G, and 714G relative to SEQ ID NO: 28.

Embodiment 50 is the nucleic acid construct of any one of embodiments 1-45, wherein the first alcohol oxidase promoter element comprises the mutations 688C, 696T, 702C, 712G, and 714G relative to SEQ ID NO: 28.

Embodiment 51 is the nucleic acid construct of any one of embodiments 1-50, wherein the first alcohol oxidase promoter element is an alcohol oxidase promoter element from a promoter selected from the group consisting of AOX1, AOX2, AOD1, MOX, MOD1, and MOD2.

Embodiment 52 is the nucleic acid construct of any one of embodiments 1-51, wherein the first alcohol oxidase promoter element is an alcohol oxidase 1 (AOX1) promoter element.

Embodiment 53 is the nucleic acid construct of any one of embodiments 1-52, wherein the first alcohol oxidase promoter element has at least 90% sequence identity to SEQ ID NO: 28.

Embodiment 54 is the nucleic acid construct of any one of embodiments 1-52, wherein the first alcohol oxidase promoter element has at least 95% sequence identity to SEQ ID NO: 28.

Embodiment 55 is the nucleic acid construct of any one of embodiments 1-54, further comprising a nucleotide sequence, wherein the nucleotide sequence is operably linked to the first alcohol oxidase promoter element.

Embodiment 56 is the nucleic acid construct of embodiment 55, wherein the nucleotide sequence encodes a first protein.

Embodiment 57 is the nucleic acid construct of embodiment 56, wherein the first protein is exogenous to a methylotrophic yeast cell.

Embodiment 58 is the nucleic acid construct of embodiment 56 or embodiment 57, wherein the first protein is heterologous to a methylotrophic yeast cell.

Embodiment 59 is the nucleic acid construct of any one of embodiments 56-58, wherein the first protein is selected from the group consisting of an antibody or fragment thereof, an enzyme, a regulatory protein, a peptide hormone, a blood clotting protein, a cytokine, a cytokine inhibitor, and a heme-binding protein.

Embodiment 60 is the nucleic acid construct of any one of embodiments 56-59, wherein the first protein is a heme-binding protein.

Embodiment 61 is the nucleic acid construct of embodiment 60, wherein the heme-binding protein is selected from the group consisting of a globin, a cytochrome, a cytochrome c oxidase, a ligninase, a catalase, and a peroxidase.

Embodiment 62 is the nucleic acid construct of embodiment 60, wherein the heme-binding protein is selected from the group consisting of an androglobin, a chlorocruorin, a cytoglobin, an erythrocruorin, a flavohemoglobin, a globin E, a globin X, a globin Y, a hemoglobin, a histoglobin, a leghemoglobin, a myoglobin, a neuroglobin, a non-symbiotic hemoglobin, a protoglobin, and a truncated hemoglobin.

Embodiment 63 is the nucleic acid construct of embodiment 60, wherein the heme-binding protein is a non-symbiotic hemoglobin.

Embodiment 64 is the nucleic acid construct of embodiment 60, wherein the heme-binding protein is a leghemoglobin.

Embodiment 65 is the nucleic acid construct of embodiment 60, wherein the heme-binding protein comprises an amino acid sequence having at least 90% sequence identity to the amino acid sequence of any of SEQ ID NOs: 1-27.

Embodiment 66 is the nucleic acid construct of any one of embodiments 1-65, wherein the first alcohol oxidase promoter element comprises a recognition sequence for a transcription factor.

Embodiment 67 is a cell comprising a first nucleic acid construct, wherein the first nucleic acid construct is the nucleic acid construct of any one of embodiments 1-66.

Embodiment 68 is the cell of embodiment 67, wherein the cell is a yeast cell.

Embodiment 69 is the cell of embodiment 68, wherein the yeast cell is a methylotrophic yeast cell.

Embodiment 70 is the cell of embodiment 69, wherein the methylotrophic yeast cell is a *Pichia* cell, a *Candida* cell, a *Hansenula* cell, or a *Torulopsis* cell.

Embodiment 71 is the cell of embodiment 69 or embodiment 70, wherein the methylotrophic yeast cell is a *Pichia methanolica* cell, a *Pichia pastoris* cell, a *Candida boidinii* cell, or a *Hansenula polymorpha* cell.

Embodiment 72 is the cell of any one of embodiments 69-71, wherein the methylotrophic yeast cell is a *Pichia pastoris* cell.

Embodiment 73 is the cell of any one of embodiments 67-72, further comprising a second nucleic acid construct comprising a nucleotide sequence, wherein the nucleotide sequence is operably linked to the first alcohol oxidase promoter element or to a second promoter element.

Embodiment 74 is the cell of embodiment 73, wherein the nucleotide sequence of the second nucleic acid construct is operably linked to a second promoter element that has the same sequence as the first alcohol oxidase promoter element.

Embodiment 75 is the cell of any one of embodiments 73-74, wherein the nucleotide sequence of the second nucleic acid construct encodes a second protein.

Embodiment 76 is the cell of embodiment 75, wherein the second protein is a transcription factor.

Embodiment 77 is the cell of embodiment 76, wherein the nucleotide sequence encoding the second protein is operably linked to a second promoter element that comprises a recognition sequence for the transcription factor.

Embodiment 78 is the cell of embodiment 76 or embodiment 77, wherein the first alcohol oxidase promoter element comprises a recognition sequence for the transcription factor.

Embodiment 79 is the cell of any one of embodiments 75-78, wherein the second protein is a protein involved in heme biosynthesis.

Embodiment 80 is the cell of embodiment 79, wherein the protein involved in heme biosynthesis is selected from the group consisting of aminolevulinic acid synthase (ALAS), δ-aminolevulinic acid dehydratase (ALAD), porphogilinogen deaminase (PBGD), uroporphyrinogen III synthase (UPG3S), uroporphyrinogen III decarboxylase (UPG3D), coprotoporphyrinogen oxidase (COPROX), protoporphyrinogen IX oxidase (PROTOX), and ferrochelatase (FC).

Embodiment 81 is a method of producing a product in a cell comprising:
expressing a nucleic acid construct comprising a nucleotide sequence operably linked to a first alcohol oxidase promoter element, wherein the first alcohol oxidase promoter element comprises a mutation at one or more nucleotide positions corresponding to any of nucleotide positions 668-734 relative to SEQ ID NO: 28.

Embodiment 82 is the method of embodiment 81, wherein the first alcohol oxidase promoter element comprises a mutation at one or more nucleotide positions corresponding to any of nucleotide positions 673-729 relative to SEQ ID NO: 28.

Embodiment 83 is the method of embodiment 81, wherein the first alcohol oxidase promoter element comprises a mutation at one or more nucleotide positions corresponding to any of nucleotide positions 678-724 relative to SEQ ID NO: 28.

Embodiment 84 is the method of embodiment 81, wherein the first alcohol oxidase promoter element comprises a mutation at one or more nucleotide positions corresponding to any of nucleotide positions 683-719 relative to SEQ ID NO: 28.

Embodiment 85 is the method of embodiment 81, wherein the first alcohol oxidase promoter element comprises a mutation at one or more nucleotide positions corresponding to any of nucleotide positions 688-714 relative to SEQ ID NO: 28.

Embodiment 86 is the method of embodiment 81, wherein the first alcohol oxidase promoter element comprises two or more mutations at nucleotide positions corresponding to any of nucleotide positions 668-734 relative to SEQ ID NO: 28.

Embodiment 87 is the method of embodiment 81, wherein the first alcohol oxidase promoter element comprises three or more mutations at nucleotide positions corresponding to any of nucleotide positions 668-734 relative to SEQ ID NO: 28.

Embodiment 88 is the method of embodiment 81, wherein the first alcohol oxidase promoter element comprises four or more mutations at nucleotide positions corresponding to any of nucleotide positions 668-734 relative to SEQ ID NO: 28.

Embodiment 89 is the method of embodiment 81, wherein the first alcohol oxidase promoter element comprises five or more mutations at nucleotide positions corresponding to any of nucleotide positions 668-734 relative to SEQ ID NO: 28.

Embodiment 90 is the method of any one of embodiments 81-89, wherein a titer of the product produced by expressing a nucleic acid construct comprising a nucleotide sequence operably linked to a first alcohol oxidase promoter element, wherein the first alcohol oxidase promoter element comprises a mutation at one or more nucleotide positions corresponding to any of nucleotide positions 668-734 relative to SEQ ID NO: 28 is greater than a titer of the product produced expressing a nucleic acid construct comprising a nucleotide sequence operably linked to a first alcohol oxidase promoter element, wherein the first alcohol oxidase promoter element lacks any mutation at nucleotide positions corresponding to any of nucleotide positions 668-734 relative to SEQ ID NO: 28.

Embodiment 91 is a method of producing a product in a cell comprising:
expressing a nucleic acid construct comprising a nucleotide sequence operably linked to a first alcohol oxidase promoter element, wherein the first alcohol oxidase promoter element comprises one or more mutations at a nucleotide position selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Embodiment 92 is the method of embodiment 91, wherein the first alcohol oxidase promoter element comprises two or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Embodiment 93 is the method of embodiment 91, wherein the first alcohol oxidase promoter element includes three or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Embodiment 94 is the method of embodiment 91, wherein the first alcohol oxidase promoter element includes four or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Embodiment 95 is the method of embodiment 91, wherein the first alcohol oxidase promoter element includes five or more mutations at nucleotide positions selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Embodiment 96 is the method of any one of embodiments 91-95, wherein the first alcohol oxidase promoter element includes one or more mutations at a nucleotide position selected from the group consisting of nucleotide positions corresponding to of T688, A696, T702, A712, and T714 relative to SEQ ID NO: 28.

Embodiment 97 is the method of any one of embodiments 91-95, wherein the first alcohol oxidase promoter element includes two or more mutations at nucleotide positions selected from the group consisting of nucleotide positions corresponding to of T688, A696, T702, A712, and T714 relative to SEQ ID NO: 28.

Embodiment 98 is the method of any one of embodiments 91-95, wherein the first alcohol oxidase promoter element includes three or more mutations at nucleotide positions selected from the group consisting of nucleotide positions corresponding to of T688, A696, T702, A712, and T714 relative to SEQ ID NO: 28.

Embodiment 99 is the method of any one of embodiments 91-95, wherein the first alcohol oxidase promoter element includes four or more mutations at nucleotide positions selected from the group consisting of nucleotide positions corresponding to of T688, A696, T702, A712, and T714 as compared to SEQ ID NO: 28.

Embodiment 100 is the method of any one of embodiments 91-95, wherein the first alcohol oxidase promoter element includes mutations at nucleotide positions corresponding to T688, A696, T702, A712, and T714 as compared to SEQ ID NO: 28.

Embodiment 101 is the method of any one of embodiments 91-100, wherein a titer of the product produced by expressing a nucleic acid construct comprising a nucleotide sequence operably linked to a first alcohol oxidase promoter element, wherein the first alcohol oxidase promoter element comprises one or more mutations at a nucleotide position selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28 is greater than a titer of the product produced by expressing a nucleic acid construct comprising a nucleotide sequence encoding a first protein operably linked to a first alcohol oxidase promoter element, wherein the first alcohol oxidase promoter element lacks any mutations at a nucleotide position selected from the group consisting of nucleotide positions corresponding to T146, C154, T303, T426, A433, A435, T530, C572, T596, T617, T688, A696, T702, A709, A712, T714, A790, A841, and T862 relative to SEQ ID NO: 28.

Embodiment 102 is a method of producing a product in a cell comprising:
expressing a nucleic acid construct comprising a nucleotide sequence operably linked to a first alcohol oxidase promoter element, wherein the first alcohol oxidase promoter element comprises one or more mutations at a nucleotide position selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28.

Embodiment 103 is the method of embodiment 102, wherein the first alcohol oxidase promoter element comprises two or more mutations at nucleotide positions selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28.

Embodiment 104 is the method of embodiment 102, wherein the first alcohol oxidase promoter element includes three or more mutations at nucleotide positions selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28.

Embodiment 105 is the method of embodiment 102, wherein the first alcohol oxidase promoter element includes four or more mutations at nucleotide positions selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28.

Embodiment 106 is the method of embodiment 102, wherein the first alcohol oxidase promoter element includes five or more mutations at nucleotide positions selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28.

Embodiment 107 is the method of any one of embodiments 102-106, wherein the first alcohol oxidase promoter element includes one or more mutations at a nucleotide position selected from the group consisting of nucleotide positions corresponding to of 688, 696, 702, 712, and 714 relative to SEQ ID NO: 28.

Embodiment 108 is the method of any one of embodiments 102-106, wherein the first alcohol oxidase promoter element includes two or more mutations at nucleotide positions selected from the group consisting of nucleotide positions corresponding to of 688, 696, 702, 712, and 714 relative to SEQ ID NO: 28.

Embodiment 109 is the method of any one of embodiments 102-106, wherein the first alcohol oxidase promoter element includes three or more mutations at nucleotide positions selected from the group consisting of nucleotide positions corresponding to of 688, 696, 702, 712, and 714 relative to SEQ ID NO: 28.

Embodiment 110 is the method of any one of embodiments 102-106, wherein the first alcohol oxidase promoter element includes four or more mutations at nucleotide positions selected from the group consisting of nucleotide positions corresponding to of 688, 696, 702, 712, and 714 as compared to SEQ ID NO: 28.

Embodiment 111 is the method of any one of embodiments 102-106, wherein the first alcohol oxidase promoter element includes mutations at nucleotide positions corresponding to 688, 696, 702, 712, and 714 as compared to SEQ ID NO: 28.

Embodiment 112 is the method of any one of embodiments 102-111, wherein a titer of the product produced by expressing a nucleic acid construct comprising a nucleotide sequence operably linked to a first alcohol oxidase promoter element, wherein the first alcohol oxidase promoter element comprises one or more mutations at a nucleotide position selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28 is greater than a titer of the product produced by expressing a nucleic acid construct comprising a nucleotide sequence encoding a first protein operably linked to a first alcohol oxidase promoter element, wherein the first alcohol oxidase promoter element lacks any mutations at a nucleotide position selected from the group consisting of nucleotide positions corresponding to 146, 154, 303, 426, 433, 435, 530, 572, 596, 617, 688, 696, 702, 709, 712, 714, 790, 841, and 862 relative to SEQ ID NO: 28.

Embodiment 113 is a method of producing a product in a cell comprising:
expressing a nucleic acid construct comprising a nucleotide sequence operably linked to a first alcohol oxidase promoter element, wherein the first alcohol oxidase promoter element includes one or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Embodiment 114 is the method of embodiment 113, wherein the first alcohol oxidase promoter element includes two or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Embodiment 115 is the method of embodiment 113, wherein the first alcohol oxidase promoter element includes three or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Embodiment 116 is the method of embodiment 113, wherein the first alcohol oxidase promoter element includes four or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Embodiment 117 is the method of embodiment 113, wherein the first alcohol oxidase promoter element includes five or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Embodiment 118 is the method of any one of embodiments 113-117, wherein the titer of a product produced by expressing a nucleic acid construct comprising a nucleotide sequence operably linked to a first alcohol oxidase promoter element, wherein the first alcohol oxidase promoter element includes one or more mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28 is greater than the titer of a product produced by expressing a nucleic acid construct comprising a nucleotide sequence encoding a first protein operably linked to a first alcohol oxidase promoter element, wherein the first alcohol oxidase promoter element lacks any mutations selected from the group consisting of mutations corresponding to T146C, C154T, T303C, T426A, A433T, A435G, T530A, C572T, T596C, T617C, T688C, A696T, T702C, A709G, A712G, T714G, A790G, A841T, and T862A relative to SEQ ID NO: 28.

Embodiment 119 is the method of any one of embodiments 81-118, wherein the first alcohol oxidase promoter element comprises two or more mutations selected from the group consisting of T688C, A696T, T702C, A712G, and T714G relative to SEQ ID NO: 28.

Embodiment 120 is the method of any one of embodiments 81-118, wherein the first alcohol oxidase promoter element comprises three or more mutations selected from the group consisting of T688C, A696T, T702C, A712G, and T714G relative to SEQ ID NO: 28.

Embodiment 121 is the method of any one of embodiments 81-118, wherein the first alcohol oxidase promoter element comprises four or more mutations selected from the group consisting of T688C, A696T, T702C, A712G, and T714G relative to SEQ ID NO: 28.

Embodiment 122 is the method of any one of embodiments 81-118, wherein the first alcohol oxidase promoter element comprises the mutations T688C, A696T, T702C, A712G, and T714G relative to SEQ ID NO: 28.

Embodiment 123 is a method of producing a product in a cell comprising:
expressing a nucleic acid construct comprising a nucleotide sequence operably linked to a first alcohol oxidase promoter element, wherein the first alcohol oxidase promoter element includes one or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28.

Embodiment 124 is the method of embodiment 123, wherein the first alcohol oxidase promoter element includes two or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28.

Embodiment 125 is the method of embodiment 123, wherein the first alcohol oxidase promoter element includes three or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28.

Embodiment 126 is the method of embodiment 123, wherein the first alcohol oxidase promoter element includes four or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28.

Embodiment 127 is the method of embodiment 123, wherein the first alcohol oxidase promoter element includes five or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28.

Embodiment 128 is the method of any one of embodiments 123-127, wherein the titer of a product produced by expressing a nucleic acid construct comprising a nucleotide sequence operably linked to a first alcohol oxidase promoter element, wherein the first alcohol oxidase promoter element includes one or more mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28 is greater than the titer of a product produced by expressing a nucleic acid construct comprising a nucleotide sequence encoding a first protein operably linked to a first alcohol oxidase promoter element, wherein the first alcohol oxidase promoter element lacks any mutations selected from the group consisting of mutations corresponding to 146C, 154T, 303C, 426A, 433T, 435G, 530A, 572T, 596C, 617C, 688C, 696T, 702C, 709G, 712G, 714G, 790G, 841T, and 862A relative to SEQ ID NO: 28.

Embodiment 129 is the method of any one of embodiments 81-128, wherein the first alcohol oxidase promoter element comprises two or more mutations selected from the group consisting of 688C, 696T, 702C, 712G, and 714G relative to SEQ ID NO: 28.

Embodiment 130 is the method of any one of embodiments 81-128, wherein the first alcohol oxidase promoter element comprises three or more mutations selected from the group consisting of 688C, 696T, 702C, 712G, and 714G relative to SEQ ID NO: 28.

Embodiment 131 is the method of any one of embodiments 81-128, wherein the first alcohol oxidase promoter element comprises four or more mutations selected from the group consisting of 688C, 696T, 702C, 712G, and 714G relative to SEQ ID NO: 28.

Embodiment 132 is the method of any one of embodiments 81-128, wherein the first alcohol oxidase promoter element comprises the mutations 688C, 696T, 702C, 712G, and 714G relative to SEQ ID NO: 28.

Embodiment 133 is a method of producing a product in a cell comprising:
expressing a nucleic acid construct comprising a nucleotide sequence operably linked to a first alcohol oxidase promoter element, wherein the first alcohol oxidase promoter element is the nucleic acid construct of any one of embodiments 1-54.

Embodiment 134 is the method of any one of embodiments 81-133, wherein the first alcohol oxidase promoter element is an alcohol oxidase promoter element from a promoter selected from the group consisting of AOX1, AOX2, AOD1, MOX, MOD1, and MOD2.

Embodiment 135 is the method of any one of embodiments 81-134, wherein the first alcohol oxidase promoter element is an alcohol oxidase 1 (AOX1) promoter element.

Embodiment 136 is the method of any one of embodiments 81-135, wherein the first alcohol oxidase promoter element has at least 90% sequence identity to SEQ ID NO: 28.

Embodiment 137 is the method of any one of embodiments 55-135, wherein the first alcohol oxidase promoter element has at least 95% sequence identity to SEQ ID NO: 28.

Embodiment 138 is the method of any one of embodiments 81-137, wherein the first alcohol oxidase promoter element has the sequence of SEQ ID NO: 29.

Embodiment 139 is the method of any one of embodiments 81-138, wherein the cell is a yeast cell.

Embodiment 140 is the method of embodiment 139, wherein the yeast cell is a methylotrophic yeast cell.

Embodiment 141 is the method of any one of embodiments 81-140, wherein the nucleotide sequence operably linked to the first alcohol oxidase promoter element encodes a first protein.

Embodiment 142 is the method of embodiment 141, wherein the first protein is exogenous to the cell.

Embodiment 143 is the method of any one of embodiments 141-142, wherein the first protein is heterologous to the cell.

Embodiment 144 is the method of any one of embodiments 141-143, wherein the first protein is selected from the group consisting of an antibody or fragment thereof, an enzyme, a regulatory protein, a peptide hormone, a blood clotting protein, a cytokine, and a heme-binding protein.

Embodiment 145 is the method of any one of embodiments 141-144, wherein the first protein is a heme-binding protein.

Embodiment 146 is the method of embodiment 145, wherein the heme-binding protein is selected from the group consisting of a globin, a cytochrome, a cytochrome c oxidase, a ligninase, a catalase, and a peroxidase.

Embodiment 147 is the method of embodiment 145, wherein the heme-binding protein is selected from the group consisting of an androglobin, a chlorocruorin, a cytoglobin, an erythrocruorin, a flavohemoglobin, a globin E, a globin X, a globin Y, a hemoglobin, a histoglobin, a leghemoglobin, a myoglobin, a neuroglobin, a non-symbiotic hemoglobin, a protoglobin, and a truncated hemoglobin.

Embodiment 148 is the method of embodiment 145, wherein the heme-binding protein is a non-symbiotic hemoglobin.

Embodiment 149 is the method of embodiment 145, wherein the heme-binding protein is a leghemoglobin.

Embodiment 150 is the method of embodiment 145, wherein the heme-binding protein comprises an amino acid sequence having at least 90% sequence identity to an amino acid sequence in any one of SEQ ID NOs: 1-27.

Embodiment 151 is the method of any one of embodiments 81-150, wherein the first alcohol oxidase promoter element contains one or more recognition sequences for a transcription factor.

Embodiment 152 is the method of any one of embodiments 81-151, further comprising expressing a second nucleic acid construct comprising a nucleotide sequence, wherein the nucleotide sequence of the second nucleic acid construct is operably linked to the first alcohol oxidase promoter element or to a second promoter element.

Embodiment 153 is the method of embodiment 152, wherein the nucleotide sequence of the second nucleic acid construct is operably linked to a second promoter element that has the same sequence as the first alcohol oxidase promoter element.

Embodiment 154 is the method of any one of embodiments 152-153, wherein the nucleotide sequence of the second nucleic acid construct encodes a second protein.

Embodiment 155 is the method of embodiment 154, wherein the second protein is a transcription factor.

Embodiment 156 is the method of embodiment 155, wherein the nucleotide sequence encoding the second protein is operably linked to a second promoter element that comprises a recognition sequence for the transcription factor.

Embodiment 157 is the method of embodiment 155, wherein the first alcohol oxidase promoter element comprises a recognition sequence for the transcription factor.

Embodiment 158 is the method of 154, wherein the second protein is a protein involved in heme biosynthesis.

Embodiment 159 is the method of embodiment 158, wherein the protein involved in heme biosynthesis is selected from the group consisting of ALAS, ALAD, PBGD, UPG3S, UPG3D, COPROX, PROTOX, and FC.

Embodiment 160 is the method of any one of embodiments 81-159, wherein the method is carried out in the absence of added methanol.

The materials and methods of the disclosure will be further described in the following Examples, which do not limit the scope the claims.

EXAMPLES

Example 1

Polymerase Chain Reaction

Genes of interest were amplified from genomic DNA or plasmid DNA templates using Phusion Hi-fidelity DNA polymerase (New England Biolabs). Briefly, 0.6 µM each of forward and reverse primers were incubated with 10-50 ng of template DNA and 400 µM of nucleotide mix in the presence of 1-2 U of Phusion DNA polymerase. The reaction conditions were as follows:

| | | | |
|---|---|---|---|
| 1 cycle | Initial Denaturation | 98° C. | 1 min |
| 25 cycles | Denaturation | 98° C. | 10 sec |
| | Annealing | | 20 sec |
| | Extension | 72° C. | 30 sec per kb |
| 1 cycle | Final Extension | 72° C. | 5 min |
| 1 cycle | Hold | 4° C. | Forever |

Example 2

Plasmid Construction by Ligation 50-100 ng of restriction enzyme digested plasmid and 3× molar excess of PCR amplified inserts were incubated in the presence of T4 DNA ligase (New England Biolabs). Ligation was carried out at 16° C. for greater than 2 hr. 2 µl of ligation reaction was transformed into DH10B electrocompetent *E. coli* cells.

Example 3

Transformation into *E. coli* ElectroMax DH10B T1 Phage-Resistant Competent Cells 1.5-2 µl of ligation mixture (Example 2) was transformed into 20 µl of ElectroMax DH10B T1 Phage-Resistant Competent Cells (Invitrogen, Cat #12033-015) by electroporation using MicroPulser (BioRad) set at 1.7 kV using a 1 mm gap cuvette (BioRad, Cat #165-2089); after a pulse, 1 ml SOC (super optimal broth with catabolite repression) was added to cells and cells were incubated at 37° C. for 1 h with shaking at 200 rpm. 10 µl of recovery mixture was plated on LB (lysogeny broth) agar plates containing ampicillin at a concentration of 100 µg/ml. Plates were incubated overnight at 37° C. Plasmids were isolated and purified using a NUCLEOSPIN® plasmid kit from Macherev-Nagel, according to the manufacturer's instructions.

Example 4

Preparation of *P. pastoris* Transformation-Competent Cells

Selected strains of *P. pastoris* were grown to mid-exponential growth phase (about 2 OD) in 25 ml YPD (yeast extract-peptone-dextrose) medium. Cells were collected by centrifugation at 930×g for 15 minutes. The cell pellet was resuspended in 2 ml of a solution of 80% YPD and 200 mM HEPES (4-(2-hydroxyethyl)-1-piperazineethanesulfonic acid), pH 6.8. 75 µl of 1 M DTT (dithiothreitol) was added. The resuspended cell pellet was mixed at 100 rpm at 30° C. for 25 minutes. A 40 ml volume of ice cold, sterile water was added to the suspension, and the cells were collected by centrifugation at 1125×g for 15 minutes and placed on ice. The cell pellet was resuspended in 40 ml ice cold water and collected as before for two additional wash steps. The cell pellet was then resuspended in 20 ml of ice cold 1 M sorbitol and collected by centrifugation as before. The final cell pellet was suspended in 0.3 ml ice cold, sterile 1M sorbitol, aliquoted, and frozen at −80° C.

Example 5

Transformation into *P. pastoris*

50-100 ng of plasmid DNA was transformed into 30 µl of electrocompetent *P. pastoris* cells using a 1 mm gap GenePulser cuvette (BioRad) with a GenePulser (BioRad) set at 1.15 kV. 1 ml of YPD/1M sorbitol was added and mixed at a 1:1 ratio to the cells. The cells were allowed to recover for 3 h at 30° C. with shaking at 100 rpm. 100 µl of the recovery mixture was plated on a YPD plate containing the appropriate antibiotic (primary transformation plate), and the rest of the transformed cells were plated on a second YPD plate with the appropriate antibiotic. Plates were incubated at 30° C. for 48 hours. Primary transformation plates were streaked onto additional YPD plates with appropriate antibiotic, and plates were incubated for 48 h at 30° C. Individual clones were patched onto YPD plates with antibiotics and the patches were used to grow the strains in shake flasks for further analysis.

Example 6

Construction of AOX1 Promoter-Green Fluorescent Protein Reporter Vectors

Vectors to monitor expression from the AOX1 promoter and mutated variants were constructed using the Green Fluorescent Protein (GFP) as a reporter protein. The GFP open reading frame was inserted into the pGAB vector (See, e.g., U.S. Pat. No. 9,938,327, incorporated herein by reference in its entirety) with the translation start immediately downstream of the methanol-inducible alcohol oxidase 1 (AOX1) promoter from *Pichia pastoris* and the translation stop signal immediately followed by the transcription terminator sequence from the *P. pastoris* FDH1 gene.

The open reading frame encoding the Dasher GFP variant protein was amplified by PCR from the pJ1214-03c plasmid vector obtained from DNA2.0 Inc. (Newark, Calif.). The Dasher GFP open reading frame was amplified from pJ1214-03c with primers MxO0560 (GAGGGTCTCG-GATGACAGCTTTAACTGAAGGGGCC; SEQ ID NO: 30) and MxO0561 (GAGGGTCTCGATTAT-TGGTAAGTGTCGAGATCAACTGCC; SEQ ID NO: 31), which appended flanking Eco31I/BsaI restriction endonuclease recognition sites. Amplification was accomplished using PCR as described in Example 1.

The amplified Dasher GFP PCR product and the pGAB vector were digested with 10 units of FastDigest Eco31I restriction endonuclease (ThermoFisher Scientific) for 1 hour at 37° C. in 1× FastDigest Buffer (ThermoFisher Scientific). The Eco31I-digested amplified Dasher GFP fragment and pGAB vector were separated by electrophoresis on a 1% agarose gel in 1×TBE buffer (89 mM Tris, 89 mM boric acid, 2 mM EDTA (ethylenediaminetetraacetic acid), pH 8.3) and visualized using SYBR Safe DNA gel stain (Life Technologies, Carlsbad, Calif.). The desired DNA fragments were excised from the agarose gel and the DNA was recovered using the ZYMOCLEAN™ Gel DNA Recovery Kit (Zymo Research, Irvine, Calif.).

The Eco31I-digested fragment containing the Dasher GFP open reading frame was introduced into pGAB at an Eco31I site immediately downstream of the AOX1 promoter by ligation. A mixture containing 72 ng of Eco31I-digested DNA encoding the Dasher GFP open reading frame and 35 ng of Eco31I-digested pGAB was incubated with 400 units of T4 DNA ligase (New England Biolabs) in 1×T4 DNA ligase reaction buffer (50 mM Tris-HCl, 10 mM MgCl$_2$, 1 mM ATP, 10 mM DTT, pH 7.5 @ 25° C.) at 16° C., for 2 hours in a 20 µl reaction. Electrocompetent *E. coli* DH10B cells were transformed with 2 µl of the ligation reaction and antibiotic resistant transformants were selected on LSB (listeria special broth) agar plates supplemented with 100 µg/µl ampicillin. Plates were incubated overnight at 37° C. Colonies were screened for the presence of the insert by PCR using primers MxO0560 and MxO0561. The sequence of the final vector was confirmed by DNA sequencing.

The resulting vector, pMx0369, included the *P. pastoris* AOX1 promoter followed consecutively by the Dasher GFP open reading frame and the *P. pastoris* FDH1 terminator. These elements were amplified from pMx0369 DNA with primers MxO0513 (GTGCTAGGATCCAACATCCAAA-GACG; SEQ ID NO: 32) and MxO0514 (TTTTTCTAGAACCTTATCAAGA-TAGCTAGAAATAGAAATGGTTGC; SEQ ID NO: 33) using the polymerase chain reaction as described in Example 1. The primers introduced BamHI and XbaI restriction sites to the 5' and 3' ends, respectively, of the amplified AOX1 promoter-Dasher GFP-FDH1 terminator DNA fragment. These restriction sites were used to clone the Dasher GFP and the sequences required for its expression into the pIL75 episomal vector. The pIL75 vector carries a panARS autonomous replication sequence (Liachko & Dunham, 2014, FEMS Yeast Res., 14:364-7), which allows for maintenance of the plasmid vector without integration into the genome of the transformed cells, and a kanMX marker for selection of transformants with the antibiotic G418. Both the amplified Dasher GFP expression DNA fragment and the pIL75 vector DNA were digested with 10 units of BamHI and 10 units of XbaI restriction endonucleases (New England Biolabs) in 1× CutSmart buffer (New England Biolabs) for 1 hour at 37° C. The BamHI-XbaI-digested DNA fragments were separated by electrophoresis on a 1% agarose gel in 1×TBE buffer, visualized using SYBR Safe DNA gel stain and the desired DNA fragments were excised from the agarose gel and the DNA was recovered using the Zymoclean Gel DNA Recovery Kit.

The DNA fragment containing the *P. pastoris* AOX1 promoter, the Dasher GFP open reading frame, and the *P. pastoris* FDH1 terminator was introduced into the similarly digested pIL75 vector by ligation. A mixture containing 48 ng of the BamHI-XbaI-digested DNA fragment containing sequences for the expression of Dasher GFP and 15 ng of the BamHI-XbaI-digested pIL75 DNA was incubated with 400 units of T4 DNA ligase (New England Biolabs) in 1×T4 DNA ligase reaction buffer in a 20 µl reaction at 16° C., for 2 hours. Electrocompetent *E. coli* DH10B cells were transformed with 2 µl of the ligation reaction and antibiotic resistant transformants were selected on LSB agar plates supplemented with 100 µg/µl ampicillin. Plates were incubated overnight at 37° C. Colonies were screened for the presence of the insert by PCR using primers MxO0513 and MxO0514. The sequence of the final vector was confirmed by DNA sequencing. The resulting episomal vector, containing sequences encoding the Dasher GFP variant whose expression is under the control of the AOX1 promoter was designated pMx0379.

Example 7

Construction of Strain MxY0270

The pMx0379 vector, carrying the Dasher GFP reporter under the control of the AOX1 promoter, was introduced into *Pichia pastoris* host strain MxY0051 by transformation. The MxY0051 strain is a MutS strain, but contains no other modification. Transformants were selected, and the plasmid was maintained, by growth on medium containing the antibiotic G418. Plates were incubated at 30° C. for 48 hours. Individual clones were patched onto YPD plates with G418 antibiotic and the patches were used to inoculate cultures in subsequent experiments.

Example 8

Error-Prone Mutagenesis of the AOX1 Promoter

The pMx0369 vector was used as a template for error-prone PCR amplification of the AOX1 promoter. Error-prone PCR was carried out as described in McCullum, et al. (2010, Methods in Molecular Biology, 634:103-9). The pAOX1 promoter was amplified using primers MxO0569 (TCCTGCAGCCCGGGGGATCCAACATCCAAAGA; SEQ ID NO: 34) and MxO0570 (CTTCAGTTAAAGCTGT-CATCGTTTCGAATAATTAGT; SEQ ID NO: 35) in a reaction containing 1 µM of each primer, 50 ng of template DNA, 1 mM dCTP and dTTP, 0.2 mM dATP and dGTP, 5.5 mM MgCl$_2$, and 0.5 mM MnCl$_2$, and 5U Taq DNA polymerase, in 1× reaction buffer (Invitrogen). The reaction conditions for error-prone amplification were as follows:

| 1 cycle   | Initial Denaturation | 94° C. | 2 min  |
|-----------|---------------------|--------|--------|
| 25 cycles | Denaturation        | 94° C. | 30 sec |
|           | Annealing           | 55° C. | 30 sec |
|           | Extension           | 72° C. | 2 min  |
| 1 cycle   | Final Extension     | 72° C. | 5 min  |

The pMx0379 vector, excluding the pAOX1 promoter sequence, was amplified under standard PCR amplification conditions, as described in Example 1, using primers MxO0571 (AACAACTAATTATTCGAAAC-GATGACAGCTTTAACT; SEQ ID NO: 36) and MxO0572 (ACCTTTCGTCTTTGGATGTTGGATCCCCCGGG; SEQ ID NO: 37).

The pAOX1 promoter generated by error-prone amplification and the amplified pMx0379 vector DNA were each separated by electrophoresis on a 1% agarose gel in 1×TBE buffer and visualized using SYBR Safe DNA gel stain. The desired DNA fragments were excised from the agarose gel and the DNA was recovered using the ZYMOCLEAN™ Gel DNA Recovery Kit as described herein. The pAOX1 promoter sequences (600 ng) and vector DNA (200 ng) were assembled using Gibson assembly reactions (New England Biolabs). The assembly reactions were used to transform ElectroMax DH10B competent cells as described in Example 3. After overnight growth on LB agar plates with ampicillin, the transformants were pooled in 50 ml LB liquid medium containing ampicillin at a concentration of 100 µg/ml and grown for 4 hours at 37° C. with shaking at 250 rpm. Following outgrowth, plasmid DNA was recovered using a QIAGEN Plasmid Midi kit (Qiagen Inc.). The resulting DNA consisted of pMx0379 vectors containing a variety of mutated pAOX1 promoter sequences.

Example 9

Screening the pAOX1 Mutant Library

The pAOX1 promoter library, consisting of pAOX1 promoters generated by error-prone PCR driving expression of a GFP reporter, was introduced into strain MxY0051 by transformation. Transformants were selected and maintained by growth on YPD plates containing the antibiotic G418. Plates were incubated at 30° C. for 72 hours and colonies were screened for fluorescence using a Li-Cor Odyssey Fc imaging system (Li-Cor Biosciences, Lincoln, NE). A colony that showed significant fluorescence on the YPD was identified. This colony was subcultured onto a fresh YPD plate along with strain MxY0270 as a wild type pAOX1 reference, and confirmed to show increased GFP expression relative to the reference. This strain was designated MxY0279.

Example 10

Recovery of the Mutated Plasmid from MxY0279

Plasmid DNA was recovered from transformed *P. pastoris* cells by resuspending a MxY0279 colony in a 100 µl volume of lysis buffer (200 mM Li acetate, 1% SDS) and heating the suspension to 70° C. for 5 minutes. DNA was precipitated from the lysate by the addition of 300 µl of 100% ethanol, followed by centrifugation at 15,000×g for 3 minutes. The recovered material was washed with a 1 ml volume of 70% ethanol, followed by centrifugation. The precipitated DNA was dissolved in a 100 µl volume of DNA elution buffer (5 mM Tris/HCl, pH 8.5). A 2 µl volume of the recovered DNA solution was used to transform ElectroMax DH10B competent cells as described in Example 3, and bacterial transformants were recovered by plating on LB plates containing ampicillin at a concentration of 100 µg/ml. Plasmid DNA was isolated from the bacterial transformants using a QIAprep Spin Miniprep Kit, and the sequence of the mutated promoter was determined by sequencing the plasmid DNA using the MxO0569 and MxO0570 primers. The recovered plasmid vector containing the mutant pAOX1 promoter driving GFP expression was designated pMx0414. The sequence is set forth in SEQ ID NO:29 as shown in FIG. 2, where 19 mutation sites are double underlined.

Example 11

Confirmation that the Improved GFP Expression in MxY0279 Results from pMx0414

The recovered pMx0414 plasmid was transformed into the MxY0051 strain of *P. pastoris*, as described in Example 3. The transformants and the MxY0270 control strain were streaked onto YPD agar plates and incubated at 30° C. for 3 days. The fluorescence from these cells was measured using a Li-Cor Odyssey Fc imaging system as described in Example 9. The transformants showed significant expression from the mutant pAOX1 promoter on YPD medium, which lacked the inducer methanol, while the MxY0270 control strain bearing a plasmid with GFP driven by the wild type pAOX1 promoter showed greatly reduced or no fluorescence (FIG. 3). These results confirm that improved GFP expression observed in the original MxY0279 strain was due to the mutations in the pMx0414 plasmid, and not the genome of the host strain.

Example 12

Shake Flask Cultivation of Transformants and Measurement of GFP Expression

The MxY0270 and MxY0279 strains carrying the pMx0379 and pMx0414 GFP expression plasmids, as described herein, were inoculated into growth media (1% yeast extract, 2% peptone, supplemented with 1% glycerol) containing the antibiotic G418, to maintain the plasmids, and grown overnight at 30° C. with shaking at 200 rpm. The next day the overnight cultures were diluted to an OD600 of 0.5-0.7 with YP media supplemented with 1% dextrose, 1% glycerol, 1% methanol, or both 1% methanol and 1% dextrose. All media contained the G418 antibiotic.

Figure 4:
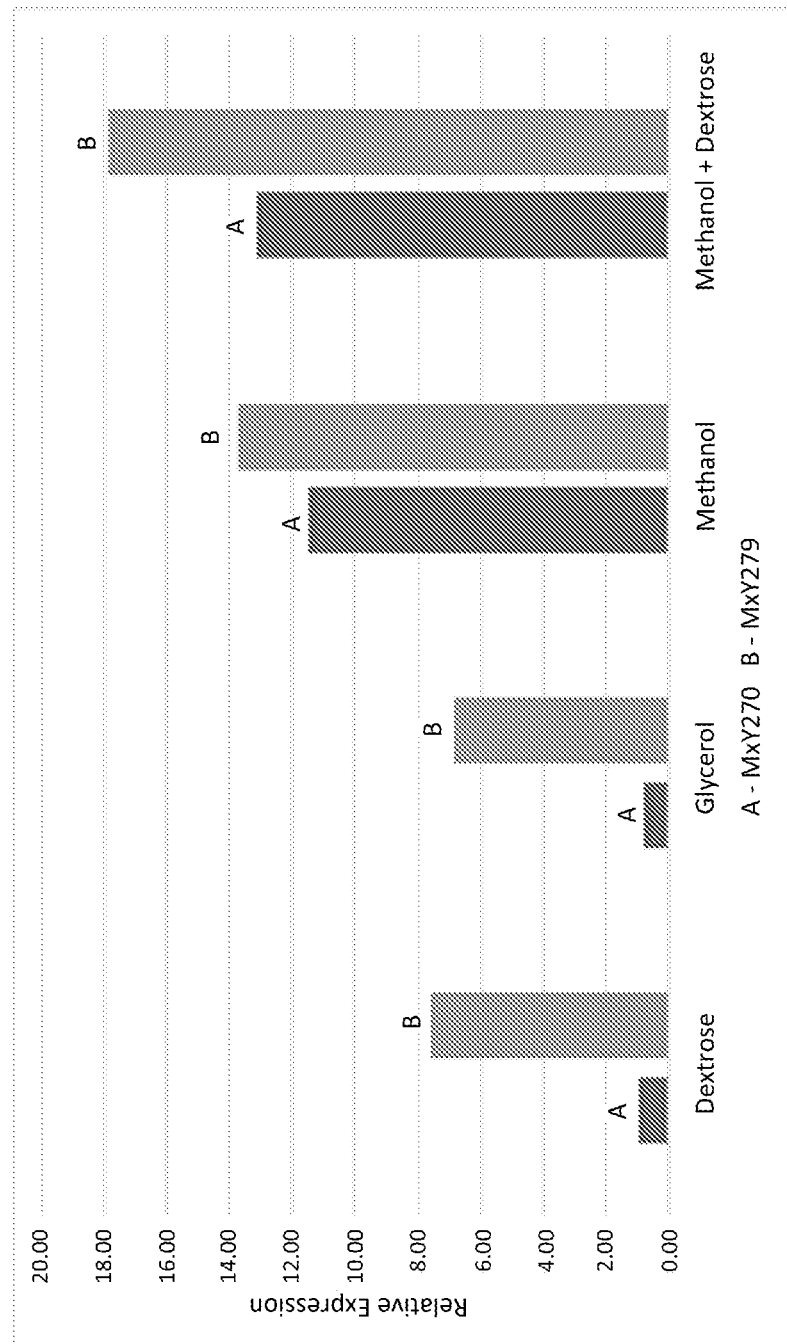
FIG. 4 is a graph plotting the relative expression of GFP in strains MxY0270 and MxY0279 under different growth conditions.

GFP fluorescence was measured in cultures expressing the reporter protein using a SpectraMax M2 microplate reader and SoftMax Pro 6.1 software (Molecular Devices, San Jose, Calif.) at an excitation wavelength of 485 nm, and an emission wavelength of 525 nm. Fluorescence in shake flask cultures was measured at 48 hours after dilution into the relevant carbon source. GFP fluorescence, in relative fluorescence units (RFU) was normalize to the OD of the culture. (See FIG. 4).

Example 13

Evaluation of a Set of Mutations

A combinatorial promoter library containing the mutations present in a plasmid with all 19 mutations in pAOX1 (promoter designated MxG0038; see, e.g., SEQ ID NO: 29), where each of the positions mutated in MxG0038 was either the wild type or mutant nucleotide. A group of five mutations from the MxG0038 mutant that confer the improved expression phenotype was identified. A mutant AOX1 promoter containing mutations T688C, A696T, T702C, A712G, and T714G was designated MxG0220. A portion of the sequences of MxG0038 and MxG0020 are compared in FIG. 5.

Figure 6:
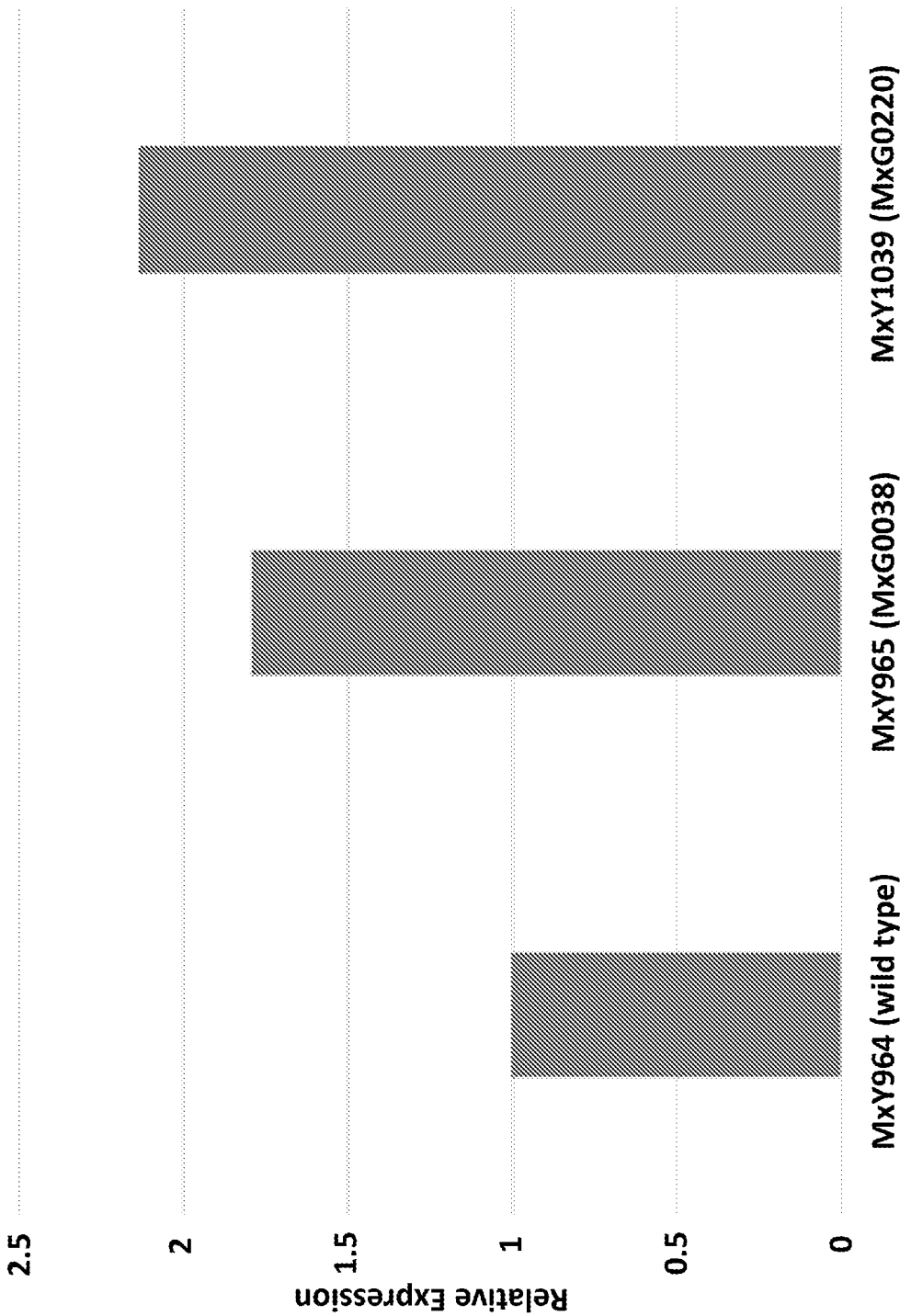
FIG. 6 is a graph plotting the relative expression of GFP in strains MxY0964, MxY965, and MxY1039.

The relative expression of GFP using wild-type pAOX1 promoter, a pAOX1 promoter containing all 19 mutations (promoter designated MxG0038 in strain MxY965), a pAOX1 promoter containing the selected 5 mutations (promoter designated MxG0220) is shown in FIG. 6.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

SEQUENCE LISTING

```
Sequence total quantity: 37
SEQ ID NO: 1            moltype = AA  length = 161
FEATURE                 Location/Qualifiers
source                  1..161
                        mol_type = protein
                        organism = Vigna radiata
SEQUENCE: 1
MTTTLERGFT EEQEALVVKS WNVMKKNSGE LGLKFFLKIF EIAPSAQKLF SFLRDSTVPL   60
EQNPKLKPHA VSVFVMTCDS AVQLRKAGKV TVRESNLKKL GATHFRTGVA NEHFEVTKFA  120
LLETIKEAVP EMWSPAMKNA WGEAYDQLVD AIKYEMKPPS S                      161

SEQ ID NO: 2            moltype = AA  length = 133
FEATURE                 Location/Qualifiers
source                  1..133
                        mol_type = protein
                        organism = Methylacidiphilum infernorum
SEQUENCE: 2
MIDQKEKELI KESWKRIEPN KNEIGLLFYA NLFKEEPTVS VLFQNPISSQ SRKLMQVLGI   60
LVQGIDNLEG LIPTLQDLGR RHKQYGVVDS HYPLVGDCLL KSIQEYLGQG FTEEAKAAWT  120
KVYGIAAQVM TAE                                                    133

SEQ ID NO: 3            moltype = AA  length = 139
FEATURE                 Location/Qualifiers
source                  1..139
                        mol_type = protein
                        organism = Aquifex aeolicus
SEQUENCE: 3
MLSEETIRVI KSTVPLLKEH GTEITARMYE LLFSKYPKTK ELFAGASEEQ PKKLANAIIA   60
YATYIDRLEE LDNAISTIAR SHVRRNVKPE HYPLVKECLL QAIEEVLNPG EEVLKAWEEA  120
YDFLAKTLIT LEKKLYSQP                                              139

SEQ ID NO: 4            moltype = AA  length = 145
```

```
FEATURE                 Location/Qualifiers
source                  1..145
                        mol_type = protein
                        organism = Glycine max
SEQUENCE: 4
MGAFTEKQEA LVSSSFEAFK ANIPQYSVVF YTSILEKAPA AKDLFSFLSN GVDPSNPKLT    60
GHAEKLFGLV RDSAGQLKAN GTVVADAALG SIHAQKAITD PQFVVVKEAL LKTIKEAVGD   120
KWSDELSSAW EVAYDELAAA IKKAF                                         145

SEQ ID NO: 5            moltype = AA   length = 162
FEATURE                 Location/Qualifiers
source                  1..162
                        mol_type = protein
                        organism = Hordeum vulgare
SEQUENCE: 5
MSAAEGAVVF SEEKEALVLK SWAIMKKDSA NLGLRFFLKI FEIAPSARQM FPFLRDSDVP    60
LETNPKLKTH AVSVFVMTCE AAAQLRKAGK ITVRETTLKR LGGTHLKYGV ADGHFEVTRF   120
ALLETIKEAL PADMWGPEMR NAWGEAYDQL VAAIKQEMKP AE                      162

SEQ ID NO: 6            moltype = AA   length = 1153
FEATURE                 Location/Qualifiers
source                  1..1153
                        mol_type = protein
                        organism = Magnaporthe oryzae
SEQUENCE: 6
MDGAVRLDWT GLDLTGHEIH DGVPIASRVQ VMVSFPLFKD QHIIMSSKES PSRKSSTIGQ    60
STRNGSCQAD TQKGQLPPVG EKPKPVKENP MKKLKEMSQR PLPTQHGDGT YPTEKKLTGI   120
GEDLKHIRGY DVKTLLAMVK SKLKGEKLKD DKTMLMERVM QLVARLPTES KKRAELTDSL   180
INELWESLDH PPLNYLGPEH SYRTPDGSYN HPFNPQLGAA GSRYARSVIP TVTPPGALPD   240
PGLIFDSIMG RTPNSYRKHP NNVSSILWYW ATIIIHDIFW TDPRDINTNK SSSYLDLAPL   300
YGNSQEMQDS IRTFKDGRMK PDCYADKRLA GMPPGVSVLL IMFNRFPHNHV AENLALINEG  360
GRFNKPSDLL EGEAREAAWK KYDNDLFQVA RLVTSGLYIN ITLVDYVRNI VNLNRVDTTW   420
TLDPRQDAGA HVGTADGAER GTGNAVSAEF NLCYRWHSCI SEKDSKFVEA QFQNIFGKPA   480
SEVRPDEMWK GFAKMEQNTP ADPGQRTFGG FKRGPDGKFD DDDLVRCISE AVEDVAGAFG   540
ARNVPQAMKV VETMGIIQGR KWNVAGLNEF RKHFHLKPYS TFEDINSDPG VAEALRRLYD   600
HPDNVELYPG LVAEEDKQPM VPGVGIAPTY TISRVVLSDA VCLVRGDRFY TTDFTPRNLT   660
NWGYKEVDYD LSVNHGCVFY KLFIRAFPNH FKQNSVYAHY PMVVPSENKR ILEALGRADL   720
FDFEAPKYIP PRVNITSYGG AEYILETQEK YKVTWHEGLG FLMGEGGLKF MLSGDDPLHA   780
QQRKCMAAQL YKDGWTEAVK AFYAGMMEEL LVSKSYFLGN NKHRHVDIIR DVGNMVHVHF   840
ASQVFGLPLK TAKNPTGVFT EQEMYGILAA IFTTIFFDLD PSKSFPLRTK TREVCQKLAK   900
LVEANVKLIN KIPWSRGMFV GKPAKDEPLS IYGKTMIKGL KAHGLSDYDI AWSHVVPTSG   960
AMVPNQAQVF AQAVDYYLSP AGMHYIPEIH MVALQPSTPE TDALLLGYAM EGIRLAGTFG  1020
SYREAAVDDV VKEDNGRQVP VKAGDRVFVS FVDAARDPKH FPDPEVVNPR RPAKKYIHYG  1080
VGPHACLGRD ASQIAITEMF RCLFRRRNVR RVPGPQGELK KVPRPGGFYV YMREDWGGLF  1140
PFPVTMRVMW DDE                                                    1153

SEQ ID NO: 7            moltype = AA   length = 530
FEATURE                 Location/Qualifiers
source                  1..530
                        mol_type = protein
                        organism = Fusarium oxysporum
SEQUENCE: 7
MKGSATLAFA LVQFSAASQL VWPSKWDEVE DLLYMQGGFN KRGFADALRT CEFGSNVPGT    60
QNTAEWLRTA FHDAITHDAK AGTGGLDASI YWESSRPENP GKAFNNTFGF FSGFHNPRAT   120
ASDLTALGTV LAVGACNGPR IPFRAGRIDA YKAGPAGVPE PSTNLKDTFA AFTKAGFTKE   180
EMTAMVACGH AIGGVHSVDF PEIVGIKADP NNDTNVPFQK DVSSFHNGIV TEYLAGTSKN   240
PLVASKNATF HSDKRIFDND KATMKKLSTK AGFNSMCADI LTRMIDTVPK SVQLTPVLEA   300
YDVRPYITEL SLNNKNKIHF TGSVRVRITN NIRDNNDLAI NLIYVGRDGK KVTVPTQQVT   360
FQGGTSPGAG EVFANFEFDT TMDAKNGITK FFIQEVKPST KATVTHDNQK TGGYKVDDTV   420
LYQLQQSCAV LEKLPNAPLV VTAMVRDARA KDALTLRVAH KKPVKGSIVP RFQTAITNFK   480
ATGKKSSGYT GFQAKTMFEE QSTYFDIVLG GSPASGVQFL TSQAMPSQCS              530

SEQ ID NO: 8            moltype = AA   length = 358
FEATURE                 Location/Qualifiers
source                  1..358
                        mol_type = protein
                        organism = Fusarium graminearum
SEQUENCE: 8
MASATRQFAR AATRATRNGF AIAPRQVIRQ QGRRYYSSEP AQKSSSAWIW LTGAAVAGGA    60
GYYFYGNSAS SATAKVFNPS KEDYQKVYNE IAARLEEKDD YDDGSYGPVL VRLAWHASGT   120
YDKETGTGGS NGATMRFAPE SDHGANAGLA AARDFLQPVK EKFPWITYSD LWILAGVCAI   180
QEMLGPAIPY RPGRSDRDVS GCTPDGRLPD ASKRQDHLRG IFGRMGFNDQ EIVALSGAHA   240
LGRCHTDRSG YSGPWTFSPT VLTNDYFRLL VEEKWQWKKW NGPAQYEDKS TKSLMMLPSD   300
IALIEDKKFK PWVEKYAKDN DAFFKDFSNV VLRLFELGVP FAQGTENQRW TFKPTHQE     358

SEQ ID NO: 9            moltype = AA   length = 122
FEATURE                 Location/Qualifiers
source                  1..122
                        mol_type = protein
```

```
                       organism = Chlamydomonas eugametos
SEQUENCE: 9
MSLFAKLGGR EAVEAAVDKF YNKIVADPTV STYFSNTDMK VQRSKQFAFL AYALGGASEW    60
KGKDMRTAHK DLVPHLSDVH FQAVARHLSD TLTELGVPPE DITDAMAVVA STRTEVLNMP   120
QQ                                                                 122

SEQ ID NO: 10           moltype = AA  length = 121
FEATURE                 Location/Qualifiers
source                  1..121
                        mol_type = protein
                        organism = Tetrahymena pyriformis
SEQUENCE: 10
MNKPQTIYEK LGGENAMKAA VPLFYKKVLA DERVKHFFKN TDMDHQTKQQ TDFLTMLLGG    60
PNHYKGKNMT EAHKGMNLQN LHFDAIIENL AATLKELGVT DAVINEAAKV IEHTRKDMLG   120
K                                                                  121

SEQ ID NO: 11           moltype = AA  length = 117
FEATURE                 Location/Qualifiers
source                  1..117
                        mol_type = protein
                        organism = Paramecium caudatum
SEQUENCE: 11
MSLFEQLGGQ AAVQAVTAQF YANIQADATV ATFFNGIDMP NQTNKTAAFL CAALGGPNAW    60
TGRNLKEVHA NMGVSNAQFT TVIGHLRSAL TGAGVAAALV EQTVAVAETV RGDVVTV     117

SEQ ID NO: 12           moltype = AA  length = 147
FEATURE                 Location/Qualifiers
source                  1..147
                        mol_type = protein
                        organism = Aspergillus niger
SEQUENCE: 12
MPLTPEQIKI IKATVPVLQE YGTKITTAFY MNMSTVHPEL NAVFNTANQV KGHQARALAG    60
ALFAYASHID DLGALGPAVE LICNKHASLY IQADEYKIVG KYLLEAMKEV LGDACTDDIL   120
DAWGAAYWAL ADIMINREAA LYKQSQG                                      147

SEQ ID NO: 13           moltype = AA  length = 165
FEATURE                 Location/Qualifiers
source                  1..165
                        mol_type = protein
                        organism = Zea mays
SEQUENCE: 13
MALAEADDGA VVFGEEQEAL VLKSWAVMKK DAANLGLRFF LKVFEIAPSA EQMFSFLRDS    60
DVPLEKNPKL KTHAMSVFVM TCEAAAQLRK AGKVTVRETT LKRLGATHLR YGVADGHFEV   120
TGFALLETIK EALPADMWSL EMKKAWAEAY SQLVAAIKRE MKPDA                   165

SEQ ID NO: 14           moltype = AA  length = 169
FEATURE                 Location/Qualifiers
source                  1..169
                        mol_type = protein
                        organism = Oryza sativa
SEQUENCE: 14
MALVEGNNGV SGGAVSFSEE QEALVLKSWA IMKKDSANIG LRFFLKIFEV APSASQMFSF    60
LRNSDVPLEK NPKLKTHAMS VFVMTCEAAA QLRKAGKVTV RDTTLKRLGA THFKYGVGDA   120
HFEVTRFALL ETIKEAVPVD MWSPAMKSAW SEAYNQLVAA IKQEMKPAE               169

SEQ ID NO: 15           moltype = AA  length = 160
FEATURE                 Location/Qualifiers
source                  1..160
                        mol_type = protein
                        organism = Arabidopsis thaliana
SEQUENCE: 15
MESEGKIVFT EEQEALVVKS WSVMKKNSAE LGLKLFIKIF EIAPTTKKMF SFLRDSPIPA    60
EQNPKLKPHA MSVFVMCCES AVQLRKTGKV TVRETTLKRL GASHSKYGVV DEHFEVAKYA   120
LLETIKEAVP EMWSPEMKVA WGQAYDHLVA AIKAEMNLSN                         160

SEQ ID NO: 16           moltype = AA  length = 147
FEATURE                 Location/Qualifiers
source                  1..147
                        mol_type = protein
                        organism = Pisum sativum
SEQUENCE: 16
MGFTDKQEAL VNSSWESFKQ NLSGNSILFY TIILEKAPAA KGLFSFLKDT AGVEDSPKLQ    60
AHAEQVFGLV RDSAAQLRTK GEVVLGNATL GAIHVQRGVT DPHFVVVKEA LLQTIKKASG   120
NNWSEELNTA WEVAYDGLAT AIKKAMT                                      147

SEQ ID NO: 17           moltype = AA  length = 145
FEATURE                 Location/Qualifiers
source                  1..145
                        mol_type = protein
```

```
                          organism = Vigna unguiculata
SEQUENCE: 17
MVAFSDKQEA LVNGAYEAFK ANIPKYSVVF YTTILEKAPA AKNLFSFLAN GVDATNPKLT    60
GHAEKLFGLV RDSAAQLRAS GGVVADAALG AVHSQKAVND AQFVVVKEAL VKTLKEAVGD   120
KWSDELGTAV ELAYDELAAA IKKAY                                         145

SEQ ID NO: 18           moltype = AA  length = 154
FEATURE                 Location/Qualifiers
source                  1..154
                        mol_type = protein
                        organism = Bos taurus
SEQUENCE: 18
MGLSDGEWQL VLNAWGKVEA DVAGHGQEVL IRLFTGHPET LEKFDKFKHL KTEAEMKASE    60
DLKKHGNTVL TALGGILKKK GHHEAEVKHL AESHANKHKI PVKYLEFISD AIIHVLHAKH   120
PSDFGADAQA AMSKALELFR NDMAAQYKVL GFHG                               154

SEQ ID NO: 19           moltype = AA  length = 154
FEATURE                 Location/Qualifiers
source                  1..154
                        mol_type = protein
                        organism = Sus scrofa
SEQUENCE: 19
MGLSDGEWQL VLNVWGKVEA DVAGHGQEVL IRLFKGHPET LEKFDKFKHL KSEDEMKASE    60
DLKKHGNTVL TALGGILKKK GHHEAELTPL AQSHATKHKI PVKYLEFISE AIIQVLQSKH   120
PGDFGADAQG AMSKALELFR NDMAAKYKEL GFQG                               154

SEQ ID NO: 20           moltype = AA  length = 154
FEATURE                 Location/Qualifiers
source                  1..154
                        mol_type = protein
                        organism = Equus caballus
SEQUENCE: 20
MGLSDGEWQQ VLNVWGKVEA DIAGHGQEVL IRLFTGHPET LEKFDKFKHL KTEAEMKASE    60
DLKKHGTVVL TALGGILKKK GHHEAELKPL AQSHATKHKI PIKYLEFISD AIIHVLHSKH   120
PGDFGADAQG AMTKALELFR NDIAAKYKEL GFQG                               154

SEQ ID NO: 21           moltype = AA  length = 152
FEATURE                 Location/Qualifiers
source                  1..152
                        mol_type = protein
                        organism = Nicotiana benthamiana
SEQUENCE: 21
MSSFTEEQEA LVVKSWDSMK KNAGEWGLKL FLKIFEIAPS AKKLFSFLKD SNVPLEQNAK    60
LKPHSKSVFV MTCEAAVQLR KAGKVVVRDS TLKKLGATHF KYGVADEHFE VTKFALLETI   120
KEAVPEMWSV DMKNAWGEAF DQLVNAIKTE MK                                 152

SEQ ID NO: 22           moltype = AA  length = 132
FEATURE                 Location/Qualifiers
source                  1..132
                        mol_type = protein
                        organism = Bacillus subtilis
SEQUENCE: 22
MGQSFNAPYE AIGEELLSQL VDTFYERVAS HPLLKPIFPS DLTETARKQK QFLTQYLGGP    60
PLYTEEHGHP MLRARHLPFP ITNERADAWL SCMKDAMDHV GLEGEIREFL FGRLELTARH   120
MVNQTEAEDR SS                                                       132

SEQ ID NO: 23           moltype = AA  length = 131
FEATURE                 Location/Qualifiers
source                  1..131
                        mol_type = protein
                        organism = Corynebacterium glutamicum
SEQUENCE: 23
MTTSENFYDS VGGEETFSLI VHRFYEQVPN DDILGPMYPP DDFEGAEQRL KMFLSQYWGG    60
PKDYQEQRGH PRLRMRHVNY PIGVTAAERW LQLMSNALDG VDLTAEQREA IWEHMVRAAD   120
MLINSNPDPH A                                                        131

SEQ ID NO: 24           moltype = AA  length = 124
FEATURE                 Location/Qualifiers
source                  1..124
                        mol_type = protein
                        organism = Synechocystis sp.
SEQUENCE: 24
MSTLYEKLGG TTAVDLAVDK FYERVLQDDR IKHFFADVDM AKQRAHQKAF LTYAFGGTDK    60
YDGRYMREAH KELVENHGLN GEHFDAVAED LLATLKEMGV PEDLIAEVAA VAGAPAHKRD   120
VLNQ                                                                124

SEQ ID NO: 25           moltype = AA  length = 183
FEATURE                 Location/Qualifiers
source                  1..183
```

```
                        mol_type = protein
                        organism = Synechococcus sp.
SEQUENCE: 25
MDVALLEKSF EQISPRAIEF SASFYQNLFH HHPELKPLFA ETSQTIQEKK LIFSLAAIIE      60
NLRNPDILQP ALKSLGARHA EVGTIKSHYP LVGQALIETF AEYLAADWTE QLATAWVEAY    120
DVIASTMIEG ADNPAAYLEP ELTFYEWLDL YGEESPKVRN AIATLTHFHY GEDPQDVQRD    180
SRG                                                                  183

SEQ ID NO: 26           moltype = AA   length = 118
FEATURE                 Location/Qualifiers
source                  1..118
                        mol_type = protein
                        organism = Nostoc commune
SEQUENCE: 26
MSTLYDNIGG QPAIEQVVDE LHKRIATDSL LAPVFAGTDM VKQRNHLVAF LAQIFEGPKQ     60
YGGRPMDKTH AGLNLQQPHF DAIAKHLGER MAVRGVSAEN TKAALDRVTN MKGAILNK     118

SEQ ID NO: 27           moltype = AA   length = 136
FEATURE                 Location/Qualifiers
source                  1..136
                        mol_type = protein
                        organism = Bacillus megaterium
SEQUENCE: 27
MREKIHSPYE LLGGEHTISK LVDAFYTRVG QHPELAPIFP DNLTETARKQ KQFLTQYLGG     60
PSLYTEEHGH PMLRARHLPF EITPSRAKAW LTCMHEAMDE INLEGPERDE LYHRLILTAQ   120
HMINSPEQTD EKGFSH                                                   136

SEQ ID NO: 28           moltype = DNA  length = 933
FEATURE                 Location/Qualifiers
source                  1..933
                        mol_type = genomic DNA
                        organism = Pichia pastoris
SEQUENCE: 28
aacatccaaa gacgaaaggt tgaatgaaac cttttttgcca tccgacatcc acaggtccat    60
tctcacacat aagtgccaaa cgcaacagga ggggatacac tagcagcaga ccgttgcaaa   120
cgcaggacct ccactcctct tctcctcaac acccactttt gccatcgaaa accagccca    180
gttattgggc ttgattggag ctcgctcatt ccaattcctt ctattaggct actaaccaca   240
tgactttatt agcctgtcta tcctggcccc cctggcgagg ttcatgtttg tttatttccg   300
aatgcaacaa gctccgcatt acacccgaac atcactccag atgagggctt tctgagtgtg   360
gggtcaaata gtttcatgtt ccccaaatgg cccaaaactg acagtttaaa cgctgtcttg   420
gaacctaata tgacaaaagc gtgatctcat ccaagatgaa ctaagtttgg ttcgttgaaa   480
tgctaacggc cagttggtca aaaagaaact tccaaaagtc ggcataccgt tgtcttgtt    540
tggtattgat tgacgaatgc tcaaaaataa tctcattaat gcttagcgca gtctctctat   600
cgcttctgaa ccccggtgca cctgtgccga aacgcaaatg gggaaacacc cgcttttttgg   660
atgattatgc attgtctcca cattgtatgc ttccaagatt ctggtgggaa tactgctgat   720
agcctaacgt tcatgatcaa aatttaactg ttctaacccc tacttgacag caatatataa   780
acagaaggaa gctgccctgt cttaaaacctt tttttttatc atcattatta gcttactttc   840
ataattgcga ctggttccaa ttgacaagct tttgatttta acgactttta acgacaactt    900
gagaagatca aaaaacaact aattattcga aac                                933

SEQ ID NO: 29           moltype = DNA  length = 933
FEATURE                 Location/Qualifiers
misc_feature            1..933
                        note = mutated sequence
source                  1..933
                        mol_type = other DNA
                        organism = synthetic construct
SEQUENCE: 29
aacatccaaa gacgaaaggt tgaatgaaac cttttttgcca tccgacatcc acaggtccat    60
tctcacacat aagtgccaaa cgcaacagga ggggatacac tagcagcaga ccgttgcaaa   120
cgcaggacct ccactcctct tctccccaac acctactttt gccatcgaaa accagccca    180
gttattgggc ttgattggag ctcgctcatt ccaattcctt ctattaggct actaaccaca   240
tgactttatt agcctgtcta tcctggcccc cctggcgagg ttcatgtttg tttatttccg   300
aatgcaacaa gctccgcatt acacccgaac atcactccag atgagggctt tctgagtgtg   360
gggtcaaata gtttcatgtt ccccaaatgg cccaaaactg acagtttaaa cgctgtcttg   420
gaaccaaata tgtcgaaagc gtgatctcat ccaagatgaa ctaagtttgg ttcgttgaaa   480
tgctaacggc cagttggtca aaaagaaact tccaaaagtc ggcataccga ttgtcttgtt   540
tggtattgat tgacgaatgc tcaaaaataa tttcattaat gcttagcgca gtctccctat   600
cgcttctgaa ccccggcgca cctgtgccga aacgcaaatg gggaaacacc cgcttttttgg   660
atgattatgc attgtctcca cattgtacgc ttccatgatt ccggtgggga tgcggctgat   720
agcctaacgt tcatgatcaa aatttaactg ttctaacccc tacttgacag caatatataa   780
acagaaggag gctgccctgt cttaaaacctt tttttttatc atcattatta gcttactttc   840
ttaattgcga ctggttccaa tagacaagct tttgatttta acgactttta acgacaactt    900
gagaagatca aaaaacaact aattattcga aac                                933

SEQ ID NO: 30           moltype = DNA  length = 35
FEATURE                 Location/Qualifiers
misc_feature            1..35
                        note = synthetic primer
```

```
                            source          1..35
                                            mol_type = other DNA
                                            organism = synthetic construct
SEQUENCE: 30
gagggtctcg gatgacagct ttaactgaag gggcc                              35

SEQ ID NO: 31               moltype = DNA   length = 39
FEATURE                     Location/Qualifiers
misc_feature                1..39
                            note = synthetic primer
source                      1..39
                            mol_type = other DNA
                            organism = synthetic construct
SEQUENCE: 31
gagggtctcg attattggta agtgtcgaga tcaactgcc                          39

SEQ ID NO: 32               moltype = DNA   length = 26
FEATURE                     Location/Qualifiers
misc_feature                1..26
                            note = synthetic primer
source                      1..26
                            mol_type = other DNA
                            organism = synthetic construct
SEQUENCE: 32
gtgctaggat ccaacatcca aagacg                                        26

SEQ ID NO: 33               moltype = DNA   length = 45
FEATURE                     Location/Qualifiers
misc_feature                1..45
                            note = synthetic primer
source                      1..45
                            mol_type = other DNA
                            organism = synthetic construct
SEQUENCE: 33
tttttctaga accttatcaa gatagctaga aatagaaatg gttgc                   45

SEQ ID NO: 34               moltype = DNA   length = 32
FEATURE                     Location/Qualifiers
misc_feature                1..32
                            note = synthetic primer
source                      1..32
                            mol_type = other DNA
                            organism = synthetic construct
SEQUENCE: 34
tcctgcagcc cgggggatcc aacatccaaa ga                                 32

SEQ ID NO: 35               moltype = DNA   length = 36
FEATURE                     Location/Qualifiers
misc_feature                1..36
                            note = synthetic primer
source                      1..36
                            mol_type = other DNA
                            organism = synthetic construct
SEQUENCE: 35
cttcagttaa agctgtcatc gtttcgaata attagt                             36

SEQ ID NO: 36               moltype = DNA   length = 36
FEATURE                     Location/Qualifiers
misc_feature                1..36
                            note = synthetic primer
source                      1..36
                            mol_type = other DNA
                            organism = synthetic construct
SEQUENCE: 36
aacaactaat tattcgaaac gatgacagct ttaact                             36

SEQ ID NO: 37               moltype = DNA   length = 32
FEATURE                     Location/Qualifiers
misc_feature                1..32
                            note = synthetic primer
source                      1..32
                            mol_type = other DNA
                            organism = synthetic construct
SEQUENCE: 37
acctttcgtc tttggatgtt ggatcccccg gg                                 32
```

What is claimed is:

1. A nucleic acid construct comprising a first alcohol oxidase promoter element, wherein the first alcohol oxidase promoter element comprises a mutation at one or more nucleotide positions corresponding to any of nucleotide positions 668-734 relative to SEQ ID NO: 28.

2. The nucleic acid construct of claim 1, wherein the first alcohol oxidase promoter element comprises a mutation at one or more nucleotide positions corresponding to any of nucleotide positions 678-724 relative to SEQ ID NO: 28.

3. The nucleic acid construct of claim 2, wherein the first alcohol oxidase promoter element comprises a mutation at one or more nucleotide positions corresponding to any of nucleotide positions 688-714 relative to SEQ ID NO: 28.

4. The nucleic acid construct of claim 1, wherein the first alcohol oxidase promoter element comprises two or more mutations at nucleotide positions corresponding to any of nucleotide positions 668-734 relative to SEQ ID NO: 28.

5. The nucleic acid construct of claim 1, wherein the first alcohol oxidase promoter element is an alcohol oxidase 1 promoter element.

6. The nucleic acid construct of claim 1, further comprising a nucleotide sequence, wherein the nucleotide sequence is operably linked to the first alcohol oxidase promoter element.

7. The nucleic acid construct of claim 6, wherein the nucleotide sequence encodes a first protein.

8. The nucleic acid construct of claim 7, wherein the first protein is selected from the group consisting of an antibody or fragment thereof, an enzyme, a regulatory protein, a peptide hormone, a blood clotting protein, a cytokine, a cytokine inhibitor, and a heme-binding protein.

9. The nucleic acid construct of claim 7, wherein the first protein is a heme-binding protein.

10. A cell comprising a first nucleic acid construct, wherein the first nucleic acid construct is the nucleic acid construct of claim 1.

11. A method of producing a product in a cell comprising:
expressing a nucleic acid construct comprising a nucleotide sequence operably linked to a first alcohol oxidase promoter element, wherein the first alcohol oxidase promoter element comprises a mutation at one or more nucleotide positions corresponding to any of nucleotide positions 668-734 relative to SEQ ID NO: 28.

12. The method of claim 11, wherein the first alcohol oxidase promoter element comprises a mutation at one or more nucleotide positions corresponding to any of nucleotide positions 678-724 relative to SEQ ID NO: 28.

13. The method of claim 11, wherein the first alcohol oxidase promoter element is an alcohol oxidase 1 promoter element.

14. The method of claim 11, wherein the nucleotide sequence operably linked to the first alcohol oxidase promoter element encodes a first protein.

15. The method of claim 11, wherein the method is carried out in the absence of added methanol.

16. The method of claim 11, wherein the method is carried out in the presence of added methanol.

17. The method of claim 11, wherein the first alcohol oxidase promoter element comprises a mutation at one or more nucleotide positions corresponding to any of nucleotide positions 688-714 relative to SEQ ID NO: 28.

18. The method of claim 11, wherein the first alcohol oxidase promoter element comprises two or more mutations at nucleotide positions corresponding to any of nucleotide positions 668-734 relative to SEQ ID NO: 28.

19. The method of claim 14, wherein the first protein is selected from the group consisting of an antibody or fragment thereof, an enzyme, a regulatory protein, a peptide hormone, a blood clotting protein, a cytokine, a cytokine inhibitor, and a heme-binding protein.

20. The method of claim 14, wherein the first protein is a heme-binding protein.

* * * * *